US007972793B2

(12) United States Patent
Ramsey et al.

(10) Patent No.: US 7,972,793 B2
(45) Date of Patent: *Jul. 5, 2011

(54) METHODS AND COMPOSITIONS FOR THE TREATMENT OF PSYCHOTIC DISORDERS THROUGH THE IDENTIFICATION OF THE SULT4A1-1 HAPLOTYPE

(75) Inventors: Timothy L. Ramsey, Shelbyville, KY (US); Mark D. Brennan, Jeffersonville, IN (US)

(73) Assignee: Suregene, LLC, Jeffersontown, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/939,049

(22) Filed: Nov. 3, 2010

(65) Prior Publication Data

US 2011/0105469 A1 May 5, 2011

Related U.S. Application Data

(63) Continuation-in-part of application No. 12/859,056, filed on Aug. 18, 2010, and a continuation-in-part of application No. 12/858,971, filed on Aug. 18, 2010, each which is a continuation-in-part of application No. 12/646,723, filed on Dec. 23, 2009, now Pat. No. 7,790,396, and a continuation-in-part of application No. 12/612,438, filed on Nov. 4, 2009.

(51) Int. Cl.
*C12P 19/34* (2006.01)
*C12Q 1/68* (2006.01)
(52) U.S. Cl. .............................. 435/6; 435/91.1; 436/63
(58) Field of Classification Search .................... None
See application file for complete search history.

(56) References Cited

U.S. PATENT DOCUMENTS

| | | | |
|---|---|---|---|
| 7,425,624 B1 | 9/2008 | Thomae et al. | 536/23.1 |
| 7,745,185 B1 | 6/2010 | Thomae et al. | 435/183 |
| 7,790,396 B1 | 9/2010 | Ramsey et al. | 435/6 |
| 2002/0115073 A1 | 8/2002 | Papadopoulos et al. | 435/6 |
| 2003/0170176 A1 | 9/2003 | Leyland-Jones | 424/9.1 |
| 2004/0072156 A1 | 4/2004 | Nakamura et al. | 435/6 |
| 2006/0177851 A1 | 8/2006 | Brennan et al. | 435/6 |
| 2006/0223065 A1 | 10/2006 | Von Der Kammer et al. | 435/6 |
| 2006/0257903 A1 | 11/2006 | Akil et al. | 435/6 |
| 2007/0031853 A1 | 2/2007 | Stanton, Jr. et al. | 435/6 |
| 2007/0105105 A1 | 5/2007 | Clelland et al. | 435/6 |
| 2007/0105128 A1 | 5/2007 | Nakamura et al. | 435/6 |
| 2009/0012371 A1 | 1/2009 | Brennan et al. | 600/300 |
| 2010/0119626 A1 | 5/2010 | Ramsey et al. | 424/722 |
| 2010/0120046 A1 | 5/2010 | Brennan et al. | 435/6 |
| 2010/0151461 A1 | 6/2010 | Brennan | 435/6 |

FOREIGN PATENT DOCUMENTS

| | | |
|---|---|---|
| WO | WO 00/50639 | 8/2000 |
| WO | WO 02/18541 | 3/2002 |
| WO | WO 02/052044 | 7/2002 |
| WO | WO 02/066684 | 8/2002 |
| WO | WO 02/073196 | 9/2002 |
| WO | WO 02/073206 | 9/2002 |
| WO | WO 03/042654 | 5/2003 |
| WO | WO 2004/005882 | 1/2004 |
| WO | WO 2004/033722 | 4/2004 |
| WO | WO 2005/020784 | 3/2005 |
| WO | WO 2005/030947 | 4/2005 |
| WO | WO 2006/072075 | 7/2006 |
| WO | WO 2009/008896 | 1/2009 |
| WO | WO 2009/082743 | 7/2009 |
| WO | WO 2009/089120 | 7/2009 |
| WO | WO 2009/092032 | 7/2009 |
| WO | WO 2010/036353 | 4/2010 |
| WO | WO 2010/036943 | 4/2010 |
| WO | WO 2010/036969 | 4/2010 |
| WO | WO 2010/067372 | 6/2010 |

OTHER PUBLICATIONS

Bishop et al., "Association between the polymorphic *GRM3* gene and negative symptom improvement during olanzapine treatment," *Schizophrenia Research*, 77:253-260, 2005.
Brennan and Condra, "Transmission disequilibrium suggests a role for the sulfotransferase-4A1 gene in schizophrenia," *American Journal of Medical Genetics Part B (Neuropsychiatric Genetics)*, 139B:69-72, 2005.
Condra et al., "Evidence for two schizophrenia susceptibility genes on chromosome 22q13," *Psychiatric Genetics*, 17(5):292-298, 2007.
Coughtrie, "Sulfation through the looking glass—recent advances in sulfotransferase research for the curious," *The Pharmacogenomics Journal*, 2:297-308, 2002.
Gamage et al., "Human sulfotransferases and their role in chemical metabolism," *Toxicological Sciences*, 90(1):5-22, 2006.
Hildebrandt et al., "Genetic diversity and function in the human cytosolic sulfotransferases," *The Pharmacogenomics Journal*, 7:133-143, 2007.
Kauffman, "Sulfonation in pharmacology and toxicology," *Drug Metab. Rev.*, 36(3-4):823-843, 2004.
Lewis and Minchin, "Lack of exonic sulfotransferase 4A1 mutations in controls and schizophrenia cases," *Psychiatr. Genet.*, 19(1):53-55, 2009.
Lindsay et al., "Structure, function and polymorphism of human cytosolic sulfotransferases," *Curr. Drug Metab.*, 9(2):99-105, 2008.
McClay et al., "Genome-wide pharmacogenomic analysis of response to treatment with antipsychotics," *Molecular Psychiatry*, 1-10 (E-pub ahead of print), 2009.
Meltzer et al., "Association of *Sult4A1* SNPs with psychopathology and cognition in patients with schizophrenia or schizoaffective disorder," *Schizophrenia Research*, 106:258-264, 2008.
Minchin et al., "Sulfotransferase 4A1," *Int. J. Biochem. Cell Biol.*, 40(12):2686-2691, 2008.

(Continued)

*Primary Examiner* — Sarae Bausch
(74) *Attorney, Agent, or Firm* — Fulbright & Jaworski L.L.P.

(57) ABSTRACT

Methods and compositions that relate to genetic markers of psychotic disorders, e.g., schizophrenia (SZ), are provided. For example, in certain aspects methods for determinations of a SULT4A1-1 haplotype are described. Furthermore, the invention provides methods and compositions involving treatment of psychotic disorders using the haplotype status.

8 Claims, 7 Drawing Sheets

OTHER PUBLICATIONS

Schwonbeck et al., "Cohort analysis of a single nucleotide polymorphism on DNA chips," *Biosensors and Bioelectronics*, 20:956-966, 2004.

Single Nucleotide Polymorphism Cluster Report: rs2285162, National Center for Biotechnology Information (NCBI), printed Oct. 19, 2009.

Single Nucleotide Polymorphism Cluster Report: rs2285166, National Center for Biotechnology Information (NCBI), printed Oct. 19, 2009.

Single Nucleotide Polymorphism Cluster Report: rs2285167, National Center for Biotechnology Information (NCBI), printed Oct. 19, 2009.

Single Nucleotide Polymorphism Cluster Report: rs763120, National Center for Biotechnology Information (NCBI), printed Nov. 2, 2009.

U.S. Appl. No. 12/612,438, entitled "Methods and Compositions for the Treatment of Psychotic Disorders Through the Identification of the Sult4A1-1 Haplotype," by Timothy L. Ramsey and Mark D. Brennan, filed Nov. 4, 2009.

U.S. Appl. No. 12/646,723, entitled "Methods and Compositions for the Treatment of Psychotic Disorders Through the Identification of the SULT4A1-1 Haplotype," by Timothy L. Ramsey and Mark D. Brennan, filed Dec. 23, 2009.

U.S. Appl. No. 12/858,917, entitled "Methods and Compositions for the Treatment of Psychotic Disorders Through the Identification of the SULT4A1-1 Haplotype," by Timothy L. Ramsey and Mark D. Brennan, filed Aug. 18, 2010.

U.S. Appl. No. 12/859,056, entitled "Methods and Compositions for the Treatment of Psychotic Disorders Through the Identification of the SULT4A1-1 Haplotype," by Timothy L. Ramsey and Mark D. Brennan, filed Aug. 18, 2010.

Wall and Pritchard, "Haplotype blocks and linkage disequilibrium in the human genome," *Nat. Rev. Genet.*, 4(8):587-597, 2003.

International Search Report issued in PCT/US2010/055457 dated Feb. 17, 2011.

SEQUENCE LISTING

<160> NUMBER OF SEQ ID NOS: 31

<210> SEQ ID NO 1
<211> LENGTH: 61
<212> TYPE: DNA
<213> ORGANISM: Homo sapiens

<400> SEQUENCE: 1
ggcagccaca agggagggct gagctgtggg mtaaactgca ggcaccggtc tacgctggtt    60
t                                                                    61

<210> SEQ ID NO 2
<211> LENGTH: 61
<212> TYPE: DNA
<213> ORGANISM: Homo sapiens

<400> SEQUENCE: 2
tccgcgccac gcaggtggag gagcctcgcc rtctgcgcag aagccagaca gcaaaaccca    60
t                                                                    61

<210> SEQ ID NO 3
<211> LENGTH: 61
<212> TYPE: DNA
<213> ORGANISM: Homo sapiens

<400> SEQUENCE: 3
catgcttcca ccatgcctag ccaatgaggg ytccataaaa ggcccaagag gacaggcttt    60
g                                                                    61

<210> SEQ ID NO 4
<211> LENGTH: 61
<212> TYPE: DNA
<213> ORGANISM: Homo sapiens

<400> SEQUENCE: 4
cacctccaaa aggaaaagga aaggtgaag racgtctgtt aaacgcctgc tgcggccagt    60
c                                                                    61

<210> SEQ ID NO 5
<211> LENGTH: 61
<212> TYPE: DNA
<213> ORGANISM: Homo sapiens

<400> SEQUENCE: 5
tcaacacaat gccctcgaca cagagcacga ygggaagctc taagaggaaa agtagagttc    60
c                                                                    61

<210> SEQ ID NO 6
<211> LENGTH: 61
<212> TYPE: DNA
<213> ORGANISM: Homo sapiens

<400> SEQUENCE: 6
tccacagtca ggcctgacca gtccaggaag mtccggcaac cctggcttgg ccccagcctc    60
t                                                                    61

<210> SEQ ID NO 7
<211> LENGTH: 61
<212> TYPE: DNA

<213> ORGANISM: Homo sapiens

<400> SEQUENCE: 7
aagctttggg gaaaggaggc tctggtgtgc rgcattaagg gccccagttt gccctcatgt    60
a                                                                    61

<210> SEQ ID NO 8
<211> LENGTH: 61
<212> TYPE: DNA
<213> ORGANISM: Homo sapiens

<400> SEQUENCE: 8
cgtgtggggg gcaggtgcca actcttgtcc yttagtggtt gggtgtggct cagggcgtcg    60
g                                                                    61

<210> SEQ ID NO 9
<211> LENGTH: 61
<212> TYPE: DNA
<213> ORGANISM: Homo sapiens

<400> SEQUENCE: 9
ggcctatttc atggcaaagt tgtgaggatg rggaggataa aacaaagtac ttggcacaaa    60
g                                                                    61

<210> SEQ ID NO 10
<211> LENGTH: 61
<212> TYPE: DNA
<213> ORGANISM: Homo sapiens

<400> SEQUENCE: 10
gatcaggagg gaccactagg gccacttccc yctagatgca ggacactgga aagagctgcc    60
c                                                                    61

<210> SEQ ID NO 11
<211> LENGTH: 61
<212> TYPE: DNA
<213> ORGANISM: Homo sapiens

<400> SEQUENCE: 11
ggcgagagga attcaggtaa aatgtttcca ygctggtaaa agccaagggt gagcccatgt    60
g                                                                    61

<210> SEQ ID NO 12
<211> LENGTH: 61
<212> TYPE: DNA
<213> ORGANISM: Homo sapiens

<400> SEQUENCE: 12
agcagaagaa aggagcagtt agccacagat yggtccacag agattaccca aactggaaca    60
a                                                                    61

<210> SEQ ID NO 13
<211> LENGTH: 61
<212> TYPE: DNA
<213> ORGANISM: Homo sapiens

<400> SEQUENCE: 13
gattcctacc tctaagtagt gtagccagga rgatggaagg agtttacacc aacaagaatc    60
t                                                                    61

```
<210> SEQ ID NO 14
<211> LENGTH: 61
<212> TYPE: DNA
<213> ORGANISM: Homo sapiens

<400> SEQUENCE: 14
gccaaagaag gctcctggct gtgttcatgt ygtctctcaa gggatcctgg caggctgagc    60
c                                                                    61

<210> SEQ ID NO 15
<211> LENGTH: 61
<212> TYPE: DNA
<213> ORGANISM: Homo sapiens

<400> SEQUENCE: 15
acctggcacg tggcaggtgt ttaataaaca ycccaggagc gagtatgatc tgccgcggga    60
g                                                                    61

<210> SEQ ID NO 16
<211> LENGTH: 11
<212> TYPE: DNA
<213> ORGANISM: Homo sapiens

<400> SEQUENCE: 16
acgcaagctc a                                                         11

<210> SEQ ID NO 17
<211> LENGTH: 11
<212> TYPE: DNA
<213> ORGANISM: Homo sapiens

<400> SEQUENCE: 17
acgccggctc a                                                         11

<210> SEQ ID NO 18
<211> LENGTH: 11
<212> TYPE: DNA
<213> ORGANISM: Homo sapiens

<400> SEQUENCE: 18
acgcaaactc a                                                         11

<210> SEQ ID NO 19
<211> LENGTH: 11
<212> TYPE: DNA
<213> ORGANISM: Homo sapiens

<400> SEQUENCE: 19
atgccggctc a                                                         11

<210> SEQ ID NO 20
<211> LENGTH: 11
<212> TYPE: DNA
<213> ORGANISM: Homo sapiens

<400> SEQUENCE: 20
gcaccggtct g                                                         11

<210> SEQ ID NO 21
<211> LENGTH: 11
<212> TYPE: DNA
<213> ORGANISM: Homo sapiens
```

```
<400> SEQUENCE: 21
gcgtcggctc g                                                            11

<210> SEQ ID NO 22
<211> LENGTH: 11
<212> TYPE: DNA
<213> ORGANISM: Homo sapiens

<400> SEQUENCE: 22
gcaccagtct g                                                            11

<210> SEQ ID NO 23
<211> LENGTH: 11
<212> TYPE: DNA
<213> ORGANISM: Homo sapiens

<400> SEQUENCE: 23
acgccggctc g                                                            11

<210> SEQ ID NO 24
<211> LENGTH: 11
<212> TYPE: DNA
<213> ORGANISM: Homo sapiens

<400> SEQUENCE: 24
gcgccggctc a                                                            11

<210> SEQ ID NO 25
<211> LENGTH: 11
<212> TYPE: DNA
<213> ORGANISM: Homo sapiens

<400> SEQUENCE: 25
gcgccggtct g                                                            11

<210> SEQ ID NO 26
<211> LENGTH: 12
<212> TYPE: DNA
<213> ORGANISM: Homo sapiens

<400> SEQUENCE: 26
acgcaaggct ca                                                           12

<210> SEQ ID NO 27
<211> LENGTH: 12
<212> TYPE: DNA
<213> ORGANISM: Homo sapiens

<400> SEQUENCE: 27
acgccgagct ca                                                           12

<210> SEQ ID NO 28
<211> LENGTH: 12
<212> TYPE: DNA
<213> ORGANISM: Homo sapiens

<400> SEQUENCE: 28
acgcaagact ca                                                           12

<210> SEQ ID NO 29
<211> LENGTH: 12
<212> TYPE: DNA
<213> ORGANISM: Homo sapiens
```

```
<400> SEQUENCE: 29
atgccgagct ca                                                          12

<210> SEQ ID NO 30
<211> LENGTH: 12
<212> TYPE: DNA
<213> ORGANISM: Homo sapiens

<400> SEQUENCE: 30
gcaccgggtc tg                                                          12

<210> SEQ ID NO 31
<211> LENGTH: 12
<212> TYPE: DNA
<213> ORGANISM: Homo sapiens

<400> SEQUENCE: 31
gcgtcgggct cg                                                          12
```

METHODS AND COMPOSITIONS FOR THE TREATMENT OF PSYCHOTIC DISORDERS THROUGH THE IDENTIFICATION OF THE SULT4A1-1 HAPLOTYPE

CROSS-REFERENCE TO RELATED APPLICATIONS

This application is a continuation-in-part of U.S. application Ser. No. 12/859,056, filed Aug. 18, 2010, and U.S. application Ser. No. 12/858,971, filed Aug. 18, 2010, each of which is a continuation-in-part of U.S. application Ser. No. 12/646,723, filed Dec. 23, 2009, now issued as U.S. Pat. No. 7,790,396, and U.S. application Ser. No. 12/612,438, filed Nov. 4, 2009. The entire contents of each of the referenced applications are incorporated herein by reference.

This invention was made with government support under SBIR grant MH078347 and grants N01 MH900001 and MH074027 awarded by National Institutes of Mental Health. The government has certain rights in the invention.

BACKGROUND OF THE INVENTION

1. Field of the Invention

The present invention relates generally to the field of psychotic disorders, such as schizophrenia and bipolar disorders. More particularly, it concerns genetic markers of antipsychotic response, for example, genes and genetic markers that influence or predict a person's likely response to antipsychotic medications.

2. Description of Related Art

Numerous drugs exist to treat psychotic disorders, such as schizophrenia (SZ), related SZ-spectrum disorders (including schizotypal personality disorder (SPD) and schizoaffective disorder (SD)), and bipolar disorders (BD). Most of these drugs fall into one of two categories, typical (first generation) and atypical (second generation).

Although head to head studies of large groups of patients, either in the acute phase or outpatient treatment, show that most atypical antipsychotic drugs are equally efficacious for positive symptoms, there are individual differences in response to specific drugs based on differences in drug pharmacology and metabolism, combined with genetic differences between patients. There are currently no proven ways to identify which antipsychotic drug is optimal for a given patient. Thus, patients switch from one drug to another when response is not considered to be adequate or side effects are intolerable. This switching of medication incurs a variety of increased costs, both economic and patient and caregiver hardship. On average, each patient may change medications three times before finding one that works. Additionally, the current drugs have significant side-effects. This combination of side-effects and limited efficacy create a vast unmet need for selecting the optimal antipsychotic for each patient.

Moreover, the limited or partial response that is often seen with antipsychotics leads to polypharmacy, where physicians prescribe two or more antipsychotic drugs plus mood stabilizers and/or antidepressants. Polypharmacy increases medication costs and significantly increases the likelihood of adverse advents and drug interactions (Stahl and Grady, 2006).

Pharmacogenomics, using genetic variation to predict altered response and side-effects profiles, will be important for enhanced patient care going forward. There continues to exist, therefore, a need to identify specific genetic variations that are associated with treatment outcomes for psychotic disorders.

SUMMARY OF THE INVENTION

The invention is in part based on the finding that a particular haplotype, which the inventors refer to as the SULT4A1-1 haplotype, is a biomarker that can be used for selecting a more appropriate antipsychotic treatment plan for a particular subject. For example, the inventors have discovered that patients that have a SULT4A1-1 haplotype respond better when treated with olanzapine than SULT4A1-1 positive patients treated with risperidone, and respond better than SULT4A1-1 negative patients treated with olanzapine. Similarly, the inventors have discovered that patients that have a SULT4A1-1 haplotype respond better when treated with quetiapine than SULT4A1-1 negative patients treated with quetiapine. Further, the inventors have discovered that patients that do not have a SULT4A1-1 haplotype respond better when treated with risperidone than SULT4A1-1 positive patients treated with risperidone. Thus, prior determination of a patient's SULT4A1-1 haplotype status can aid in the development of an optimal antipsychotic treatment regimen.

Thus, an aspect of the invention involves determining whether genetic material of the subject comprises a SULT4A1-1 haplotype. Of course, to meet the need to transfer and store genetic information, the results of the determination will preferably be recorded and maintained in a tangible medium, such as a computer-readable disk, a solid state memory device, an optical storage device or the like, more specifically, a storage device such as a hard drive, a Compact Disk (CD) drive, a floppy disk drive, a tape drive, a random access memory (RAM), etc.

One preferred manner of obtaining the genetic haplotype information involves analyzing the genetic material of the subject to determine the presence or absence of the SULT4A1-1 haplotype. This can be accomplished, for example, by testing the subject's genetic material through the use of a biological sample. In certain embodiments, the methods set forth will thus involve obtaining a biological sample from the subject and testing the biological sample to identify whether a SULT4A1-1 haplotype is present. The biological sample may be any biological material that contains DNA or RNA of the subject, such as a nucleated cell source. Non-limiting examples of cell sources available in clinical practice include hair, skin, nucleated blood cells, buccal cells, any cells present in tissue obtained by biopsy or any other cell collection method. The biological sample may also be obtained from body fluids, including without limitation blood, saliva, sweat, urine, amniotic fluid (the fluid that surrounds a fetus during pregnancy), cerebrospinal fluid, feces, and tissue exudates. DNA may be extracted from the biologic sample such as the cell source or body fluid using any of the numerous methods that are standard in the art.

Determining whether the genetic material exhibits a SULT4A1-1 haplotype polymorphism can be by any method known to those of ordinary skill in the art, such as genotyping (e.g., SNP genotyping) or sequencing. Techniques that may be involved in this determination are well-known to those of ordinary skill in the art. Examples of such techniques include allele specific oligonucleotide hybridization, size analysis, sequencing, hybridization, 5' nuclease digestion, single-stranded conformation polymorphism analysis, allele specific hybridization, primer specific extension, and oligonucleotide ligation assays. Additional information regarding these techniques is discussed in the specification below.

For haplotype determinations, the sequence of the extracted nucleic acid of the subject may be determined by any means known in the art, including but not limited to direct sequencing, hybridization with allele-specific oligonucleotides, allele-specific PCR, ligase-PCR, HOT cleavage, denaturing gradient gel electrophoresis (DDGE), and single-stranded conformational polymorphism (SSCP) analysis. Direct sequencing may be accomplished by any method, including without limitation chemical sequencing, using the Maxam-Gilbert method, by enzymatic sequencing, using the Sanger method, mass spectrometry sequencing, and sequencing using a chip-based technology. In particular embodiments, DNA from a subject is first subjected to amplification by polymerase chain reaction (PCR) using specific amplification primers. In some embodiments, the method further involves amplification of a nucleic acid from the biological sample. The amplification may or may not involve PCR. In some embodiments, the primers are located on a chip.

In specific embodiments, the subject is a human. For example, in some embodiments the human is a subject who has, is suspected to have, or is at risk of a psychotic disorder, such as schizophrenia, schizotypal personality disorder (SPD), schizoaffective disorder (SD), or bipolar disorder (BD). In one embodiment, the subject is a patient having previously diagnosed a psychotic disorder (e.g., a patient suffering from early, intermediate or aggressive psychotic disorder). In some embodiments, the subject is of Caucasian (CA) descent, i.e., has one or more ancestors who are CA.

Moreover, the inventors contemplate that the genetic structure and sequence, including SNP profiles, of individual subjects will at some point be widely or generally available, or will have been developed by an unrelated third party. In such instances, there will be no need to test or analyze the subject's biological material again. Instead, the genetic information will in such cases be obtained simply by analyzing the sequencing or genotyping outcome of the subject, for example, a SNP profile, a whole or partial genome sequence, etc. These outcome can then be obtained from or reported by a sequencing or a genotyping service, a laboratory, a scientist, or any genetic test platforms.

In some further aspects, the method may further comprise reporting the determination to the subject, a health care payer, an attending clinician, a pharmacist, a pharmacy benefits manager, or any person that the determination may be of interest.

In certain embodiments, there is also provided a method of developing a pharmacotherapeutic treatment plan for a subject having or suspected of having a psychotic disorder comprising determining the SULT4A1-1 haplotype status of the patient, wherein a) if the subject comprises a SULT4A1-1 haplotype, the subject is more likely to exhibit a favorable response to olanzapine; and b) if the subject does not comprise a SULT4A1-1 haplotype, the subject is less likely to exhibit a favorable response to olanzapine; and developing the pharmacotherapeutic treatment plan. For example, if the subject comprises a SULT4A1-1 haplotype, then the method may further comprise treating the subject with olanzapine. If the subject does not comprise the SULT4A1-1 haplotype, then the method may further comprise treating the subject with an anti-psychotic treatment other than olanzapine, such as treating with risperidone, or perphenazine.

In certain embodiments, there is also provided a method of determining elevated risk of a patient to discontinue treatment with olanzapine due to a treatment-emergent adverse event, comprising determining the SULT4A1-1 haplotype in a patient sample, wherein a) if the human subject comprises the SULT4A1-1 haplotype, the subject is more likely to exhibit a propensity to continue treatment; and b) if the subject does not comprise the SUTL4A1-1 haplotype, the subject is more likely to exhibit a propensity to discontinue treatment due to a treatment-emergent adverse event.

In certain embodiments, there is also provided a method of selecting a pharmacotherapeutic treatment plan for a human subject having the potential to experience a treatment-emergent adverse event when treated with olanzapine, comprising determining the SULT4A1-1 haplotype in a sample, wherein a) if the human subject does not comprise the SULT4A1-1 haplotype the subject is more likely to experience a treatment-emergent adverse event when treated with olanzapine; and b) if the subject comprises the SUTL4A1-1 haplotype the subject is not more likely to experience a treatment-emergent adverse event when treated with olanzapine; selecting a pharmacotherapeutic treatment plan based on the SULT4A1-1 haplotype; and treating the subject with the selected pharmacotherapeutic treatment.

Certain aspects of the invention may involve a method for treating a subject having a psychotic disorder and determined to have a SULT4A1-1 haplotype, comprising treating the subject with olanzapine. In some further aspects, the invention may include a method for treating a subject having a psychotic disorder and determined not to have a SULT4A1-1 haplotype, comprising treating the subject with a non-olanzapine anti-psychotic treatment, such as treating with risperidone, ziprasidone, or perphenazine. In certain embodiments, the psychotic disorder is schizophrenia.

In other embodiments, there is provided a method for determining response to treatment with risperidone for a human subject having or suspected of having schizophrenia comprising determining the SULT4A1-1 haplotype in a sample, wherein a) if the human subject comprises the SULT4A1-1 haplotype, the subject is less likely to exhibit a favorable response to risperidone; and b) if the subject does not comprise the SUTL4A1-1 haplotype, the subject is more likely to exhibit a favorable response to risperidone.

In other embodiments, there is provided a method for determining elevated risk of a patient to discontinue treatment with risperidone due to a treatment-emergent adverse event or lack of efficacy comprising determining the SULT4A1-1 haplotype in a sample, wherein a) if the human subject comprises the SULT4A1-1 haplotype, the subject is more likely to exhibit a propensity to discontinue treatment due to a treatment-emergent adverse event or lack of efficacy; and b) if the subject does not comprise the SULT4A1-1 haplotype, the subject is more likely to exhibit a propensity to continue treatment.

In certain embodiments, there is also provided a method for selecting a pharmacotherapeutic treatment plan for a human subject having the potential for suffering a treatment-emergent adverse event or lack of efficacy when treated with risperidone, comprising determining the SULT4A1-1 haplotype in a sample, wherein a) if the human subject comprises the SULT4A1-1 haplotype, the subject is more likely to experience a treatment-emergent adverse event or lack of efficacy when treated with risperidone; and b) if the subject does not comprise the SUTL4A1-1 haplotype, the subject is not more likely to experience a treatment-emergent adverse event or lack of efficacy when treated with risperidone; selecting a pharmacotherapeutic treatment plan based on the SULT4A1-1 haplotype; and treating the subject with the selected pharmacotherapeutic treatment.

Certain aspects of the invention may involve a method for treating a subject having a psychotic disorder and determined to not have the SULT4A1-1 haplotype, comprising treating the subject with risperidone. In some further aspects, the invention may include a method for treating a subject having a psychotic disorder and determined to have a SULT4A1-1 haplotype, comprising treating the subject with a non-risperidone anti-psychotic treatment such as treating with olanzapine, quetiapine, ziprasidone, or perphenazine. In certain embodiments, the psychotic disorder is schizophrenia.

In other embodiments, there is provided a method for determining response to treatment with quetiapine for a human subject having or suspected of having schizophrenia comprising determining the SULT4A1-1 haplotype in a sample, wherein if the human subject comprises the SULT4A1-1 haplotype the subject is more likely to exhibit a favorable response to quetiapine and if the subject does not comprise the SULT4A1-1 haplotype the subject is less likely to exhibit a favorable response to quetiapine.

In certain embodiments, there is also provided a method for treating a human subject having or suspected of having a psychotic disorder comprising a) selecting a subject that has been determined to have a SULT4A1-1 haplotype, defined as a haplotype comprising a C allele at rs763120, a combination of an A allele at rs2285162 and a G allele at rs2285167, or the combination of a T allele atrs2285166 and G allele at rs2285167, and treating the subject with quetiapine or olanzapine; or b) selecting a subject that has been determined not to have the SULT4A1-1 haplotype and treating the subject with an anti-psychotic treatment other than quetiapine or olanzapine.

Certain aspects of the invention may involve a method for treating a subject having a psychotic disorder and determined to have a SULT4A1-1 haplotype, comprising treating the subject with quetiapine or olanzapine. In some further aspects, the invention may include a method for treating a subject having a psychotic disorder and determined not to have a SULT4A1-1 haplotype, comprising treating the subject with a an anti-psychotic treatment other than quetiapine or olanzapine, such as treating with risperidone, ziprasidone, or perphenazine. In certain embodiments, the psychotic disorder is schizophrenia.

Certain aspects of the invention may involve a method for treating a subject comprising selecting a subject that is determined to have a SULT4A1-1 haplotype and developing an appropriate treatment plan. Other aspects of the invention may involve a method for treating a subject comprising selecting a subject that is determined not to have a SULT4A1-1 haplotype and developing an appropriate treatment plan. Prior determination of a patient's SULT4A1-1 haplotype status may be obtained from or reported by a sequencing or a genotyping service, a laboratory, a scientist, or any genetic test platforms.

The SULT4A1-1 haplotype characterization may also apply to diagnosis and prognosis of psychotic disorders. For example, there may be provided a method of assessing the severity of such a disorder, comprising obtaining genetic information about the subject by the methods disclosed above, wherein if the subject comprises a SULT4A1-1 haplotype, the subject is at a higher risk for having a more severe disorder, and wherein if the subject does not comprise the SULT4A1-1 haplotype, the subject is at a lower risk for having a more severe disorder. The assessment may be stored in a tangible medium, such as a computer-readable disk, a solid state memory device, and an optical storage device.

Certain aspects of the present invention also contemplate the preparation of kits or arrays for use in accordance with the present invention. Suitable kits include various reagents for use in accordance with the present invention in suitable containers and packaging materials, including tubes, vials, and shrink-wrapped and blow-molded packages. Such an array or a kit may comprise a plurality of primers or probes specific for a SULT4A1-1 haplotype. The array may be a genotyping chip. Also a tangible, computer-readable medium comprising a SNP profile of a subject may also be provided, wherein the SNP profile exhibits the presence or absence of a SULT4A1-1 haplotype.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
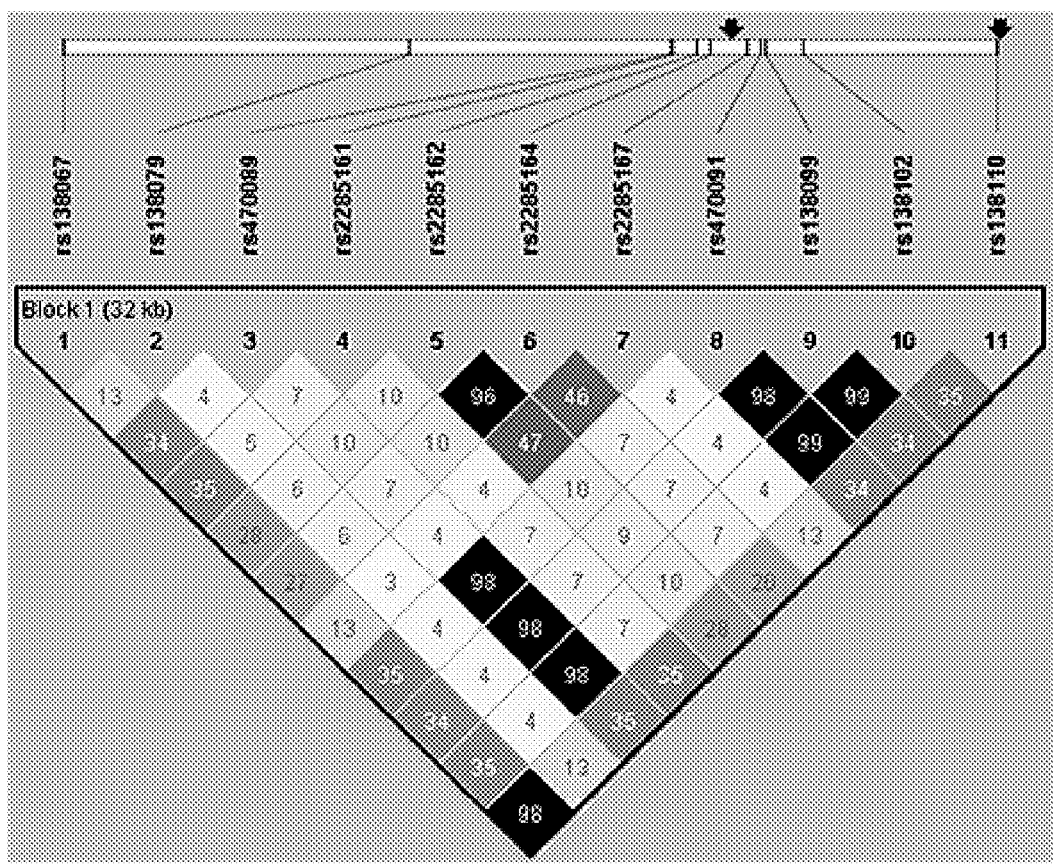
FIG. 1: Linkage disequilibrium for the Caucasian sample. The Haploview output shows pairwise correlation coefficients ($r^2$ values in % are given in the diamonds) for the 11 SULT4A1 SNPs from the CATIE study (N=836 persons). Based on the total sample of cases and controls, Haploview identifies a single haplotype block for the 11 SNPs (Barrett et al., 2005). The locations of previously studied SNPs, rs138097 (the SNP is in position 31 of SEQ ID NO:8) and rs138110 (the SNP is in position 31 of SEQ ID NO:13), are indicated by arrows. Only the latter was included in the CATIE study. Previously studied marker rs138060 (the SNP is in position 31 of SEQ ID NO:1) is located approximately 5 kb to the left of rs138067 (the SNP is in position 31 of SEQ ID NO:2), outside the region covered by the SULT4A1 SNPs in CATIE.

Choosing the correct antipsychotic medication for patients suffering from severe neuropsychiatric illnesses is a major challenge. Fewer than one in three patients suffering from schizophrenia and related disorders will have a robust improvement in symptoms on the first antipsychotic drug prescribed. One out of three patients will be resistant to commonly used drugs. Furthermore, the metabolic side-effects of antipsychotic drugs, most commonly seen with olanzapine and clozapine, result in low compliance, with 50% of patients discontinuing drug use within 6 months of prescription, leading to relapse (return of psychosis) and hospitalization.

Therefore, methods and compositions of the present invention will help to meet this challenge by assisting physicians, patients, lab, or pharmacists with selection or recommendation of appropriate antipsychotic medication. Specifically, the present inventors have used a specific haplotype of the SULT4A1 gene for pharmacogenomic applications in related psychotic disorders, i.e., assessing the impact of genetic variation on drug response and side-effect profiles.

Examples of variation in drug response include any of the following: efficacy, side-effect profile, treatment maintenance and discontinuation rates, return to work status, hospitalizations, suicidality, total healthcare cost, social functioning scales, response to non-pharmacological treatments, and dose response curves. Efficacy includes but is not limited to the following definition: >=20 decrease in Total PANSS score. Side-effect profile includes one or more of weight gain, metabolic dysfunction, lipid dysfunction, movement disorders, and extrapyramidal symptoms.

Further embodiments and advantages of the invention are described below.

I. Definitions

As defined herein, "Schizophrenia" or "SZ" includes the SZ-spectrum disorders, Schizotypal Personality Disorder (SPD) and Schizoaffective Disorder (SD), as well as Schizophrenia under the narrower, DSM-IV definition.

As used herein, a "haplotype" is one or a set of markers (e.g., polymorphisms) that are grouped closely together on a given chromosome and are usually inherited as a group. As used herein, the term "polymorphism" refers to the condition in which there is a variation in the DNA sequence between some members of a species. A haplotype can include, but not be limited to, a variety of genetic markers, including indels (insertions or deletions of the DNA at particular locations on the chromosome); single nucleotide polymorphisms (SNPs) in which a particular nucleotide is changed; microsatellites; and minisatellites.

As used herein, a "SULT4A1-1 haplotype," i.e., a "SULT4A1-1 positive haplotype," refers to a haplotype comprising rs763120(C) (a C allele in position 31 of SEQ ID NO:15), a combination of rs2285162(an A allele at position 31 of SEQ ID NO:6)-rs2285167(a G allele at position 31 of SEQ ID NO:9), a combination of rs2285166(a T allele at position 31 of SEQ ID NO:14)-rs2285167(G), or a haplotype that is in complete linkage disequilibrium with the combination rs2285162(A)-rs2285167(G) or rs2285166(T)-rs2285167(G), such as a haplotype comprising rs763120 (a C allele at position 31 of SEQ ID NO:15). The sequence identifiers are intended for SNP sequence identification only and an ordinary person of skill in the art would recognize some subjects may have sequence heterogeneity or polymorphism at other positions of those sequences.

"Linkage disequilibrium" occurs when the observed frequencies of associations of alleles for different polymorphisms in a population do not agree with frequencies predicted by multiplying together the allele frequencies for the individual genetic markers, thus resulting in a specific haplotype in the population.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target. The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al. (2003). Aqueous and nonaqueous methods are described in that reference and either can be used. Hybridization conditions may be a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30%, e.g., at least 40%, 50%, 60%, 70%, 80%, 90% or 100%, of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80%, e.g., 85%, 90%, 95%, 97% or more, identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

As used herein, the term "stratification" refers to the creation of a distinction between subjects on the basis of a characteristic or characteristics of the subjects. Generally, in the context of clinical trials, the distinction is used to distinguish responses or effects in different sets of patients distinguished according to the stratification parameters. In some embodiments, stratification includes distinction of subject groups based on the presence or absence of a SULT4A1-1 haplotype described herein. The stratification can be performed, e.g., in the course of analysis, or can be used in creation of distinct groups or in other ways.

As used herein, "Typical" antipsychotics refer to so called first generation or classical antipsychotics. This class of drugs was first developed in the 1950s. Some examples include: Chlorpromazine (Largactil, Thorazine), Fluphenazine (Prolixin), Haloperidol (Haldol, Serenace), Molindone, Thiothixene (Navane), Thioridazine (Mellaril), Trifluoperazine (Stelazine), Loxapine (Loxapac, Loxitane), Perphenazine, Prochlorperazine (Compazine, Buccastem, Stemetil), Pimozide (Orap), Zuclopenthixol (Clopixol). This class of drug can cause serious adverse events, particularly Tardive Dyskinesia, a movement disorder.

As used herein, "Atypical" antipsychotics refer to a newer class of antipsychotic drugs first introduced in the 1990s. This class of drugs includes the following examples:

Clozapine (Clozaril) (FDA-approval: 1990): Available in oral tablets and dissolving tablets (FazaClo).

Risperidone (Risperdal) (FDA-approval: 1993): Available in oral tablets, dissolving tablets, liquid form, and extended release intramusclar injection.

Olanzapine (Zyprexa) (FDA-approval: 1996): Available in oral tablets, dissolving tablets, and intramuscular injection.

Quetiapine (Seroquel) (FDA-approval: 1997): Available only in oral tablets.

Ziprasidone (Geodon) (FDA-approval: 2001): Available in oral capsules and intramuscular injection.

Aripiprazole (Abilify) (FDA-approval: 2002): Available in oral tablets and dissolving tablets.

Paliperidone (Invega) (FDA-approval: 2006): Available in extended-release oral tablets.

Asenapine (Saphris) (FDA-approval: 2009): Available in sublingual tablets.

Lurasidone (Latuda) (FDA-approval: 2010): Available in oral tablets.

Iloperidone (Fanapta or Zomaril): FDA has accepted NDA as of Nov. 27, 2007.

Sertindole (Serlect) (Not approved by the FDA for use in the USA).

Zotepine (Not approved by the FDA for use in the USA).

Amisulpride (Not approved by the FDA for use in the USA).

Bifeprunox (Not approved by the FDA for use in the USA).

Melperone: Approved in Europe. Currently in clinical trials in the USA.

Atypicals have a superior side-effect profile for the serious adverse event Tardive Dyskinesia. However, the atypicals can cause metabolic disturbances leading to weight gain and metabolic syndrome.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

II. SULT4A1-1 Haplotype

In certain aspects, the present invention involves determination of a SULT4A1-1 haplotype and use of the specific haplotype to optimize treatments for psychotic disorders. For example, the invention may enhance drug safety and improve treatment outcome.

The sulfotransferase-4A1 (SULT4A1) gene encodes the major cytoplasmic sulfotransferase in the central nervous system and is believed to be involved in neurotransmitter metabolism and function (Iali-Hassani et al., 2007; Liyou et al., 2003; Minchin et al., 2008). Certain alleles of the gene are over-transmitted to offspring with schizophrenia in families having multiple affected individuals (Brennan and Condra, 2005), and genotypes for SNPs in this gene are associated with psychopathology and cognition in patients suffering from schizophrenia and schizoaffective disorder (Meltzer et al., 2008).

The inventors used samples from the Clinical Antipsychotic Trials of Intervention Effectiveness (CATIE), a large federally funded clinical trial designed to assess the efficacy of antipsychotics in a real world setting (Lieberman et al., 2005; Stroup et al., 2003), to identify common variants of the SULT4A1 gene relating to elevated levels of baseline psychopathology and to explore gene-based differential responses of patients suffering from schizophrenia and related disorders (schizoaffective disorder and bipolar disorder) to atypical antipsychotic drugs.

A commonly occurring variation in the SULT4A1 gene correlated with atypical antipsychotic response was characterized. Specifically, the SULT4A1-1 haplotype can be tagged by two single nucleotide polymorphisms (SNPs): the rs2285167 (G) allele in combination with either the rs2285162(A) allele or the rs2285166(T). Since the latter two SNPs are in complete linkage disequilibrium, they can be used interchangeably. Alternatively, the SULT4A1-1 haplotype can be tagged by any SNPs or SNP combinations which are exchangeable with these two-SNP combinations, such as a single SNP rs763120 (C).

The SULT4A1-1 haplotype was also selected as the biomarker of interest based on results showing associations between this haplotype and disease severity. The SULT4A1-1 haplotype occurs at a frequency of approximately 11.7% in Caucasians and is found at expected levels based on Hardy-Weinberg predictions, such that approximately 23% of patients carry it.

III. Haplotype Determination

The invention includes methods for determination of SULT4A1 haplotypes in order to select optimal treatments. One or more markers, such as SNPs within SULT4A1 gene (exemplary SNPs like rs2285162(A), rs2285166(T), rs2285167(G), and rs763120 (C)), can be used to determine a SULT4A1-1 haplotype as defined above. Using the exemplary SNP markers or SNPs in complete linkage disequilibrium with the exemplary SNPs, one can determine the haplotype. Using these haplotypes, one can assign subjects to specific categories based on the evaluation of haplotypes present in the subject and select optimal treatments (atypical antipsychotic, typical antipsychotic, and/or psychosocial intervention) for patients.

Determining a haplotype can, but need not, include obtaining a sample comprising DNA from a subject, and/or assessing the identity, presence or absence of one or more genetic markers for the SULT4A1-1 haplotype in the sample. The individual or organization who determines the haplotype need not actually carry out the physical analysis of a sample from a subject; the haplotype can include information obtained by analysis of the sample by a third party. Thus the methods can include steps that occur at more than one site. For example, a sample can be obtained from a subject at a first site, such as at a health care provider or at the subject's home in the case of a self-testing kit. The sample can be analyzed at the same or a second site, e.g., at a laboratory, a sequencing or genotyping facility, or other testing facility. Determining a haplotype can also include or consist of reviewing a subject's medical history or test results, where the medical history or test results includes information regarding the identity, presence or absence of one or more genetic markers in the subject.

Samples that are suitable for use in the methods described herein contain genetic material, e.g., genomic DNA (gDNA). Non-limiting examples of sources of samples include urine, blood, cells, and tissues. The sample itself will typically consist of nucleated cells (e.g., blood or buccal cells), tissue, etc., removed from the subject. The subject can be an adult, a child, a fetus, or an embryo. In some embodiments, the sample is obtained prenatally, either from a fetus or an embryo or from the mother (e.g., from fetal or embryonic cells in the maternal circulation). Methods and reagents are known in the art for obtaining, processing, and/or analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

The sample may be further processed before the detecting step. For example, DNA in a cell or tissue sample can be separated from other components of the sample. The sample can be concentrated and/or purified to isolate DNA. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. All samples obtained from a subject, including those subjected to any sort of further processing, are considered to be obtained from the subject.

SULT4A1-1 haplotype may be determined by any methods known in the art, e.g., gel electrophoresis, capillary electrophoresis, size exclusion chromatography, sequencing, and/or arrays to detect the presence or absence of the marker(s) of the haplotype. Amplification of nucleic acids, where desirable, can be accomplished using methods known in the art, e.g., PCR.

Methods of nucleic acid analysis to detect polymorphisms and/or polymorphic variants include, e.g., microarray analysis. Hybridization methods, such as Southern analysis, or fluorescent intensity analysis of microarrays, can also be used (see Ausubel et al., 2003; Redon et al., 2006).

Other methods include direct manual sequencing (Church and Gilbert, 1988; Sanger et al., 1977; U.S. Pat. No. 5,288, 644); automated fluorescent sequencing; single-stranded conformation polymorphism assays (SSCP); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., 1989); mobility shift analysis (Orita et al., 1989); restriction enzyme analysis (Flavell et al., 1978; Geever et al., 1981); quantitative real-time PCR (Raca et al., 2004); heteroduplex analysis; chemical mismatch cleavage (CMC) (Cotton et al., 1985); RNase protection assays (Myers et al., 1985); use of polypeptides that recognize nucleotide mismatches, e.g., E. coli mutS protein; allele-specific PCR. See, e.g., U.S. Patent Publication No. 2004/0014095, to Gerber et al., which is incorporated herein by reference in its entirety. In some embodiments, the sequence is determined on both strands of DNA.

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. See e.g., PCR Primer: A Laboratory Manual; McPherson et al., 2000; Mattila et al., 1991; Eckert et al., 1991; and U.S. Pat. No. 4,683,202. Other amplification methods that may be employed include the ligase chain reaction (LCR) (Wu and Wallace, 1989, Landegren et al., 1988), transcription amplification (Kwoh et al., 1989), self-sustained sequence replication (Guatelli et al., 1990), and nucleic acid based sequence amplification (NASBA). Guidelines for selecting primers for PCR amplification are well known in the art. See, e.g., McPherson et al. (2000). A variety of computer programs for designing primers are available, e.g., "Oligo" (National Biosciences, Inc, Plymouth Minn.), MacVector (Kodak/IBI), and the GCG suite of sequence analysis programs (Genetics Computer Group, Madison, Wis. 53711).

In one example, a sample (e.g., a sample comprising genomic DNA), is obtained from a subject. The DNA in the sample is then examined to determine a SULT4A1-1 haplotype as described herein. The haplotype can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., 1994). The PNA probe can be designed to specifically hybridize to a nucleic acid comprising a polymorphic variant of the SULT4A1-1 haplotype.

In some embodiments, restriction digest analysis can be used to detect the existence of a polymorphic variant of a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see Ausubel et al., supra). The digestion pattern of the relevant DNA fragment may indicate the presence or absence of a particular polymorphic variant of the SULT4A1 polymorphism and may be therefore indicative of the presence or absence of the SULT4A1-1 haplotype.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

DNA containing the amplified portion may be dot-blotted, using standard methods (see Ausubel et al., supra), and the blot contacted with the oligonucleotide probe. The presence of specific hybridization of the probe to the DNA is then detected. Specific hybridization of an allele-specific oligonucleotide probe (specific for a polymorphic variant indicative of susceptibility to altered pharmacological response or endophenotype) to DNA from the subject may determine a SULT4A1-1 haplotype.

Allele-specific oligonucleotides can be used to detect the presence of a polymorphic variant, e.g., through the use of dot-blot hybridization of amplified oligonucleotides with allele-specific oligonucleotide (ASO) probes (see, for example, Saiki et al., 1986). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism. An allele-specific oligonucleotide probe that is specific for a particular polymorphism can be prepared using standard methods (see Ausubel et al., supra).

In some embodiments, fluorescence polarization template-directed dye-terminator incorporation (FP-TDI) is used to determine which of multiple polymorphic variants of a polymorphism is present in a subject (Chen et al., 1999). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., 2000). Additional methods include, for example, PCR amplification in combination with denaturing high performance liquid chromatography (dHPLC) (Underhill et al., 1997).

The methods can include determining the genotype of a subject with respect to both copies of the polymorphic site present in the genome. For example, the complete genotype may be characterized as −/−, as +/+, or as +/+, where a plus sign indicates the presence of the polymorphic variant of interest, such as rs2285162(A), rs2285166(T), or rs2285167 (G), and a minus sign indicates the absence of the polymorphic variant of interest and/or the presence of the other or wild type sequence at the polymorphic site. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to certain embodiments of the invention.

IV. Psychotic Disorders

Certain aspects of the invention involve using the SULT4A1-1 haplotype status to optimize treatments for psychotic disorders, such as schizophrenia (SZ), schizotypal personality disorder (SPD), schizoaffective disorder (SD), and/or bipolar disorders (BD).

Schizophrenia and bipolar disorder are life-long, severely disabling mental illnesses. The clinical criteria for these neuropsychiatric illnesses have continued to evolve through a consensus process organized by the American Psychiatric Association (APA) and published in its Diagnostic and Statistical Manual (DSM) I-IV (American Psychiatric Assoc. Diagostic and Statistical Manual of Mental Disorders, 1994). The inventors disclose here some of the key features of both illnesses as currently conceived, with the full awareness that there is strong evidence for overlap between these disorders in genetic risk factors and response to treatment. Nevertheless, all indications are that DSM-V, which is currently being developed by the APA, will maintain this distinction more or less in the current form. Also because FDA indications for treatment have been and may continue to be given for drugs for each disorder separately, having genetic information which pertains to classification and prediction of response to treatment is of considerable value.

Schizophrenia and bipolar disorder share some common clinical features while differing on others. Schizophrenia is characterized by psychotic symptoms (delusions, hallucinations), disorganized thinking and cognitive impairment and poor social and work function. Additionally, some schizophrenia patients can have severe negative symptoms, including blunted affect and social and emotional withdrawal. Bipolar Disorder is characterized by two main types of mood disturbances, with depression being the most common type and mania, or hypomania less frequent. Psychotic disorders may be present in either the manic or depressive mood phases. Both disorders have a high risk for suicide attempts and completions.

Schizophrenia usually begins in the late teens and early 20's. It affects about 1% of the population. Conversely, bipolar disorder most often occurs in the $3^{rd}$ and $4^{th}$ decades of life. Bipolar (BP) Type I affects about 1.5% of the population. BP type II and BP Not Otherwise Specified (NOS) afflict another 2-4% of the population. Life-long drug treatment is often required to minimize the number of acute episodes, the need for hospitalization or assisted living, and to optimize daily functioning. Suicide occurs in 5% of schizophrenia cases and 10% of bipolar disorder cases. Patients with schizophrenia or bipolar disorder can have "acute" episodes which are characterized by abrupt and large increases in psychotic symptoms. Often, these episodes occur after a period of non-compliance with medication. Both are generally treated with one or more classes of psychotropic medications. Atypical antipsychotic drugs treat psychosis and mood disturbances. Additionally, mood stabilizers such as lithium or valproate treat the manic phase of bipolar disorder, and antidepressants and atypical antipsychotic drugs target the depressive phase. Antipsychotics and mood stabilizers are often used together for "maintenance" treatment to prevent relapse.

A. Schizophrenia (SZ)

SZ is considered a clinical syndrome, and is probably a constellation of several pathologies. Substantial heterogeneity is seen between cases; this is thought to reflect multiple overlapping etiologic factors, including both genetic and environmental contributions. A diagnosis of SZ is typically indicated by chronic psychotic symptoms, e.g., hallucinations and delusions. Disorganization of thought and behavior are common and are considered distinguishing factors in the diagnosis of SZ. Patients typically have some subtle impairments in cognition. Reduced emotional experience and expression, low drive, and impaired speech are observed in a subgroup of patients. Cognitive, emotional and social impairments often appear early in life, while the psychotic symptoms typically manifest in late adolescence or early adulthood in men, a little later in women.

A diagnosis of SZ can be made according to the criteria reported in the *Diagnostic and Statistical Manual of Mental Disorders, Fourth Edition, Text Revision*, American Psychiatric Association, 2000 (referred to herein as DSM-IV) as follows:

Diagnostic Criteria for SZ—All six criteria must be met for a diagnosis of SZ.

A. Characteristic symptoms: Two (or more) of the following, each present for a significant portion of time during a one month period (or less if successfully treated):

(1) delusions; (2) hallucinations; (3) disorganized speech (e.g., frequent derailment or incoherence); (4) grossly disorganized or catatonic behavior; (5) negative symptoms, e.g., affective flattening, alogia, or avolition.

Only one criterion A symptom is required if delusions are bizarre or hallucinations consist of a voice keeping up a running commentary on the person's behavior or thoughts, or two or more voices conversing with each other.

B. Social/occupational dysfunction: For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration: Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

D. Schizoaffective and Mood Disorder Exclusion: Schizoaffective Disorder and Mood Disorder With Psychotic Features have been ruled out because either (1) no major depressive, manic, or mixed episodes have occurred concurrently with the active-phase symptoms; or (2) if mood episodes have occurred during active-phase symptoms, their total duration has been brief relative to the duration of the active and residual periods.

E. Substance/General Medical Condition Exclusion: The disturbance is not due to the direct physiological effects of a substance (e.g., a drug of abuse, a medication) or a general medical condition.

F. Relationship to a Pervasive Developmental Disorder: If the patient has a history of Autistic Disorder or another Pervasive Developmental Disorder, the additional diagnosis of SZ is made only if prominent delusions or hallucinations are also present for at least a month (or less if successfully treated).

B. Schizoaffective Disorder (SD)

SD is characterized by the presence of affective (depressive or manic) symptoms and schizophrenic symptoms within the same, uninterrupted episode of illness.

The DSM-IV Criteria for a diagnosis of schizoaffective disorder is as follows:

An uninterrupted period of illness during which, at some time, there is either (1) a Major Depressive Episode (which must include depressed mood), (2) a Manic Episode, or (3) a Mixed Episode, concurrent with symptoms that meet (4) Criterion A for SZ, above.

A. Criteria for Major Depressive Episode

At least five of the following symptoms must be present during the same 2-week period and represent a change from previous functioning; at least one of the symptoms is either (1) depressed mood or (2) loss of interest or pleasure.

(1) depressed mood most of the day, nearly every day, as indicated by either subjective report (e.g., feels sad or empty) or observation made by others (e.g., appears tearful). In children and adolescents, this can be an irritable mood.

(2) markedly diminished interest or pleasure in all, or almost all, activities most of the day, nearly every day (as indicated by either subjective account or observation made by others)

(3) significant weight loss when not dieting or weight gain (e.g., a change of more than 5% of body weight in a month), or decrease or increase in appetite nearly every day. (In children, failure to make expected weight gains is considered).

(4) insomnia or hypersomnia nearly every day (5) psychomotor agitation or retardation nearly every day (observable by others, not merely subjective feelings of restlessness or being slowed down)

(6) fatigue or loss of energy nearly every day (7) feelings of worthlessness or excessive or inappropriate guilt (which may be delusional) nearly every day (not merely self-reproach or guilt about being sick)

(8) diminished ability to think or concentrate, or indecisiveness, nearly every day
(either by subjective account or as observed by others)

(9) recurrent thoughts of death (not just fear of dying), recurrent suicidal ideation without a specific plan, or a suicide attempt or a specific plan for committing suicide In addition, the symptoms do not meet criteria for a Mixed Episode. The symptoms cause clinically significant distress or impairment in social, occupational, or other important areas of functioning. The symptoms are not due to the direct physiological effects of a substance (e.g., a drug of abuse, a medication) or a general medical condition (e.g., hypothyroidism).

The symptoms are not better accounted for by Bereavement, i.e., after the loss of a loved one, the symptoms persist for longer than 2 months, or are characterized by marked functional impairment, morbid preoccupation with worthlessness, suicidal ideation, psychotic symptoms, or psychomotor retardation.

B. Criteria for Manic Episode

A manic episode is a distinct period of abnormally and persistently elevated, expansive, or irritable mood, lasting at least one week (or any duration, if hospitalization is necessary).

During the period of mood disturbance, three (or more) of the following symptoms have persisted (four if the mood is only irritable) and have been present to a significant degree:

(1) inflated self-esteem or grandiosity (2) decreased need for sleep (e.g., feels rested after only 3 hours of sleep)

(3) more talkative than usual or pressure to keep talking (4) flight of ideas or subjective experience that thoughts are racing (5) distractibility (i.e., attention too easily drawn to unimportant or irrelevant external stimuli)

(6) increase in goal-directed activity (either socially, at work or school, or sexually) or psychomotor agitation (7) excessive involvement in pleasurable activities that have a high potential for painful consequences (e.g., engaging in unrestrained buying sprees, sexual indiscretions, or foolish business investments)

The symptoms do not meet criteria for a Mixed Episode. The mood disturbance is sufficiently severe to cause marked impairment in occupational functioning or in usual social activities or relationships with others, or to necessitate hospitalization to prevent harm to self or others, or there are psychotic features. The symptoms are not due to the direct physiological effects of a substance (e.g., a drug of abuse, a medication, or other treatment) or a general medical condition (e.g., hyperthyroidism).

C. Criteria for Mixed Episode

A mixed episode occurs when the criteria are met both for a Manic Episode and for a Major Depressive Episode (except for duration) nearly every day during at least a 1-week period. The mood disturbance is sufficiently severe to cause marked impairment in occupational functioning or in usual social activities or relationships with others, or to necessitate hospitalization to prevent harm to self or others, or there are psychotic features.

The symptoms are not due to the direct physiological effects of a substance (e.g., a drug of abuse, a medication, or other treatment) or a general medical condition (e.g., hyperthyroidism).

D. Criterion A of SZ

See above.

E. Types of SD

The type of SD may be may be specifiable, as either Bipolar Type, if the disturbance includes a Manic or a Mixed Episode (or a Manic or a Mixed Episode and Major Depressive Episodes), or Depressive Type, if the disturbance only includes Major Depressive Episodes.

F. Associated Features

Features associated with SD include Learning Problems, Hypoactivity, Psychotic, Euphoric Mood, Depressed Mood, Somatic/Sexual Dysfunction, Hyperactivity, Guilt/Obsession, Odd/Eccentric/Suspicious Personality, Anxious/Fearful/Dependent Personality, and Dramatic/Erratic/Antisocial Personality.

C. Schizotypal Personality Disorder (SPD)

A diagnosis of SPD under the criteria of the DSM-IV is generally based on a pervasive pattern of social and interpersonal deficits marked by acute discomfort with, and reduced capacity for, close relationships as well as by cognitive or perceptual distortions and eccentricities of behavior, beginning by early adulthood and present in a variety of contexts, as indicated by five (or more) of the following:

(1) ideas of reference (excluding delusions of reference)
(2) odd beliefs or magical thinking that influences behavior
(3) inconsistent with subcultural norms (e.g., superstitiousness, belief in clairvoyance, telepathy, or "sixth sense" in children and adolescents, bizarre fantasies or preoccupations)
(4) unusual perceptual experiences, including bodily illusions
(5) odd thinking and speech (e.g., vague, circumstantial, metaphorical, overelaborate, or stereotyped)
(6) suspiciousness or paranoid ideation
(7) inappropriate or constricted affect
(8) behavior or appearance that is odd, eccentric, or peculiar
(9) lack of close friends or confidants other than first-degree relatives
(10) excessive social anxiety that does not diminish with familiarity and tends to be associated with paranoid fears rather than negative judgments about self SPD is diagnosed if the symptoms do not occur exclusively during the course of SZ, a Mood Disorder With Psychotic Features, another Psychotic Disorder, or a Pervasive Developmental Disorder, and the disturbance is not due to the direct physiological effects of a substance (e.g., a drug of abuse, a medication) or a general medical condition.

Associated features of SPD include Depressed Mood and Odd/Eccentric/Suspicious Personality.

D. Bipolar Disorder (BD)

Bipolar disorder is also known as manic-depression or manic-depressive disorder. This condition is characterized by mood that alternates between two emotional extremes, or poles: the sadness of depression and the euphoria of mania (see symptoms of mania below).

Between these emotional swings, there are periods when a person's mood is quite normal. When a person is in the depressed phase of bipolar illness, he or she will have the same symptoms as those found in major depressive disorder. The depressive episodes can often be severe. While in a manic phase, a person experiences mood that is extremely elevated, expansive, or irritable. Mania can seriously impair one's normal judgment. When manic, a person is prone towards reckless and inappropriate behavior such as engaging in wild spending sprees or having promiscuous sex. He or she may not be able to realize the harm of his/her behavior and may even lose touch with reality.

There are two primary types of bipolar disorder:

Bipolar I Disorder is diagnosed when a person has had at least one manic or mixed episode, often along with a major depressive episode. It affects equal numbers of men and women in approximately 0.4% to 1.6% of the population.

Bipolar II Disorder is diagnosed when a person has had a major depressive episode along with at least one hypomanic episode. It affects more women than men in about 0.5% of the population.

People with bipolar disorder experience a wide range of feelings depending on the phase of the illness is present. During a phase of depression, a person will have many of the symptoms of a major depressive episode. He or she may have despondent mood, a loss of energy, feelings of worthlessness or guilt, or problems with concentration. Thoughts of suicide are not uncommon. In fact, 10% to 15% of those with bipolar disorder may die by suicide. If the depression is severe, a person may need to be hospitalized for his or her own safety. For those who go through a phase of hypomania, the experience usually feels quite good. If a person's mood and spirit lightens, he or she will be more outgoing and notice more energy and enhanced self-esteem. Lots of ideas come with ease and a person may feel compelled towards greater activity and productivity. A person in a hypomanic phase may also feel more powerful and omnipotent.

The manic phase is the most extreme part of bipolar disorder. A person becomes euphoric, ideas come much too fast, and concentration is nearly impossible. Anger, irritability, fear, and a sense of being out of control are overwhelming. A person's judgment is impaired, and he or she may behave recklessly without a sense of consequence. Some people lose touch with reality and experience delusions and hallucinations. When this happens, people often need to be hospitalized for their own safety. If a person with bipolar disorder experiences a severe manic episode, he or she may be abusive to children, spouses, or engage in other violent behaviors. There may also be problems with attendance and performance at school or work, as well as significant difficulties in personal relationships.

The cycles of bipolar disorder may be different for each person. Oftentimes a person may first experience depression. Then depression may be replaced with manic symptoms and the cycle between depression and mania may continue for days, weeks, or months. Between phases of depression and mania some people return to their normal mood. Some others have several periods of either depression or mania. Still others may experience several bouts of depression with infrequent phases of hypomania, or repeated manic episodes with occasional depressive periods. A portion of people, roughly 10% to 20% may only experience mania, while others can have both depression and mania at the same time.

For at least 90% of those who have bipolar disorder the condition is recurrent. They will experience future symptoms of the cycles of mania and depression. Approximately 60%-70% of manic episodes may happen just before or after a depressive episode, and this pattern may happen in a particular way for each person. Most people return to a regular level of functioning between episodes, while some (about 20%-30%) may continue to have some problems with mood stability and social and occupational functioning.

Bipolar I disorder affects equal numbers of males and females; however, there does appear to be a gender difference in the onset of the illness. Females are more likely to experience a first episode of depression, while males tend to have a first episode that is manic. Women who have bipolar I or II disorder and who have children may be at a higher risk of experiencing bipolar episodes within several months of giving birth.

A first episode of mania is most likely to occur when a person is in his/her teens or twenties. If a person develops bipolar disorder for the first time after 40 years of age, he or she should be evaluated for the possibility of a medical illness or substance use.

People who have immediate relatives with bipolar I disorder have a higher risk of developing a mood disorder themselves. For these people the rate of developing bipolar II disorder or major depression is 4%-24% and bipolar I disorder is 1%-5%.

Of adolescents who have recurrent major depressive episodes, about 10%-15% of them will likely develop bipolar disorder.

Diagnostic Criteria of Bipolar I Disorder

Summarized from the Diagnostic and Statistical Manual of Mental Disorders-Fourth Edition A. A person experiences a current or recent episode that is manic, hypomanic, mixed, or depressed.

To be a manic episode, for at least one week a person's mood must be out of the ordinary and continuously heightened, exaggerated, or irritable.

At least three of the following seven symptoms have been significant and enduring. If the mood is only irritable, then four symptoms are required.

Self-esteem is excessive or grandiose.

The need for sleep is greatly reduced.

Talks much more than usual.

Thoughts and ideas are continuous and without a pattern or focus.

Easily distracted by unimportant things.

An increase in purposeful activity or productivity, or behaving and feeling agitated.

Reckless participation in enjoyable activities that create a high risk for negative consequences (e.g., extensive spending sprees, sexual promiscuity).

The persons' symptoms do not indicate a mixed episode.

The person's symptoms are a cause of great distress or difficulty in functioning at home, work, or other important areas. Or, the symptoms require the person to be hospitalized to protect the person from harming himself/herself or others. Or, the symptoms include psychotic features (hallucinations, delusions).

The person's symptoms are not caused by substance use (e.g., alcohol, drugs, medication), or a medical disorder.

B. Unless this is a first single manic episode there has been at least one manic, mixed, hypomanic, or depressive episode.

For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.

Depressed mood. For children and adolescents, this may be irritable mood.

A significantly reduced level of interest or pleasure in most or all activities.

A considerable loss or gain of weight (e.g., 5% or more change of weight in a month when not dieting). This may also be an increase or decrease in appetite. For children, they may not gain an expected amount of weight.

Difficulty falling or staying asleep (insomnia), or sleeping more than usual (hypersomnia).

Behavior that is agitated or slowed down. Others should be able to observe this.

Feeling fatigued, or diminished energy.

Thoughts of worthlessness or extreme guilt (not about being ill).

Ability to think, concentrate, or make decisions is reduced.

Frequent thoughts of death or suicide (with or without a specific plan), or attempt of suicide.

The persons' symptoms do not indicate a mixed episode.

The person's symptoms are a cause of great distress or difficulty in functioning at home, work, or other important areas.

The person's symptoms are not caused by substance use (e.g., alcohol, drugs, medication), or a medical disorder.

The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

C. Another disorder does not better explain the episode.

Diagnostic Criteria of Bipolar II Disorder

Summarized from the Diagnostic and Statistical Manual of Mental Disorders-Fourth Edition A. The person currently has, or in the past has had at least one major depressive episode:

For a major depressive episode a person must have experienced at least five of the nine symptoms below for the same two weeks or more, for most of the time almost every day, and this is a change from his/her prior level of functioning. One of the symptoms must be either (a) depressed mood, or (b) loss of interest.

Depressed mood. For children and adolescents, this may be irritable mood.

A significantly reduced level of interest or pleasure in most or all activities.

A considerable loss or gain of weight (e.g., 5% or more change of weight in a month when not dieting). This may also be an increase or decrease in appetite. For children, they may not gain an expected amount of weight.

Difficulty falling or staying asleep (insomnia), or sleeping more than usual (hypersomnia).

Behavior that is agitated or slowed down. Others should be able to observe this.

Feeling fatigued, or diminished energy.

Thoughts of worthlessness or extreme guilt (not about being ill).

Ability to think, concentrate, or make decisions is reduced.

Frequent thoughts of death or suicide (with or without a specific plan), or attempt of suicide.

The persons' symptoms do not indicate a mixed episode.

The person's symptoms are a cause of great distress or difficulty in functioning at home, work, or other important areas.

The person's symptoms are not caused by substance use (e.g., alcohol, drugs, medication), or a medical disorder.

The person's symptoms are not due to normal grief or bereavement over the death of a loved one, they continue for more than two months, or they include great difficulty in functioning, frequent thoughts of worthlessness, thoughts of suicide, symptoms that are psychotic, or behavior that is slowed down (psychomotor retardation).

B. The person currently has, or in the past has had at least one hypomanic episode:

For a hypomanic episode a person's mood must be out of the ordinary and continuously heightened, exaggerated, or irritable for at least four days.

At least three of the following seven symptoms have been significant and enduring. If the mood is only irritable, then four symptoms are required.

Self-esteem is excessive or grandiose.

The need for sleep is greatly reduced.

Talks much more than usual.

Thoughts and ideas are continuous and without a pattern or focus.

Easily distracted by unimportant things.

An increase in purposeful activity or productivity, or behaving and feeling agitated.

Reckless participation in enjoyable activities that create a high risk for negative consequences (e.g., extensive spending sprees, sexual promiscuity).

The episode is a substantial change for the person and uncharacteristic of his or her usual functioning.

The changes of functioning and mood can be observed by others.

The person's symptoms are NOT severe enough to cause difficulty in functioning at home, work, or other important areas. Also, the symptoms neither require the person to be hospitalized, nor are there any psychotic features.

The person's symptoms are not caused by substance use (e.g., alcohol, drugs, medication), or a medical disorder. C. The person has never experienced a manic or mixed episode. D. Another disorder does not better explain the episode. E. The symptoms are a cause of great distress or difficulty in functioning at home, work, or other important areas.

E. Psychiatric Endophenotypes in SZ

A number of endophenotypes, i.e., intermediate phenotypes, that may more closely reflect biological mechanisms behind SZ, have been suggested, such as prepulse inhibition, structural abnormalities evident in MRI scans, specific domains of cognition (e.g., executive function), fine motor performance, working memory, etc.

Endophenotypes can also include clinical manifestations such as hallucinations, paranoia, mania, depression, obsessive-compulsive symptoms, etc., as well as response or lack of response to drugs and comorbidity for substance and alcohol abuse. See, e.g., Kendler et al. (1995); Gottesman and Gould (2003); Cadenhead, 2002; Gottesman and Gould (2003); Heinrichs (2004); and Zobel and Maier (2004). There is now evidence that some candidate genes that were identified using DSM-IV type categorical definitions for "affected" individuals may influence specific endophenotypes, see, e.g., Baker et al. (2005); Cannon et al. (2005); Gothelf et al. (2005); Hallmayer et al. (2005); Callicott et al. (2005); Gornick et al. (2005).

F. Use of PANSS (Positive and Negative Syndrome Scale) score for differential Diagnosis and Evaluation of Clinical Response The Positive and Negative Syndrome Scale (PANSS) is a comprehensive psychometric scale used to classify psychopathology for severe neuropsychiatric diseases, including SZ and BD. It measures a number of psychiatric endophenotypes or dimensions using quantitative scales based on the scoring of patients by clinicians. It is widely used to classify patients into specific subtypes, and is commonly used for measuring the improvement of symptoms in response to clinical interventions (Kay et al., 1987; Kay et al., 1989; Leucht et al., 2005).

Detailed information on PANSS and Scoring Criteria can be found in the art, e.g., on the world wide web at panss.org, or in the book by Kay (1991) which is incorporated herein in its entirety by reference. Based on these sources, the methodology is summarized briefly below.

PANSS comprises 30 individual subscales. Seven constitute a Positive Symptom Scale, seven the Negative Symptom Scale, and the remaining 16 items make up a General Psychopathology Scale. The scores for these scales are arrived at by summation of ratings across component items. Therefore, the potential ranges are 7 to 49 for the Positive and Negative Scales, and 16 to 112 for the General Psychopathology Scale (Source: The PANSS Institute).

Each of the 30 items is accompanied by a specific definition as well as detailed anchoring criteria for all seven rating points. These seven points represent increasing levels of psychopathology, as follows:

1—absent
2—minimal
3—mild
4—moderate
5—moderate severe
6—severe
7—extreme

The PANSS Individual subscales are described below.

P1. DELUSIONS—Beliefs which are unfounded, unrealistic and idiosyncratic.

P2. CONCEPTUAL DISORGANIZATION—Disorganized process of thinking characterized by disruption of goal-directed sequencing, e.g., circumstantiality, loose associations, tangentiality, gross illogicality or thought block.

P3. HALLUCINATORY BEHAVIOUR—Verbal report or behaviour indicating perceptions which are not generated by external stimuli. These may occur in the auditory, visual, olfactory or somatic realms.

P4. EXCITEMENT—Hyperactivity as reflected in accelerated motor behaviour, heightened responsivity to stimuli, hypervigilance or excessive mood lability.

P5. GRANDIOSITY—Exaggerated self-opinion and unrealistic convictions of superiority, including delusions of extraordinary abilities, wealth, knowledge, frame, power and moral righteousness.

P6. SUSPICIOUSNESS/PERSECUTION—Unrealistic or exaggerated ideas of persecution, as reflected in guardedness, ad distrustful attitude, suspicious hypervigilance or frank delusions that others mean harm.

P7. HOSTILITY—Verbal and nonverbal expressions of anger and resentment, including sarcasm, passive-aggressive behavior, verbal abuse and assualtiveness.

N1. BLUNTED AFFECT—Diminished emotional responsiveness as characterized by a reduction in facial expression, modulation of feelings and communicative gestures.

N2. EMOTIONAL WITHDRAWAL—Lack of interest in, involvement with, and affective commitment to life's events.

N3. POOR RAPPORT—Lack of interpersonal empathy, openness in conversation and sense of closeness, interest or involvement with the interviewer. This is evidenced by interpersonal distancing and reduced verbal and nonverbal communication.

N4. PASSIVE/APATHETIC SOCIAL WITHDRAWAL—Diminished interest and initiative in social interactions due to passivity, apathy, anergy or avolition. This leads to reduced interpersonal involvements and neglect of activities of daily living.

N5. DIFFICULTY IN ABSTRACT THINKING—Impairment in the use of the abstract-symbolic mode of thinking, as evidenced by difficulty in classification, forming generalizations and proceeding beyond concrete or egocentric thinking in problem-solving tasks.

N6. LACK OF SPONTANEITY AND FLOW OF CONVERSATION—Reduction in the normal flow of communication associated with apathy, avolition, defensiveness or cognitive deficit. This is manifested by diminished fluidity and productivity of the verbal interactional process.

N7. STEREOTYPED THINKING—Decreased fluidity, spontaneity and flexibility of thinking, as evidenced in rigid, repetitious or barren thought content.

G1. SOMATIC CONCERN—Physical complaints or beliefs about bodily illness or malfunctions. This may range from a vague sense of ill being to clear-cut delusions of catastrophic physical disease.

G2. ANXIETY—Subjective experience of nervousness, worry, apprehension or restlessness, ranging from excessive concern about the present or future to feelings of panic.

G3. GUILT FEELINGS—Sense of remorse or self-blame for real or imagined misdeeds in the past.

G4. TENSION—Overt physical manifestations of fear, anxiety, and agitation, such as stiffness, tremor, profuse sweating and restlessness.

G5. MANNERISMS AND POSTURING—Unnatural movements or posture as characterized be an awkward, stilted, disorganized, or bizarre appearance.

G6. DEPRESSION—Feelings of sadness, discouragement, helplessness and pessimism.

G7. MOTOR RETARDATION—Reduction in motor activity as reflected in slowing or lessening or movements and speech, diminished responsiveness of stimuli, and reduced body tone.

G8. UNCOOPERATIVENESS—Active refusal to comply with the will of significant others, including the interviewer, hospital staff or family, which may be associated with distrust, defensiveness, stubbornness, negativism, rejection of authority, hostility or belligerence.

G9. UNUSUAL THOUGHT CONTENT—Thinking characterized by strange, fantastic or bizarre ideas, ranging from those which are remote or atypical to those which are distorted, illogical and patently absurd.

G10. DISORIENTATION—Lack of awareness of one's relationship to the milieu, including persons, place and time, which may be due to confusion or withdrawal.

G11. POOR ATTENTION—Failure in focused alertness manifested by poor concentration, distractibility from internal and external stimuli, and difficulty in harnessing, sustaining or shifting focus to new stimuli.

G12. LACK OF JUDGMENT AND INSIGHT—Impaired awareness or understanding of one's own psychiatric condition and life situation. This is evidenced by failure to recognize past or present psychiatric illness or symptoms, denial of need for psychiatric hospitalization or treatment, decisions characterized by poor anticipation or consequences, and unrealistic short-term and long-range planning G13. DISTURBANCE OF VOLITION—Disturbance in the willful initiation, sustenance and control of one's thoughts, behavior, movements and speech.

G14. POOR IMPULSE CONTROL—Disordered regulation and control of action on inner urges, resulting in sudden, unmodulated, arbitrary or misdirected discharge of tension and emotions without concern about consequences.

G15. PREOCCUPATION—Absorption with internally generated thoughts and feelings and with autistic experiences to the detriment of reality orientation and adaptive behavior.

G16. ACTIVE SOCIAL AVOIDANCE—Diminished social involvement associated with unwarranted fear, hostility, or distrust.

Each patient's disease manifestation and process is unique. PANSS provides a structured, objective way of describing the various aspects of psychopathology of a given patient. However, proper implementation of the PANSS requires highly trained personnel to conduct the assessment and to interpret the results, and there is potential for site to site variability, especially outside the research setting.

Each of the PANSS composite scales and subscales can be considered a clinical endophenotype. The ability to link genetic profiles to these clinical endophenotypes changes as response to psychotic treatments, or severity of the diseases, will enable clinicians to refine a patient's diagnosis and develop a personalized therapeutic strategy for each patient. By identifying the genetic contributions to specific endophenotypes, the physician can create a personalized diagnosis and treatment regime for the patient.

Additionally, changes in PANSS or the Brief Psychiatric Rating Scale (BPRS), which is derived from PANSS, are often the primary measures of efficacy in clinical trials. One commonly accepted measure of positive clinical response is a decrease of >20% in total PANSS or BPRS. Moreover, certain subscales and composite scores are also evaluated for change. For example, positive symptoms and negative symptoms are two composite scores that have clinical relevance.

G. Clinical Global Impressions (CGI) Scale

The CATIE clinical data set included the Clinical Global Impression (CGI) Scale, an observer-provided assessment of the psychiatric health of the patient (Stroup et al., 2003; Guy 1976). Patients are rated with the CGI Scale from 1 to 7, with higher scores indicating greater severity of illness. The CATIE study provided a response variable that measured the time (in months) of successful treatment as measured by the CGI scale ("TMSUCC1" in the CATIE data).

The Clinical Global Impression (CGI) Scale is a three item observer-rate scale that measures illness severity (CGIS), global improvement or change (CGIC), and therapeutic response. (Guy 1976). One of the most widely-used formats is the Early Clinical Drug Evaluation Program version of the CGI. This format asks a clinician to rate the patient relative to their past experience with other patients with the same diagnosis. This may be done with or without collateral information. The CGI has proven to be a strong measure of efficacy in many clinical drug trials. It is also quick and easy to administer.

Under the CGI, each component is separately rated on a 7-point scale. On the CGIS scale, which measures the severity of illness, the responses range from 1 (normal) to 7 (amongst the most severely ill patients). On the CGIC scale, which measures global improvement or change, the responses range from 1 (very much improved) to 7 (very much worse). Treatment response ratings take into account both therapeutic effect and treatment-related adverse events (side effects). The treatment response ratings may range from 0 (marked improvement and no side-effects) and 4 (unchanged or worse and side-effects outweigh the therapeutic effects). The CGI scale does not produce a global score, but rather rates each component separately.

An example of the Early Clinical Drug Evaluation Program version of the CGI system is found below (Reproduced from Guy W, editor. ECDEU Assessment Manual for Psychopharmacology. 1976. Rockville, Md., U.S. Department of Health, Education, and Welfare):

1. Severity of illness: Considering your total clinical experience with this particular population, how mentally ill is the patient at this time?
0=Not assessed
1=Normal, not at all ill
2=Borderline mentally ill
3=Mildly ill
4=Moderately ill
5=Markedly ill
6=Severely ill
7=Among the most extremely ill patients 2. Global improvement: Rate total improvement whether or not, in your judgment, it is due entirely to drug treatment. Compared to his condition at admission to the project, how much has he changed?
0=Not assessed
1=Very much improved
2=Much improved
3=Minimally improved
4=No change
5=Minimally worse
6=Much worse
7=Very much worse 3. Efficacy index: Rate this item on the basis of drug effect only. Select the terms which best describe the degrees of therapeutic effect and side effects and record the number in the box where the two items intersect. EXAMPLE: Therapeutic effect is rated as 'Moderate' and side effects are judged 'Do not significantly interfere with patient's functioning'=06

| Therapeutic effect | | Side effects | | | |
|---|---|---|---|---|---|
| | | None | Do not significantly interfere with patient's functioning | Significantly interferes with patient's functioning | Outweighs therapeutic effect |
| Marked | Vast improvement. Complete or nearly complete remission of all symptoms | 01 | 02 | 03 | 04 |
| Moderate | Decided improvement. Partial remission of symptoms | 05 | 06 | 07 | 08 |
| Minimal | Slight improvement which doesn't alter status of care of patient | 09 | 10 | 11 | 12 |
| Unchanged or worse | | 13 | 14 | 15 | 16 |
| Not assessed | 00 | | | | |

Reproduced from Guy W, editor. ECDEU Assessment Manual for Psychopharmacology. 1976. Rockville, MD, U.S. Department of Health, Education, and Welfare

V. Treatment of Psychotic Disorders

As described herein, the presence of a SULT4A1-1 haplotype described herein has been correlated with an altered response to a treatment, e.g., a pharmacological treatment. An altered response can be, for example, a positive response (i.e., an improvement in one or more symptoms of the disease), negative response (worsening of one or more symptoms of the disease), no response, or the presence or absence of side effects. Thus, the new methods can also include selecting or developing a treatment regimen for a subject determined to or suspected to have a psychotic disorder based upon the absence or presence of a SULT4A1-1 haplotype.

For example, the inventors identified a SULT4A1-1 haplotype and developed its use in determining the optimal use of antipsychotic medications: i) Patients who are SULT4A1-1 positive have a higher probability of clinically significant improvement when treated with olanzapine when compared to patients who are SULT4A1-1 negative or untested. ii) Patients who are SULT4A1-1 positive may have a higher probability of clinically significant improvement when treated with olanzapine compared to other antipsychotic drugs. For example, this SULT4A1-1 positive group responds better to olanzapine than to risperidone, quetiapine or perphenazine. iii) Patients who are SULT4A1-1 negative have a lower probability of clinically significant improvement when treated with olanzapine compared to similar patients who are SULT4A1-1 positive. Since olanzapine has a significant metabolic side effect burden compared to alternative first-line antipsychotics that demonstrate non-inferiority to olanzapine, it may be appropriate to recommend that first-line antipsychotics with lower metabolic side-effect burdens than olanzapine be used preferentially for SULT4A1-1 negative patients.

The methods can also include administering a selected treatment regimen to a subject having, or suspected to have a psychotic disorder, to thereby treat, prevent or delay further progression of the disease. A treatment regimen can include the administration of a selected antipsychotic medications to a subject identified as at risk of developing a psychotic disorder, before the onset of any psychotic episodes. The medications can be selected based on the status of a SULT4A1-1 haplotype that is associated with, for example, positive response, or the absence of significant side effects.

As used herein, the term "treat" or "treatment" is defined as the prescription, application or administration of a treatment regimen, e.g., a therapeutic agent or modality, to a subject, e.g., a patient. The subject can be a patient having a symptom of a psychotic disorder, or at risk of developing (i.e., a predisposition toward) such a disorder. The treatment can be to cure, heal, alleviate, relieve, alter, remedy, ameliorate, palliate, improve or affect a psychotic disorder, the symptoms of a psychotic disorder, or the predisposition toward a psychotic disorder.

The methods described herein, e.g., methods of determining a treatment regimen and methods of treatment or prevention of a psychotic disorder, can further include the step of monitoring the subject, e.g., for a change (e.g., an increase or decrease) in one or more of the diagnostic criteria for a psychotic disorder, listed herein, or any other parameter related to clinical outcome. The subject can be monitored in one or more of the following periods: prior to beginning of treatment; during the treatment; or after one or more elements of the treatment have been administered. Monitoring can be used to evaluate the need for further treatment with the same or a different therapeutic agent or modality. Generally, a decrease in one or more of the parameters described above is indicative of the improved condition of the subject, although with red blood cell and platelet levels, an increase can be associated with the improved condition of the subject.

For example, the methods can be used to evaluate the suitability of, or to choose between alternative treatments, e.g., a particular dosage, mode of delivery, time of delivery, inclusion of adjunctive therapy, administration in combination with a second agent, or generally to determine the subject's probable drug response genotype. The effects of the treatment or combination of treatments on each of these subjects can be used to determine if a treatment or combination of treatments is particularly effective on a sub-group of subjects having a psychotic disorder. In other embodiments, various treatments or combinations of treatments can be evaluated by administering two different treatments or combinations of treatments to at least two different subjects having a psychotic disorder, and a determined SULT4A1-1 haplotype status as described herein. Such methods can be used to determine if a particular treatment or combination of treatments is more effective than others in treating this subset of patients.

A. Risk of Discontinuation

As described herein, the presence or absence of the SULT4A1-1 haplotype described herein has been correlated with the risk of discontinuation of a particular treatment plan. A risk of discontinuation could be caused by factors such as a lack of efficacy or perceived lack of efficacy, or by treatment emergent side effects (TAEs). Thus, the new methods can also include determining elevated risk of a patient to discontinue treatment with a particular drug based upon the absence or presence of a SULT4A1-1 haplotype.

All of the drugs studied in CATIE have significant side-effect burdens. Thus, an important outcome measure was time to discontinuation for TAE. While the various TAEs are traditional safety measures that are reflected in the existing drug labels, segmentation by SULT4A1-1 haplotype status produces special subpopulations for which the rates and/or severity of the TAE are altered and for which new label language may be appropriate (e.g., as seen for the drug metabolism enzymes). Accordingly, segmentation by SULT4A1-1 status can lead to an altered risk/benefit profile.

For example, the inventors identified the SULT4A1-1 haplotype and developed its use in determining the risk of discontinuation of an antipsychotic medication: i) Patients who are SULT4A1-1 negative have an elevated risk of discontinuation due to treatment-emergent adverse events (TAEs) when treated with olanzapine. ii) Patients who are SULT4A1-1 positive have an elevated risk of discontinuation when treated with risperidone. iii) Patients who are SULT4A1-1 positive have an elevated risk of discontinuation as measured by all-cause discontinuation when treated with risperidone. iv) Patients who are SULT4A1-1 positive have an elevated risk of discontinuation due to lack of efficacy when treated with risperidone. v) Patients who are SULT4A1-1 positive have elevated risk of discontinuation due to treatment emergent side effects when treated with risperidone.

The methods described herein, e.g., methods of determining elevated risk of a patient to discontinue treatment with a particular drug, may include determining the propensity of a patient to continue or discontinue treatment based on the SULT1A1-1 haplotype. As used herein, "propensity to continue treatment" is defined as having a lower risk of discontinuing treatment as defined by a Hazard Ratio of less than 1. The Hazard Ratio measures the risk of an event relative to exposure by comparing the risk of an event in a target group to the risk of the same event in a control group. For example, a HR of 2 would mean that those patients in the target group are twice as likely to experience the event, e.g., discontinue a treatment plan when compared to those in a control group, while a HR of 0.5 means that the patients in the target groups would have 50% lower risk of experiencing the event. As used herein, "propensity to discontinue treatment" is defined as having an increased risk of discontinuing treatment as defined by a Hazard Ratio of greater than 1.

The methods described herein may further comprise selecting a pharmacotherapeutic treatment plan for a subject comprising determining the SULT4A1-1 haplotype and its relation to factors such as efficacy and the risk of discontinuance for reasons such as treatment-emergent adverse events, selecting a pharmacotherapeutic treatment plan based on the SULT4A1-1 haplotype, and treating the subject with the selected pharmacotherapeutic treatment.

B. Current Treatments for Psychotic Disorders

Atypical antipsychotic drugs listed in order of current prescribing frequency for these disorders include: risperidone, quetiapine, olanzapine, aripiprazole, ziprasidone, clozapine, paliperidone, and iloperidone. Typical antipsychotic drugs include haloperidol, fluphenazine, perphenazine, and others (Meltzer and Bobo, 2009). Atypical antipsychotics are favored because of lower parkinsonian side effects and perceived greater efficacy. There are several long acting formulations of typical antipsychotic drugs, which are seldom used in the US. Among the atypical agents, only long acting, injectable risperidone is currently available; long acting paliperidone palmitate is about to be approved, and others, e.g., long acting aripiprazole, are in development. These formulations are highly effective since they provide great help with regard to compliance, an enormous problem with both bipolar and schizophrenia patients. However, they are underutilized in the marketplace.

All of the antipsychotic medications have some degree of side-effects and other limitations. Metabolic side effects with some atypical antipsychotic drugs (weight gain, increased lipids, and problems with glucose regulation, including diabetes) exacerbate the discontinuation rates and limit overall effectiveness the implicated drugs. Olanzapine and clozapine, two of the most efficacious drugs for treating psychosis, have the greatest incidence of metabolic side-effects (Nasrallah, 2007).

Subjects with SZ typically require acute treatment for psychotic exacerbations, and long-term treatment including maintenance and prophylactic strategies to sustain symptom improvement and prevent recurrence of psychosis. Subjects with schizoaffective disorder experience the symptoms of both SZ and affective disorder (manic and/or depressive), thus require the specific treatments for each disorder. Subjects with SPD sometimes require medication for acute psychotic episodes but are often treated using psychosocial methods. The methods described herein can include the administration of one or more accepted or experimental treatment modalities to a person identified as having, suspected to have, or at risk of developing a psychotic disorder such as SZ, SPD, or a SD, based on the determination of a SULT4A1-1 haplotype status. Currently accepted treatments presently include both pharmacologic and psychosocial management, and occasionally electroconvulsive therapy (ECT).

Standard pharmacologic therapies for SZ and SD include the administration of one or more antipsychotic medications, which are typically antagonists acting at postsynaptic $D_2$ dopamine receptors in the brain. Antipsychotic medications include conventional, or first generation, antipsychotic agents, which are sometimes referred to as neuroleptics because of their neurologic side effects, and second generation antipsychotic agents, which are less likely to exhibit neuroleptic effects and have been termed atypical antipsychotics.

Anti-psychotic treatment for SD also include the administration of a combination of antidepressant, and anti-anxiety medication. Suitable antidepressants include serotonergic antidepressants, e.g., fluoxetine or trazodone. Suitable anxiolytics include benzodiazepines, e.g., lorazepam, clonazepam. Lithium can also be administered. Thus, in some embodiments, the methods can include the administration of one or more antidepressant and/or anti-anxiety medications to a person identified as having or suspected to have SD in combination with a treatment plan based on SULT4A1-1 haplotype status.

The methods can also include psychosocial and rehabilitation interventions, e.g., interventions that are generally accepted as therapeutically beneficial, e.g., cognitive-behavioral therapy for treatment-resistant positive psychotic symptoms; supportive, problem-solving, educationally oriented psychotherapy; family therapy and education programs aimed at helping patients and their families understand the patient's illness, reduce stress, and enhance coping capabilities; social and living skills training; supported employment programs; and/or the provision of supervised residential living arrangements.

Currently accepted treatments for SZ are described in greater detail in the Practice Guideline for the Treatment of Patients With Schizophrenia, 2004, which is incorporated herein by reference in its entirety.

Currently accepted treatments for BD are described in greater detail in the Treatment of Patients With Bipolar Disorder, 2006, which is incorporated herein by reference in its entirety.

There are seven commonly prescribed atypical antipsychotic medications for bipolar disorder:
- Abilify (aripiprazole)
- Risperdal (risperidone)
- Zyprexa (olanzapine)
- Seroquel (quetiapine)
- Geodon (ziprasidone)
- Cloazril (clozapine)
- Symbyax (olanzapine/fluoxetine)

The atypical antipsychotics have several significant side-effects, including weight gain, metabolic and hormonal dysregulation, and sexual dysfunction. Weight gain, in particular, can be a significant issue as many people treated with atypical antipsychotics expect to gain weight, sometimes significantly so. Because weight gain is also associated with an increased risk for Type II diabetes, individuals taking an atypical antipsychotic should be carefully monitored by their physician. Other metabolic disturbances include elevated prolactin levels and altered steroid metabolism. Additionally, both men and women report significant levels of sexual dysfunction.

Drugs approved for the treatment of bipolar disorder can have one or more indications, e.g., U.S. FDA (or other regulatory body) approved uses. Some of these indications include: Treatment of Acute Mania episodes; Bipolar Mania maintenance; Bipolar depression; Treatment of mixed mania and depression episodes.

Clinicians most commonly initiate treatment with oral risperidone, especially now that it is generic. Often, however, clinicians will switch patients to another drug after less than 1 to 6 months of treatment. This common practice occurs based on what is perceived by patients and clinicians as both insufficient efficacy and unacceptable side effects, such as Parkinsonism, prolactin elevations or weight gain. Olanzapine, which was found to be the most effective treatment in the CATIE study and is closest in pharmacology to clozapine (the drug generally accepted to have the highest efficacy, particularly in treatment resistant subjects), is considered to be a highly effective agent (Meltzer and Bobo, 2009). Indeed, olanzapine became the most prescribed treatment and initial drug of choice after its introduction until concerns about metabolic side effects became evident (Meltzer, 2005). Metabolic side effects (weight gain, glucose dysregulation, lipid dysregulation and risk of diabetes) have greatly reduced the utilization of olanzapine despite its high efficacy.

C. Pharmacogenetic Testing

Clinicians currently have no way of knowing which drug is best for a specific patient other than from previous successful or unsuccessful trials. They make decisions based on their overall experience with a given drug as well as the influence of advertising and recommendations from clinic supervisors. Also options may be limited because, without a medical rationale, many states limit access to highly efficacious medications (primarily olanzapine) for Medicaid recipients due to cost concerns.

Payers would welcome a diagnostic test that enhances compliance and response rates for their clients. Compliance with oral antipsychotic drugs is a major problem, with 50% of patients ceasing to take them within 6 months of prescription, leading to relapse (return of psychosis) and hospitalization. While U.S. consumers and government agencies spend a considerable amount of money on atypical drugs, relapse and hospitalization represent the largest costs associated with schizophrenia and bipolar disorders. Thus, reducing the rate of hospitalizations and relapse can lead to very significant cost savings and improved patient care.

It is consensus opinion among experts in the treatment of schizophrenia that a pharmacogenetic test which could deliver information that led to a more rapid and extensive control of psychosis would become the dominant driver of choice of medication options. Physicians could engage patients in a rational dialogue regarding treatment choice based on genetic profile. With this additional information, physicians and patients could make calculated risk-benefit analysis regarding potential efficacy and side-effect concerns of the various antipsychotic medications. There is also a published cost-effectiveness analysis which supports the value of pharmacogenetic testing (Perlis et al., 2005).

With regards to both prophylactic and therapeutic methods of treatment of psychotic disorders, such treatments may be specifically tailored or modified, based on knowledge obtained from the field of pharmacogenomics. "Pharmacogenomics," as used herein, refers to the application of genomics technologies such as structural chromosomal analysis, to drugs in clinical development and on the market. See, for example, Eichelbaum et al. (1996) and Linder et al. (1997). Specifically, as used herein, the term refers the study of how a patient's genes determine his or her response to a drug (e.g., a patient's "drug response phenotype," or "drug response genotype"). Thus, another aspect of the invention provides methods for tailoring an individual's prophylactic or therapeutic treatment according to that individual's drug response genotype, especially, a SULT4A1-1 haplotype status.

Information generated from pharmacogenomic research using a method described herein can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when administering a therapeutic composition to a patient, as a means of treating or preventing psychotic disorders.

In one embodiment, a physician or clinician may consider applying knowledge obtained in relevant pharmacogenomics studies, e.g., using a method described herein, when determining whether to administer a pharmaceutical composition, e.g., an antipsychotic agent or a combination of antipsychotic agents, to a subject. In another embodiment, a physician or clinician may consider applying such knowledge when determining the dosage, e.g., amount per treatment or frequency of treatments, of a treatment, e.g., a antipsychotic agent or combination of antipsychotic agents, administered to a patient.

As one example, information regarding a haplotype associated with an altered pharmacogenomic response for psychotic disorders as described herein, can be used to stratify or select a subject population for a clinical trial. The information can, in some embodiments, be used to stratify individuals that may exhibit a toxic response to a treatment from those that will not. In other cases, the information can be used to separate those that are more likely to be non-responders from those who will be responders. The SULT4A1-1 haplotypes described herein can be used in pharmacogenomics-based design and to manage the conduct of a clinical trial, e.g., as described in U.S. Pat. Pub. No. 2003/0108938.

As another example, information regarding a SULT4A1-1 haplotype associated with an increased severity of psychotic disorders, or with altered pharmacogenomic response for psychotic disorders, as described herein, can be used to stratify or select human cells or cell lines for drug testing purposes. Human cells are useful for studying the effect of a polymorphism on physiological function, and for identifying and/or evaluating potential therapeutic agents for the treatment of psychotic disorders, e.g., anti-psychotics. Thus the methods can include performing the present methods on genetic material from a cell line. The information can, in some embodiments, be used to separate cells that respond to particular drugs from those that do not respond to, e.g. which cells show altered second messenger signaling.

D. Theranostics

As used herein, the word "theranostic" is a combination of a specific therapy and diagnostic. The combination represents the use of a diagnostic test to identify a specific patient sub-type(s) of psychotic disorders that have common genetic, clinical, metabolic, and/or prognostic features. By performing a diagnostic test, e.g. a genetic test to determine haplotypes for the SULT4A1 genes, the physician or clinician can place the patient into a specific disease sub-type or category, for example, a SULT4A1-1 positive or negative subgroup. Moreover, patients in such a sub-type respond to a given therapy in a particular manner.

Also included herein are compositions and methods for the identification and treatment of subjects who have an increased severity of a psychotic disorder, or altered clinical presentation of a psychotic disorder, such that a theranostic approach can be taken to test such individuals to determine the effectiveness of a particular therapeutic intervention (e.g., a pharmaceutical or non-pharmaceutical intervention as described herein) and/or to alter the intervention to enhance the effectiveness. Thus, the methods and compositions described herein provide a means of optimizing the treatment of a subject having or suspected to have a psychotic disorder such as SZ. Provided herein is a theranostic approach to treating and preventing a psychotic disorder such as SZ, by integrating diagnostics and therapeutics to improve the real-time treatment of a subject. Practically, this means creating tests that can identify which patients are most suited to a particular therapy, and providing feedback on how well a drug is working to optimize treatment regimens.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

The methods described herein can include retrospective analysis of clinical trial data as well, both at the subject level and for the entire trial, to detect correlations between a haplotype as described herein and any measurable or quantifiable parameter relating to the outcome of the treatment, e.g., efficacy (the results of which may be binary (i.e., yes and no) as well as along a continuum), side-effect profile (e.g., weight gain, metabolic dysfunction, lipid dysfunction, movement disorders, or extrapyramidal symptoms), treatment maintenance and discontinuation rates, return to work status, hospitalizations, suicidality, total healthcare cost, social functioning scales, response to non-pharmacological treatments, and/or dose response curves. The results of these correlations can then be used to influence decision-making, e.g., regarding treatment or therapeutic strategies, provision of services, and/or payment. For example, a correlation between a positive outcome parameter (e.g., high efficacy, low side effect profile, high treatment maintenance/low discontinuation rates, good return to work status, low hospitalizations, low suicidality, low total healthcare cost, high social function scale, favorable response to non-pharmacological treatments, and/or acceptable dose response curves) and a SULT4A1-1 haplotype can influence treatment such that the treatment is recommended or selected for a subject with the SULT4A1-1 haplotype determined.

VI. Kits

Certain aspects of the present invention provide kits, such as diagnostic and therapeutic kits. Kits may comprise a container with a label. Suitable containers include, for example, bottles, vials, and test tubes. The containers may be formed from a variety of materials such as glass or plastic. The container may hold a composition which includes a probe or an array that could be used to determine a SULT4A1-1 haplotype, which could be effective for diagnostic or pharmacogenomic applications. The label on the container may indicate that the composition is used for a specific diagnostic or pharmacogenomic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

Within the scope of the invention are kits comprising a probe that hybridizes with a region of human chromosome as described herein and can be used to detect a polymorphism related to a SULT4A1-1 haplotype. The kit can include one or more other elements including: instructions for use; and other reagents, e.g., a label, or an agent useful for attaching a label to the probe. Instructions for use can include instructions for diagnostic applications of the probe for assessing severity of a psychotic disorder such as SZ in a method described herein. Other instructions can include instructions for attaching a label to the probe, instructions for performing in situ analysis with the probe, and/or instructions for obtaining a sample to be analyzed from a subject. As discussed above, the kit can include a label, e.g., any of the labels described herein. In some embodiments, the kit includes a labeled probe that hybridizes to a region of human chromosome as described herein, e.g., a SULT4A1 polymorphic site as described herein.

The kit can also include one or more additional probes that hybridize to the same chromosome, or another chromosome or portion thereof that can have an abnormality associated with diagnostic applications. For example, the additional probe or probes can be: a probe that hybridizes to human chromosome 22q11-12 or a portion thereof, (e.g., a probe that detects a sequence associated with a psychotic disorder in this region of chromosome 22), or probes that hybridize to all or a portion of 22q12.3 (e.g., near D22S283), 22q11.2, 22q11.2, 22q11-q13, 1q42.1, 1q42.1, 1q21-q22, 2p, 2q, 3p25, 4p, 4q, 5q11.2-q13.3, 6p22.3, 6p23, 6q13-q26, 7q, 8p12-21, 8q, 9p, 10p15-p13 (e.g., near D10S189), 10q22.3, 11q14-q21, 12q24, 13q34, 13q32, 14q32.3, 15q15, 16p, 17q, 18p, 18q, 19p, 20p, 21q, Xq, and/or the X/Y pseudoautosomal region. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes.

Kits for use in self-testing can also be provided. For example, such test kits can include devices and instructions that a subject can use to obtain a sample, e.g., of buccal cells or blood, without the aid of a health care provider. For example, buccal cells can be obtained using a buccal swab or brush, or using mouthwash.

Kits as provided herein can also include a mailer, e.g., a postage paid envelope or mailing pack, that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms, e.g., the test requisition form, and the container holding the sample, can be coded, e.g., with a bar code, for identifying the subject who provided the sample.

Kits may also comprise or be coupled to a system which can make recommendations and/or analysis of efficacy, risk or side effects for treatment of a psychotic disorder based on a determined SULT4A1-1 haplotype status. The system may comprise a server, a processor, or a tangible computer readable program product. For example, if the kit determines the presence or absence of a SULT4A1-1 haplotype, the system may perform an analysis and generate an efficacy and/or risk profile for treatment with a psychotic treatment, such as treating with olanzapine.

VII. Probes

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70%, e.g., 80%, 90%, 95%, 98% or more identity to the target sequence, or any range derivable therein. The probe sequence must also be sufficiently long so that the probe exhibits selectivity for the target sequence over non-target sequences. For example, the probe will be at least 10, e.g., 15, 20, 25, 30, 35, 50, 100, 200, 300, 400, 500, 600, 700, 800, 900, or more nucleotides in length, or any range derivable therein. In some embodiments, the probes are not more than 30, 50, 100, 200, 300, 500, 750, or 1000 nucleotides in length, or any range derivable therein. Specifically, probes may be about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

In some embodiments, the probe is a test probe, e.g., a probe that can be used to detect polymorphisms in a region described herein, e.g., SULT4A1 polymorphisms as described herein. In some embodiments, the probe can hybridize to a target sequence within a region delimited by delimiting SNPs, a first SNP (e.g., rs2285162 or rs2285166) and a second SNP (e.g., rs2285167), for determination of a SULT4A1-1 haplotype.

In some embodiments, the probe can bind to another marker sequence associated with a psychotic disorder such as SZ as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially, e.g., from Applied Biosystems, e.g., the Assays-on-Demand SNP kits. Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson (1998); Wheeless et al. (1994); U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), Texas Red™ (Molecular Probes, Inc., Eugene, Oreg.), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and Cascade™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^3H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end), such as rs2285162, rs2285166, or rs2285167, will generally hybridize preferentially to a nucleic acid comprising that sequence, as opposed to a nucleic acid comprising an alternate polymorphic variant.

VIII. Arrays and Uses Thereof

In another aspect, the invention features methods of determining the absence or presence of a SULT4A1-1 haplotype using an array. In a further aspect, the invention features arrays that include a substrate having a plurality of addressable areas, and methods of using them. At least one area of the plurality includes a nucleic acid probe that binds specifically to a sequence comprising a polymorphism such as rs2285162, rs2285166, or rs2285167, and can be used to detect the absence or presence of said polymorphism, e.g., one or more SNPs, microsatellites, minisatellites, or indels, to determine a SULT4A1-1 haplotype. For example, the array can include one or more nucleic acid probes that can be used to detect a polymorphism such as rs2285162, rs2285166, or rs2285167. In some embodiments, the array further includes at least one area that includes a nucleic acid probe that can be used to specifically detect another marker associated with a psychotic disorder such as SZ as described herein. The substrate can be, e.g., a two-dimensional substrate known in the art such as a glass slide, a wafer (e.g., silica or plastic), a mass spectroscopy plate, or a three-dimensional substrate such as a gel pad. In some embodiments, the probes are nucleic acid capture probes.

Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145). The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments of the invention.

The methods described herein can include providing an array as described herein; contacting the array with a sample, e.g., a portion of genomic DNA that includes at least a portion of human chromosome 22, e.g., a region between and/or including SNPs for a SULT4AJgene, and/or optionally, a different portion of genomic DNA, e.g., a portion that includes a different portion of human chromosomes 1, 2, 3, 4, 5, 6, 7, 8, 9, 10, 11, 12, 13, 14, 15, 16, 17, 18, 19, 20, 21 and/or 22, or another chromosome, e.g., including another region associated with a psychotic disorder, pharmacological response, and/or psychiatric endophenotypes, and detecting binding of a nucleic acid from the sample to the array. Optionally, the method includes amplifying nucleic acid from the sample, e.g., genomic DNA that includes a portion of a human chromosome described herein, and, optionally, a region that includes another region associated with a psychotic disorder, pharmacological response, and/or psychiatric endophenotypes, prior to or during contact with the array.

In some aspects, the methods described herein can include using an array that can ascertain differential patterns of one or more genes in samples from normal and affected individuals (see, e.g., Redon et al., 2006). For example, arrays of probes to a marker described herein can be used to measure polymorphisms between DNA from a subject having a psychotic disorder and control DNA, e.g., DNA obtained from an individual that does not have a psychotic disorder and has no familial risk factors for a psychotic disorder. Since the clones or probes on the array contain sequence tags, their positions on the array are accurately known relative to the genomic sequence. Different hybridization patterns between DNA from an individual afflicted with a psychotic disorder such as SZ and DNA from a normal individual at areas in the array corresponding to markers in human chromosome 1, 2, 3, 4, 5, 6, 7, 8, 9, 10, 11, 12, 13, 14, 15, 16, 17, 18, 19, 20, 21 and/or 22 as described herein, and, optionally, one or more other regions associated with a psychotic disorder are indicative of a risk of SZ-spectrum disorders. Methods for array production, hybridization, and analysis are described, e.g., in Snijders et al. (2001); Klein et al. (1999); Albertson et al. (2003); and Snijders et al. (2002). Real time quantitative PCR can also be used to determine copy number differences.

IX. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Characterization of the Haplotype Structure of the SULT4A1 Gene

The CATIE study, a large federally funded clinical trial designed to assess the efficacy of antipsychotics in a real world setting, is a valuable resource for determining the role of genes in baseline psychopathology and drug response (Lieberman et al., 2005; Stroup et al., 2003). As part of the CATIE trial, detailed clinical evaluations were conducted, including Positive and Negative Syndrome Scale (PANSS) measurements at multiple time points, cognitive evaluation, vital signs, blood chemistry results, and drug response data. Additionally, whole genome SNP genotyping was performed for roughly half of the trial participants (Sullivan et al., 2008).

The inventors used samples collected in the course of the CATIE trial to study SULT4A1 haplotypes to determine if one or more specific haplotypes might contribute to the clinical differences in SSD patients. The inventors contemplated that one or more commonly occurring haplotypes might account for the role of the SULT4A1 gene in the clinical presentation of SSDs. A relatively simple pattern of haplotypes was anticipated, because the gene is highly conserved between species (Liyou et al., 2003; Minchin et al., 2008) and is characterized by a low degree of sequence variation in human populations, displaying a low level of SNP variation even in the introns (Hildebrandt et al., 2007; Lewis and Minchin, 2009). Previous studies in independent sample sets implicated allelic variation in the gene in the genetic etiology and degree of psychopathology of SSDs, but the role of specific haplotypes had not been evaluated previously (Brennan and Condra, 2005; Condra et al., 2007; Meltzer et al., 2008).

A. Data and Methods Relating to the CATIE Sample

Genotype and phenotype data for the CATIE trial were recently made available to qualified researchers through the NIMH Center for Collaborative Genetic Studies on Mental Disorders. For the Caucasian (European American) sample, the inventors evaluated data for 417 CATIE schizophrenia patients, and 419 normal controls self reported as having exclusively European ancestry. This same population was described in a recent study by Sullivan and coworkers, which confirmed that there is no hidden stratification in the sample (Sullivan et al., 2008). The African American sample comprised genotypes for 218 schizophrenia patients and 224 normal controls provided by the CATIE study.

The CATIE genotype data included a total of 11 SNPs located between the previously evaluated rs138110, in the promoter region, and the terminal exon of the gene (Brennan and Condra, 2005; Condra et al., 2007; Meltzer et al., 2008). From lowest to highest base pair position on the chromosome the CATIE SNPs were rs138067 (the SNP is in position 31 of SEQ ID NO:2), rs138079 (the SNP is in position 31 of SEQ ID NO:3), rs470089 (the SNP is in position 31 of SEQ ID NO:4), rs2285161 (the SNP is in position 31 of SEQ ID NO:5), rs2285162 (the SNP is in position 31 of SEQ ID NO:6), rs2285164 (the SNP is in position 31 of SEQ ID NO:7), rs2285167 (the SNP is in position 31 of SEQ ID NO:9), rs470091 (the SNP is in position 31 of SEQ ID NO:10), rs138099 (the SNP is in position 31 of SEQ ID NO:11), rs138102 (the SNP is in position 31 of SEQ ID NO:12), rs138110 (the SNP is in position 31 of SEQ ID NO:13).

B. Methods for Initial Haplotype Discovery and Characterization

The initial genetic analysis to determine the identity and frequency of SULT4A1 haplotypes was performed using the publicly available Haploview program (Barrett et al., 2005; Haploview, Broad Institute 2009). This software assigns expectation-maximization (EM) algorithm—based haplotypes to each individual.

To examine the relationship of haplotypes to psychopathology, baseline PANSS scores were analyzed as quantitative traits by linear regression using the publicly available PLINK software (Purcell et al., 2007; available via pngu.mgh.harvard.edu/~purcell/plink/). For the schizophrenia patients in the CATIE study, the clinical data set included baseline PANSS scores that were based on clinical assessments prior to initiation of the assigned therapy but following the washout period for any patients previously on antipsychotic medication.

C. SULT4A1 Haplotypes in Caucasians and African Americans

As shown in FIG. 1, the Caucasian population displays a high degree of linkage disequilibrium for the region covered by the SNPs. Correlation coefficients ($r^2$) values for several pairs of SNPs exceed 95%.

In fact, E-M maximum likelihood phasing of the 11 SNPs indicated that these markers define only seven haplotypes with frequencies$\geq$0.5% in Caucasians (Table 1). The haplotype designated SULT4A 1-1, occurs at a frequency of 12%.

TABLE 1

SULT4A1 Haplotypes in Caucasians

| Haplotype[a] | Designation | Frequency % |
|---|---|---|
| ACGCAAGCTCA (SEQ ID NO: 16) | SULT4A1-1 | 12.0 |
| ACGCCGGCTCA (SEQ ID NO: 17) | SULT4A1-2 | 13.6 |
| ACGCAAACTCA (SEQ ID NO: 18) | SULT4A1-3 | 14.9 |
| ATGCCGGCTCA (SEQ ID NO: 19) | SULT4A1-4 | 15.4 |
| GCACCGGTCTG (SEQ ID NO: 20) | SULT4A1-5 | 20.9 |
| GCGTCGGCTCG (SEQ ID NO: 21) | SULT4A1-6 | 21.9 |
| GCACCAGTCTG (SEQ ID NO: 22) | SULT4A1-7 | 0.6 |
| ALL OTHERS[b] | | 0.7 |

[a]Haplotypes for the 11 CATIE SNPs were calculated by EM algorithm maximization in Haploview. The marker order is rs138067, rs138079, rs470089, rs2285161, rs2285162, rs2285164, rs2285167, rs470091, rs138099, rs138102, rs138110. The rs2285162 and rs2285167 SNPs, which could be used to determine SULT4A1-1 haplotype status, are designated by underlining. Note that the rs2285162 "A" allele occurs in combination with rs2285167 "G" only for the SULT4A1-1 haplotype.
[b]Four rare haplotypes were inferred: one appeared twice and three appeared only once in the entire sample. All of these included the either rs2285162(C) in combination with rs2285167 (G) or rs2285162(A) in combination with rs2285167(A).

Table 1 allows one to draw an important conclusion relating to the SULT4A1-1 haplotype. Specifically, the extended, 11 SNP SULT4A1-1 haplotype is uniquely tagged by the two-SNP combination rs2285162(A)-rs2285167(G). Therefore, the rs2285162(A)-rs2285167(G) combination is both necessary and sufficient to identify the presence of the entire extended SULT4A1-1 haplotype.

Figure 2:
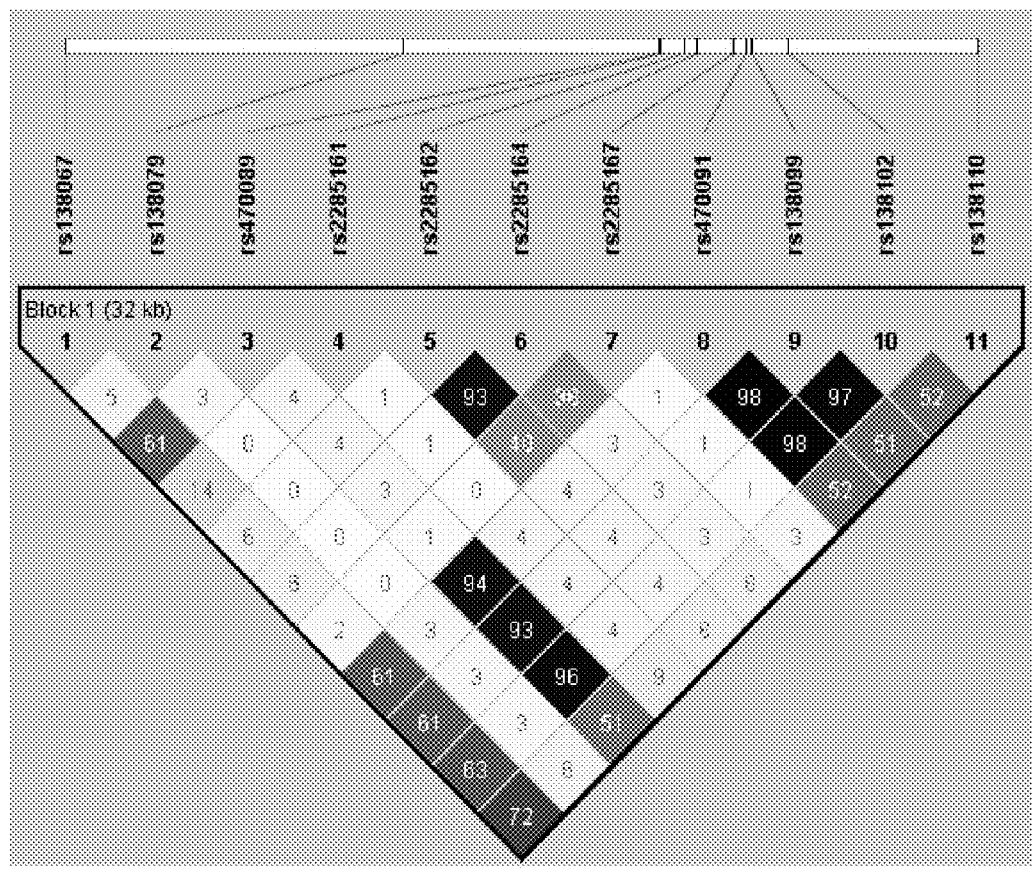
FIG. 2: Linkage disequilibrium for the African American sample. The Haploview output shows pairwise correlation coefficients ($r^2$ values in %) for the 11 CATIE SNPs (N=442 persons).

As shown in FIG. 2, the African American population displays somewhat less linkage disequilibrium for the region. However, the pattern is similar to what was observed in the Caucasian population.

For African Americans, E-M maximum likelihood phasing of the 11 SNPs indicated that these markers define nine extended haplotypes with frequencies$\geq$0.5% (Table 2). The SULT4A1-1 haplotype is rarer than in the Caucasian Sample occurring at a frequency of only 5.2% in African Americans compared to a frequency of 12% in Caucasians. Despite this difference in frequency, the rs2285162(A)-rs2285167(G) sub-haplotype is both necessary and sufficient to identify the presence of the extended SULT4A1-1 haplotype in African Americans.

TABLE 2

SULT4A1 Haplotypes in African Americans

| Haplotype[a] | Designation | Frequency % |
|---|---|---|
| ACGCAAGCTCA (SEQ ID NO: 16) | SULT4A1-1 | 5.2 |
| ACGCCGGCTCA (SEQ ID NO: 17) | SULT4A1-2 | 37.1 |
| ACGCAAACTCA (SEQ ID NO: 18) | SULT4A1-3 | 3.9 |
| ATGCCGGCTCA (SEQ ID NO: 19) | SULT4A1-4 | 6.4 |
| GCACCGGTCTG (SEQ ID NO: 20) | SULT4A1-5 | 29.4 |
| GCGTCGGCTCG (SEQ ID NO: 21) | SULT4A1-6 | 9.0 |
| GCACCAGTCTG (SEQ ID NO: 22) | SULT4A1-7 | 0.2 |
| ACGCCGGCTCG (SEQ ID NO: 23) | SULT4A1-8 | 5.6 |
| GCGCCGGCTCA (SEQ ID NO: 24) | SULT4A1-9 | 0.9 |
| GCGCCGGTCTG (SEQ ID NO: 25) | SULT4A1-10 | 0.7 |
| ALL OTHERS[b] | | 1.6 |

[a]Haplotypes for the 11 CATIE SNPs were calculated by EM algorithm maximization in Haploview. The marker order is rs138067, rs138079, rs470089, rs2285161, rs2285162, rs2285164, rs2285167, rs470091, rs138099, rs138102, rs138110. The rs2285162 and rs2285167 SNPs, which could be used to determine SULT4A1-1 haplotype status, are designated by underlining. Note that the rs2285162 "A" allele occurs in combination with rs2285167 "G" only for the SULT4A1-1 haplotype.
[b]Nine additional rare haplotypes were inferred. All of these included the rs2285162(C) in combination with rs2285167(G).

The greater diversity of Haplotypes in the African American sample is expected based upon the well established greater genetic diversity of African Americans relative to European Americans. Nonetheless, as was seen in the Caucasian sample, the rs2285162(A)-rs2285167(G) combination is both necessary and sufficient to identify the presence of the 11 SNP SULT4A1-1 haplotype in African Americans.

To confirm these findings, the inventors used two additional approaches. The inventors evaluated linkage disequilibrium and pre-calculated haplotype data available from the International HapMap Project (2009) for Europeans (CEU population) and African Americans (ASW population). Additionally, the inventors performed EM algorithm analysis for genotypes of approximately 2,600 Caucasian samples and 2,600 African American samples made available by the National Institutes of Mental Health on behalf of the dbGAP consortium (2009).

In brief, these additional analyses confirm that the rs2285162(A)-rs2285167(G) haplotype is sufficient to tag the SULT4A1-1 haplotype in both Caucasians and African Americans for a region corresponding to that covered by the 11 CATIE SNPs. These analyses also demonstrate that the rs2285166 is in complete linkage disequilibrium with rs2285162, such that the rs2285166(T)-rs2285167(G) haplotype suffices to uniquely tags the SULT4A1-1 haplotype.

Furthermore, these analyses did highlight one important difference between the Caucasian and African American populations. In Caucasians, the SULT4A1-1 haplotype extends beyond the region covered by the 11 CATIE SNPs, encompassing the promoter region and the 3' terminal exon. For African Americans, however, this relationship holds for less than half of the extended haplotypes tagged by the two-SNP core haplotypes.

Example 2

The SULT4A1-1 Haplotype Correlates with Psychopathology in Caucasians

Linear regression analysis using PLINK indicated that the SULT4A1-1 haplotype showed a significant association with baseline PANSS scores for Caucasian schizophrenia patients in the CATIE study (Table 3; P=0.03). This haplotypes explains approximately 1% of the variance with a beta weight of 4.0, corresponding to an increase in total PANSS score of 4.0 associated with the haplotype.

TABLE 3

Correlation of SULT4A1 Haplotypes with PANSS Total Score in CATIE

| Haplotype (designation)[a] | Frequency | Beta[b] | P value[c] |
|---|---|---|---|
| ACGCAA[G]GCTCA (SULT4A1-1) (SEQ ID NO: 26) | 0.116 | 4.00 | 0.034 |
| ACGCCG[A]GCTCA (SULT4A1-2) (SEQ ID NO: 27) | 0.125 | 0.46 | 0.723 |
| ACGCAA[G]ACTCA (SULT4A1-3) (SEQ ID NO: 28) | 0.145 | -0.05 | 0.753 |
| ATGCCG[A]GCTCA (SULT4A1-4) (SEQ ID NO: 29) | 0.158 | -2.04 | 0.287 |
| GCACCG[G]GTCTG (SULT4A1-5) (SEQ ID NO: 30) | 0.222 | -1.67 | 0.344 |
| GCGTCG[G]GCTCG (SULT4A1-6) (SEQ ID NO: 31) | 0.237 | 0.17 | 0.784 |

[a]Haplotypes for the 11 CATIE SNPs were calculated by EM algorithm maximization in PLINK. The marker order is rs138067, rs138079, rs470089, rs2285161, rs2285162, rs2285164, rs2285167, rs470091, rs138099, rs138102, rs138110. SNP rs138110 was used in previous studies and is designated by underlining. Alleles for a second SNP used in previous studies (rs138097, square brackets) were inferred using data from the International HapMap project.
[b]Beta weights (regression coefficients) for quantitative trait, general linear model in PLINK.
[c]Asymptotic P value for the t-statistic (N = 417; Caucasian only).

This relationship did not hold for the African American patients in the CATIE sample. This could reflect the smaller sample size for the African American samples or the fact that the 11 SNP SULT4A1-1 haplotype does not capture allelic variation over an extended region in African Americans.

To determine if the SULT4A1-1 haplotype affects baseline psychopathology, individuals from the CATIE study were scored for the presence of the SULT4A1-1 haplotype using the rs2285162(A)-rs2285167(G) core haplotype (See Example 3 for details), and total baseline PANSS scores for groups with and without the haplotype were compared. Table 4 shows the baseline PANSS scores for the two haplotype groups in the CATIE sample. The frequency of SULT4A1-1 positive patients is approximately 22-23% and does not differ from Hardy-Weinberg expectations.

TABLE 4

Relationship of SULT4A1-1 Status to Baseline PANSS Score[a]

| Sample | SULT4A1-1 + | SULT4A1-1 − |
|---|---|---|
| CATIE | 75.7 (18.0) N = 88 | 71.1 (17.2) N = 307 |

[a]Total PANSS scores, means (standard deviation) for patients whose SULT4A1-1 haplotype status could be assigned with error probabilities of <1%.

In summary, a two-SNP haplotype, rs2285162(A) [or rs2285166(T)]-rs2285167(G), is sufficient to tag an extended SULT4A1-1 haplotype in Caucasians. This haplotype correlates with elevated baseline PANSS scores in Caucasian patients suffering from SSDs. The following example (Example 3) describes how SULT4A1-1 haplotype status can be inferred from genotype data, and Example 4 describes pharmacogenetic findings relating to SULT4A1-1 haplotype test.

Example 3

Assigning SULT4A1-1 Haplotype Status

Finished genotypes provided by the NIMH Center for Collaborative Genetic Studies on Mental Disorders were used to establish SULT4A1-1 haplotype status using a simple and intuitive scoring method for the presence of this established haplotype. As described in the previous Examples, the rs2285162(A) [or rs2285166(T)]-rs2285167(G) combination is both necessary and sufficient to identify SULT4A1-1 haplotype in Caucasians.

A. Genotyping Methodology

The inventors seek only to document the well established quality of the genotyping methodologies used for the Examples, and do not mean to limit the invention to the particular molecular platform. For example, the Affymetrix platform, a widely used commercially available platform, was used in the CATIE study. The technology behind this platform has been included in CLIA-approved genotyping tests at the manufactures' own facilities and at third party providers.

The data process by the inventors were derived from a large scale genotyping project that used microarray-based whole genome SNP genotyping approaches. The project was performed by the CATIE study group using Affymetrix and Perlegen microarray platforms (Sullivan et al., 2008).

The inventors were provided finished genotype data and do not have access to raw data files such as .cel files. As described in the previous and present examples, genotypes provided by others were used to establish SULT4A1-1 haplotype status using a simple and intuitive scoring method for the presence of this established haplotype.

Details of the genotyping performed by the CATIE consortium, including their rigorous quality control procedures, are described elsewhere (Sullivan et al., 2008). Briefly, peripheral venous blood was collected, and genomic DNA was extracted from lymphocytes. Analyses were performed at Perlegen Sciences in its CLIA, GLP facility using two microarray genotyping systems. The first was the Affymetrix 500K "A" chipset (Nsp I and Sty I chips, Santa Clara, Calif.) used as specified by the manufacturer. Detailed description of the SNP detection methodology can be found in Affymetrix product documentation (world wide web via affymetrix.com/products_services/arrays/specific/500k.affx). Secondly, Perlegen used a custom 164K chip. The genotype calling methodology and extensive quality control measures used by the CATIE study group were reported by Sullivan and coworkers (Sullivan et al., 2008) and further described in detail in the supplemental technical material provided by the CATIE consortium (Sullivan et al., 2008, Supplementary Information).

As an example of the level of quality control used, the CATIE group performed duplicate analysis on 36 samples. The proportion of SNPs with non-missing genotype calls that disagreed in these duplicated samples was 0.00291. As an additional control, 277 individuals were genotyped at a second facility using a different SNP-calling algorithm to investigate potential site bias. Only 0.73% of called genotypes differed between the two sites.

B. Core SULT4A1-1 Haplotypes

Table 5 summarizes the observed frequencies for core haplotypes employing the SNPs rs2285162, rs2285166 and rs2285167 in Caucasians. The results in Table 5 are based on E-M algorithm maximization estimates for approximately 2,600 samples (see Example 1). Only three of the eight theoretically possible haplotypes were observed.

TABLE 5

Core SULT4A1-1 Haplotypes in Caucasians

| Core Haplotypes[a] | Tagged Extended Haplotypes | Approximate Frequency % |
|---|---|---|
| ATG | SULT4A1-1 | 12.0 |
| CCG | SULT4A1-2,-4,-5,-6,-7 | 73[b] |
| ATA | SULT4A1-3 | 15.0[c] |

[a]The marker order is rs2285162, rs2285166, rs2285167.
[b]Includes three rare extended haplotypes containing the CCG core haplotype.
[c]Includes one rare extended haplotype containing the ATA core haplotype.

Table 6 summarizes the observed frequencies for core haplotypes employing the SNPs rs2285162, rs2285166 and rs2285167 in African Americans. Again, these results are based on E-M algorithm maximization estimates for approximately 2,600 samples (see Example 1). Only three of the eight theoretically possible haplotypes were observed.

TABLE 6

Core SULT4A1 Haplotypes in African Americans

| Haplotypes[a] | Designation | Approximate Frequency % |
|---|---|---|
| ATG | SULT4A1-1 | 5.2 |
| CCG | SULT4A1-2,4,5,6,7,8,9,10 | 90.9[b] |
| ATA | SULT4A1-3 | 3.9 |

[a]The marker order is rs2285162, rs2285166, rs2285167.
[b]Includes all observed rare haplotypes.

C. Using SNP Genotypes to Determine SULT4A1-1 Haplotype Status

For the SNPS available in the CATIE study, SULT4A1-1 status is determined based on the genotype of the SNPs, rs2285162(A or C in position 31 of SEQ ID NO:6) and rs2285167(A or G in position 31 of SEQ ID NO:9). As described immediately above, these SNPs define only three common haplotypes. Accordingly, patients are designated as SULT4A1-1 positive using the simple scoring method illustrated in Table 7.

TABLE 7

Assignment of SULT4A1-1 Haplotype Status in the CATIE

| rs2285162 | rs2285167 | Possible haplotype combination | SULT4A1-1 status |
|---|---|---|---|
| A/C | G/G | AG/CG | Positive |
| A/A | A/G | AG/AA | Positive |
| A/A | G/G | AG/AG | Positive |
| C/C | G/G | CG/CG | Negative |
| A/A | A/A | AA/AA | Negative |
| A/C | A/G | AA/CG | Negative |

The haplotype scoring can be automated in Microsoft Excel by combining a series of logical arguments. For purposes of illustration, samples of the scoring by the Excel spreadsheet are reproduced below (Table 8).

TABLE 8

Sample output for SULT4A1-1 status calling by the Excel Spreadsheet

| A Sample ID | B rs2285162 | C rs2285167 | D Callable? | E Genotype | F Positive status call possible? | G SULT4A1-1 Status |
|---|---|---|---|---|---|---|
| 1 | A_C | G_G | YES | A_C G_G | 1 | 1 |
| 2 | A_A | A_G | YES | A_A A_G | 1 | 1 |
| 3 | A_A | G_G | YES | A_A G_G | 1 | 1 |
| 4 | C_C | G_G | YES | C_C G_G | 0 | 0 |
| 5 | A_A | A_A | YES | A_A A_A | 0 | 0 |
| 6 | A_C | A_G | YES | A_C A_G | 0 | 0 |
| 7 | ? | G_G | NO | | 0 | |
| 8 | C_C | ? | NO | | 0 | |
| 9 | ? | G_G | NO | | 0 | |
| 10 | ? | ? | NO | | 0 | |

The example of Table 8 shown is for the rs2285162-rs2285167 combination. A similar scoring method is used for the rs2285166-rs2285167 combination, by substituting the appropriate alleles of rs2285166 (the SNP is in position 31 of SEQ ID NO:14) for the corresponding alleles of rs2285162 (the SNP is position 31 of SEQ ID NO:6). Failed genotypes, which are rare, are coded as question marks and result in "NO" designation in column "D". Column "G" provides the haplotype status as follows: 1=positive, 0=negative, and a blank cell indicates genotyping failure requiring retesting.

In summary, SULT4A1-1 haplotype status can be assigned using a simple and intuitive scoring method. This method is easily automated using logical functions in programs such as Microsoft Excel.

Example 4

Clinical Performance of SULT4A1-1 Haplotype

There are several different metrics for quantifying response in clinical trials of antipsychotic medications. The most commonly used psychometric instrument is the Positive and Negative Syndrome Scale (PANSS), a 30-item semi-quantitative instrument scored by clinical professionals (Kay et al., 1987). The greater the decrease in PANSS score, the better the clinical response. The most direct measure of clinical response is absolute change in PANSS score. In addition to absolute change, the improvement is often reported as a percentage change from baseline PANSS score.

This percentage change in PANSS may be used to derive a categorical definition of response, wherein subjects who meet a certain critical threshold of change are classified as responders and those that do not meet that criterion are classified as non-responders. A decrease of at least 20% in total PANSS is one commonly used threshold for response (Leucht et al., 2009).

Alternatively, many drug trials for antipsychotic medications report response as quantitative changes in PANSS score (Leucht et al., 2009). This approach is particularly useful for trials with active comparators or in cases where claims of drug superiority or non-inferiority are important (i.e. where relative improvement in symptoms is a key factor).

Both approaches shed light on the clinical utility of the SULT4A1-1 haplotype as a biomarker, so the inventors presented results for both categorical definitions of response and for quantitative changes in percent PANSS.

A. Responder/Nonresponder Statistics Based on Haplotype Status

The design of the CATIE study has been described in detail by others (Lieberman et al., 2005; Stroup et al., 2003). Briefly, 1460 subjects were randomly assigned one of several antipsychotics and those who did not respond or who chose to quit their current medication were re-randomized to another drug. A total of 738 subjects consented to provide DNA for genetic study. Details regarding SNP genotyping and quality control have been recently published (Sullivan et al., 2008). Retrospective genetic analyses, judged to be exempt from human studies requirements by an IRB, were conducted in the current study.

All tested patients were studied using well established clinical endpoints comparing baseline, intermediate, and last observation carried forward (LOCF) for the PANSS scores using CATIE data. LOCF analysis is a commonly used clinical endpoint for clinical trials for neuropsychiatric drugs, with changes in PANSS scores of between negative 20% and negative 30% used as typical endpoints to indicate clinically significant response (Leucht et al., 2009). To remove time on drug as a variable for the CATIE trial, analysis was limited to only those patients who were randomized to a different drug following the initial washout period (drug switchers).

As summarized in Table 9, when patients are segmented by SULT4A1-1 status and treatment arm, olanzapine-treated SULT4A1-1 positive (Caucasian) subjects demonstrated a greater likelihood of achieving the 20% PANSS decrease than any other group in CATIE. Several points may be made regarding these data.

TABLE 9

Relationship of SULT4A1-1 Status to Drug Response in CATIE Caucasians

| | SULT4A1-1 Positive[a] | | | SULT4A1-1 Negative[a] | | | |
|---|---|---|---|---|---|---|---|
| Drug | ≦−20% | ≧−20% | Responders | ≦−20% | ≧−20% | Responders | P-value[b] |
| Olanzapine | 10 | 5 | 66.6% | 10 | 33 | 23.2% | 0.006 |
| Risperidone | 3 | 14 | 17.6%* | 18 | 43 | 29.5%* | 0.53 |
| Quetiapine | 7 | 11 | 38.8% | 13 | 50 | 20.6%** | 0.12 |
| Perphenazine | 5 | 9 | 35.7% | 16 | 47 | 25.4%** | 0.51 |
| Ziprasidone | 3 | 7 | 30.0% | 6 | 32 | 15.7%** | 0.37 |
| All Drugs | 28 | 46 | 37.8% | 63 | 205 | 23.5%** | 0.02 |

TABLE 9-continued

Relationship of SULT4A1-1 Status to Drug Response in CATIE Caucasians

| Drug | SULT4A1-1 Positive[a] | | | SULT4A1-1 Negative[a] | | | P-value[b] |
|---|---|---|---|---|---|---|---|
| | ≤−20% | ≥−20% | Responders | ≤−20% | ≥−20% | Responders | |
| All Except Olanzapine | 18 | 43 | 29.5%* | 53 | 172 | 23.6%** | 0.40 |

[a]Numbers of individuals showing the specified percent change in total PANSS (LOCF). A greater response corresponds to a more negative change in PANSS score, with individuals showing a change in PANSS of ≤−20% being categorized as responders.
[b]$\chi^2$ (Yates Corrected) based p-value comparing SULT4A1-1 positive subjects to SULT4A1-1 negative subjects for the particular drug or combination of drugs.
*Olanzapine-treated SULT4A1-1 positive subjects responded significantly better p < 0.05
**Olanzapine-treated SULT4A1-1 positive subjects responded significantly better p < 0.01

First, SULT4A1-1 positive patients have a statistically higher probability of experiencing a clinical response using olanzapine therapy when compared to patients who are SULT4A1-1 negative (P=0.006). Furthermore, this higher probability of response remains statistically significant when comparing use of the drug in SULT4A1-1 positive patients (10 out of 15 responded) to patients unselected for SULT4A1-1 status (20 out of 58; P=0.05). Although when all drugs are considered together, SULT4A1-1 positive patients do respond better than SULT4A1-1 negative patients, statistically significant superiority is lost if olanzapine-treated patients are omitted (Table 9, last two rows).

Second, SULT4A1-1 positive patients have a higher probability of experiencing a clinically significant response using olanzapine when compared to other antipsychotic drugs. For olanzapine compared to risperidone, the difference is statistically significant (P=0.014). SULT4A1-1 positive patients also respond significantly better to olanzapine than to all other drugs considered together (P=0.018).

Third, SULT4A1-1 negative patients respond at similar rates to all medications (with the possible exception of ziprasidone), but have a lower probability of clinically significant response for olanzapine compared to SULT4A1-1 positive patients. Therefore, SULT4A1-1 positive patients appear to be a subset of patients who are particularly good candidates for olanzapine treatment, while there appears to be no efficacy advantage for olanzapine in SULT4A1-1 negative patients The inventors also examined the impact of the SULT4A1-1 status on drug response in the African American patients from the CATIE trial (Table 10). For self-described African Americans segmented using the two-SNP SULT4A1-1 haplotype test, the relative effectiveness of the drugs in the haplotype groups did not resemble that observed for patients of European descent. The SULT4A1-1 haplotype is relatively rare in African Americans, and the numbers are too small for valid statistical evaluation. Furthermore, as discussed in Example 3, the core haplotype does not reproducibly tag an extended haplotype in African Americans. Accordingly, it is impossible to determine if the apparent response differences are the result of random variation due to the small sample sizes of the SULT4A1-1 positive African American patients, reflect differences in the extended tagged haplotypes in African Americans, or result from some other interacting system that differs between African and European Americans. Therefore, all further analyses focused exclusively on Caucasian subjects.

TABLE 10

Relationship of SULT4A1-1 Status to Drug Response in CATIE African Americans

| Drug | SULT4A1-1 Positive[a] | | | SULT4A1-1 Negative[a] | | |
|---|---|---|---|---|---|---|
| | ≤−20% | ≥−20% | Responders | ≤−20% | ≥−20% | Responders |
| Olanzapine | 1 | 3 | 25% | 15 | 30 | 33.3% |
| Risperidone | 3 | 2 | 60% | 7 | 34 | 17.1% |
| Quetiapine | 2 | 4 | 33.3% | 9 | 25 | 26.5% |
| Perphenazine | 0 | 2 | 0% | 10 | 27 | 27.0% |
| Ziprasidone | 0 | 3 | 0% | 4 | 22 | 15.4% |
| All Drugs | 6 | 14 | 30.0% | 45 | 138 | 24.6% |
| All Except Olanzapine | 5 | 11 | 31.3% | 30 | 108 | 21.7% |

[a]Numbers of individuals showing the specified percent change in total PANSS (LOCF). A greater response corresponds to a more negative change in PANSS score, with individuals showing a change in PANSS of ≤−20% being categorized as responders.

Figure 3:
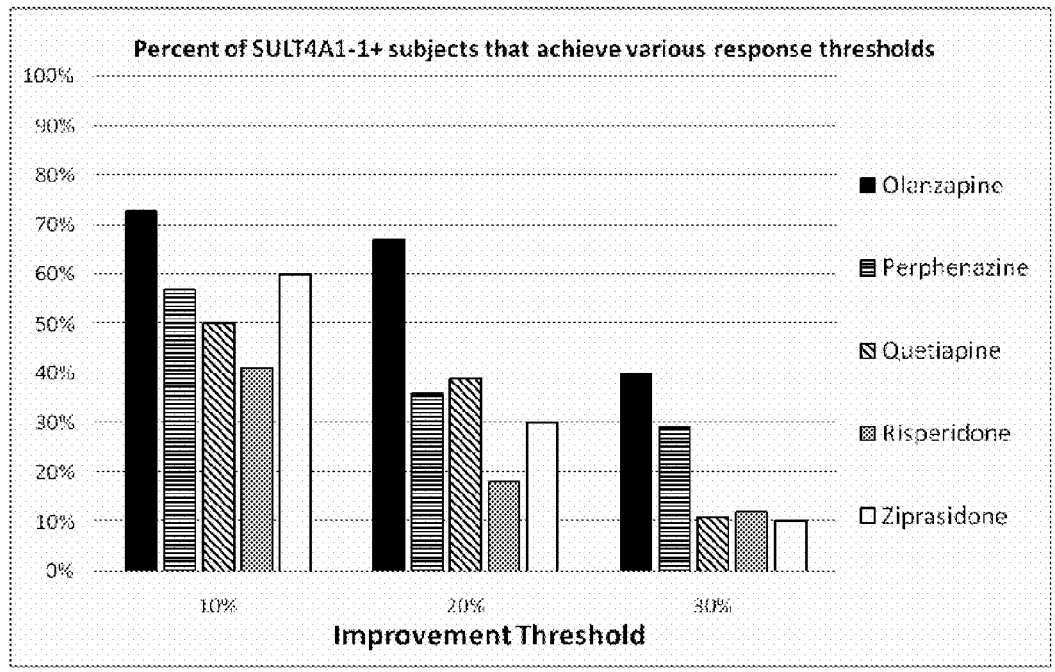
FIG. 3: Response of SULT4A1-1 positive subjects in CATIE at various response thresholds.
Figure 4:
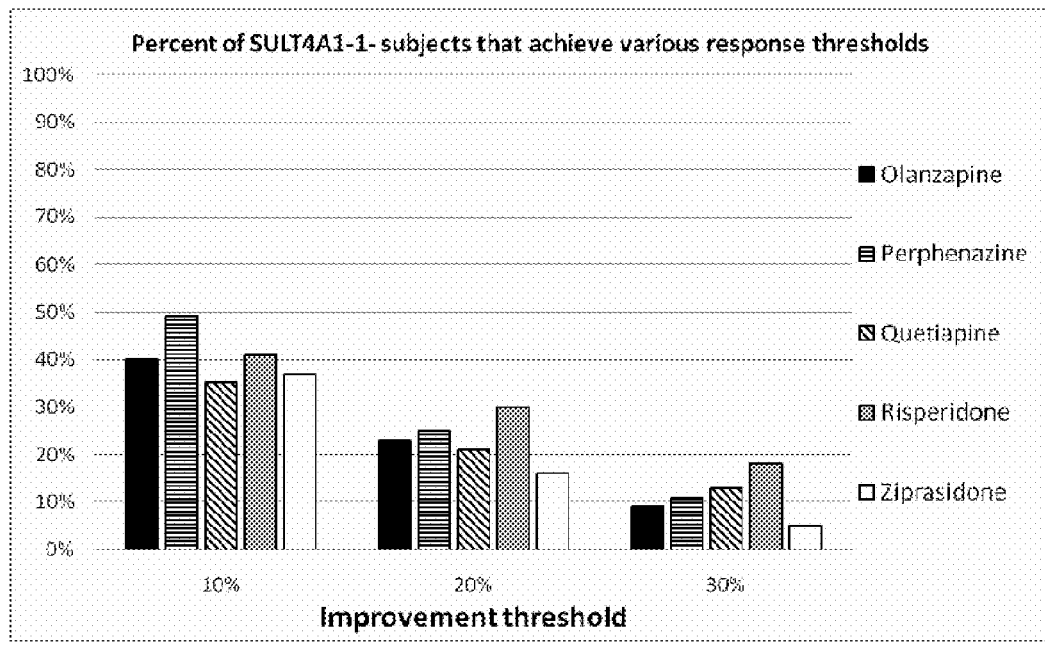
FIG. 4: Response of SULT4A1-1 negative subjects in CATIE at various responses thresholds.

The inventors also examined the possibility of using different response thresholds in CATIE. FIGS. 3 and 4 show the distribution of SULT4A1-1 positive and negative subjects, respectively, that met three different response thresholds for the various drugs. As can be seen, the results for the 10% and 30% thresholds are qualitatively similar to those for the 20% threshold. However, more stringent thresholds tend to amplify the difference between SULT4A1-1 positive patients treated with olanzapine and the other groups. For example, at the 30% level, SULT4A1-1 positive subjects were about four times more likely to respond to olanzapine than to any other atypical drug (quetiapine, risperidone, or ziprasidone). Similarly, at the 30% threshold, response for this group was at least twice that of the SULT4A1-1 negative patients treated with any of the drugs.

In summary, the results for the CATIE study show olanzapine-treated SULT4A1-1 positive subjects demonstrated the greater response than any other group using a 20% threshold. While a more stringent threshold could have been used, the 20% level provides both a clinically meaningful difference in response and good discrimination between SULT4A1-1 positive and negative patients.

To summarize the results, using the 20% threshold, olanzapine-treated SULT4A1-1 positive subjects demonstrated the highest levels of response. More stringent thresholds amplify the difference between this group and the other haplotype/treatment combinations. However, the 20% level provided both a clinically meaningful difference in response and good discrimination between SULT4A1-1 positive and negative patients.

B. Quantitative Response Based on Haplotype Status

As mentioned previously, the mean change in absolute or percent PANSS provides an important measure of efficacy in patients undergoing antipsychotic treatments. Indeed, many pivotal trials in the psychosis field used absolute and/or percentage change in PANSS Score as the primary endpoint (Leucht et al., 2009). The performance of the investigational drug is then compared with placebo and/or an active comparator. Therefore, in addition to examining a categorical definition of clinically significant response, the inventors determined the impact of segmentation by SULT4A1-1 status on the quantitative measure of clinical improvement—delta PANSS. For the purposes of illustration, the inventors have elected to use percent change rather than absolute change so that the values seen herein are directly comparable to the dichotomous analysis shown above. The same analyses using the absolute change produce essentially the same results.

Table 11 shows the mean and standard deviation for the percent change in response for each of the drug arms segmented by SULT4A1-1 status for the CATIE study. As can be seen from the table, the olanzapine-treated SULT4A1-1 positive group displayed superiority to all other groups with at least a trend suggesting potential significance if replicated in a larger data set. Additionally, as seen with the categorical responder/non-responder definition, all drug arms except risperidone demonstrated a numerically superior response for SULT4A1-1 positive patients.

TABLE 11

Change in PANSS Values for the CATIE Study

| | SULT4A1-1 Positive | | | SULT4A1-1 Negative | | |
|---|---|---|---|---|---|---|
| Drug | N | DELTA PANSS %[a] | SD[b] | N | DELTA PANSS %[a] | SD[b] |
| Olanzapine | 15 | −24 | 16 | 43 | −3*** | 22 |
| Perphenazine | 14 | −10* | 24 | 63 | −3*** | 25 |
| Quetiapine | 18 | −9** | 21 | 63 | 0*** | 26 |
| Risperidone | 17 | −5*** | 21 | 61 | −5*** | 25 |
| Ziprasidone | 10 | −8* | 24 | 38 | −4*** | 18 |
| All Drugs | 74 | −11** | 22 | 268 | −3*** | 24 |
| All Drugs - Olz | 59 | −8*** | 22 | 225 | −3*** | 24 |

[a]Mean change in PANSS score from baseline to LOCF
[b]Standard deviation of the mean
*P < 0.1, P < 0.05, and *P < 0.01 olanzapine-treated SULT4A1-1 positive responded significantly better Olanzapine overall efficacy advantage in CATIE can be explained primarily by the response of the SULT4A1-1 positive patients. Overall olanzapine shows superior response compared to the other drugs (delta PANSS −9 vs. −4). For SULT4A1-1 positive patients, which account for only 25.8% of the olanzapine arm, olanzapine shows superior response to all other drugs (delta PANSS −24 versus −8). However, for SULT4A1-1 negative patients, olanzapine does not display superiority over the other drugs (−delta PANSS −3 versus −3).

Another way to consider the response of the various groups is to analyze the difference in the mean PANSS changes. Table 12 compares various drug-SULT4A1-1 groups to olanzapine-treated SULT4A1-1 positive subjects. A negative mean difference between the groups indicates greater response for the olanzapine-treated SULT4A1-1 positive patients. Additionally, the effect size (mean difference/standard deviation of pooled sample) is included in this table. The importance of the effect size will be discussed in Example 5. For now, however, take note that the effect sizes are greater than 0.5 suggesting the biomarker is identifying important differences in treatment response.

TABLE 12

Relative Response of Olanzapine-Treated SULT4A1-1 Positive Subjects Compared to Other Groups in CATIE

| Comparison - Olanzapine SULT4A1-1 + | Mean difference[a] (95% CI) | Effect size[b] | P-Value[c] |
|---|---|---|---|
| Vs risperidone SULT4A1-1 + | −20.9 (−33.2 to −6.0) | 0.93 | 0.006 |
| Vs perphenazine SULT4A1-1 + | −14.2 (−29.8 to 1.4) | 0.68 | 0.07 |
| Vs quetiapine SULT4A1-1 + | −14.9 (−28.3 to −1.5) | 0.75 | 0.03 |
| Vs ziprasidone SULT4A1-1 + | −16.1 (−32.7 to 0.5) | 0.77 | 0.06 |
| Vs unsegmented SULT4A1-1 + | −13.0 (−24.7 to −1.2) | 0.60 | 0.03 |
| Vs SULT4A1-1 + except olanzapine | −16.3 (−28.2 to −4.3) | 0.68 | 0.008 |
| Vs olanzapine SULT4A1-1 − | −20.9 (−33.4 to −8.4) | 0.93 | 0.001 |
| Vs unsegmented olanzapine | −15.5 (−27.8 to −3.2) | 0.69 | 0.01 |
| Vs unsegmented (all drugs) | −19.6 (−31.7 to −7.5) | 0.83 | 0.002 |

[a]Mean difference was calculated by subtracting the mean delta PANSS of the comparator group from the mean DELTA PANSS of the olanzapine-treated SULT4A1-1 +group
[b]Effect size was calculated by dividing the mean difference by the standard deviation
[c]P-value was calculated using the T-test for comparison of 2 means C. Time to Discontinuation Statistics Based on Haplotype Status The primary endpoint for the CATIE study was time to discontinuation for all causes (Lieberman et al., 2005). Thus the inventors evaluated the effect of SULT41-1 status on this important parameter. Olanzapine was the superior drug for this endpoint for the sample as a whole (Lieberman et al., 2005).

As shown in Table 13, however, after segmentation by haplotype status, the superiority of olanzapine for time to discontinuation is explained largely by the SULT4A1-1 positive patients. Olanzapine-treated SULT4A1-1 negative patients did not display a statistically significant longer time to discontinuation compared to the same patient group treated with any other drug. Notably, the olanzapine-treated SULT4A1-1 positive subjects had a numerically superior time to discontinuation compared any other group. This difference is significant compared to all of the SULT4A1-1 negative groups with the exception of patients treated with risperidone. The time to discontinuation for SULT4A1-1 positive patients treated olanzapine was also significantly longer than for SULT4A1-1 positive patients treated with perphenazine, risperidone, or all drugs combined.

TABLE 13

Time to Discontinuation in the CATIE Study

| | SULT4A1-1 Positive | | | SULT4A1-1 Negative | | |
|---|---|---|---|---|---|---|
| Drug | N | Months[a] | SD[b] | N | Months[a] | SD[b] |
| Olanzapine | 15 | 14.3 | 6.4 | 43 | 10.0** | 7.3 |
| Perphenazine | 14 | 7.6** | 7.4 | 63 | 10.6* | 7.4 |
| Quetiapine | 18 | 10.3 | 7.5 | 63 | 8.6*** | 7.0 |
| Risperidone | 17 | 8.0*** | 6.0 | 61 | 11.3 | 7.2 |
| Ziprasidone | 10 | 11.7 | 7.0 | 38 | 8.2*** | 6.9 |
| All drugs | 74 | 10.2** | 7.1 | 268 | 9.9** | 7.2 |
| All drugs except Olanzapine | 59 | 9.2** | 7.4 | 225 | 9.7** | 7.2 |

Figure 5:
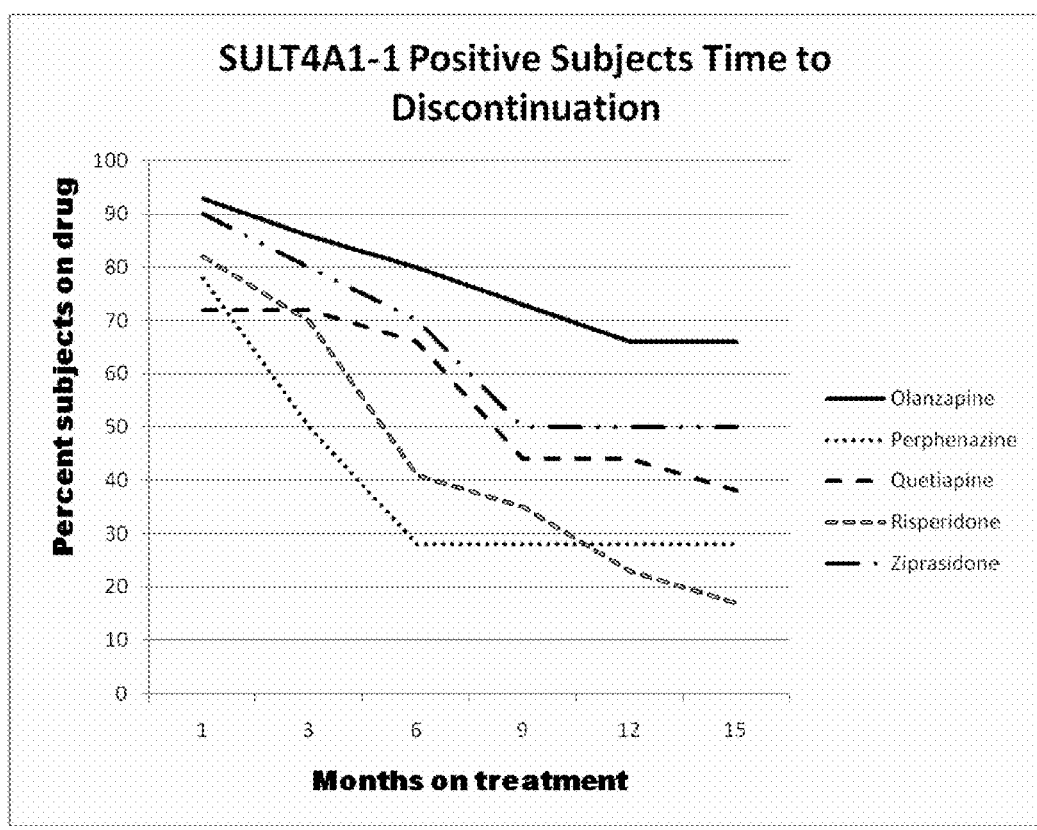
FIG. 5: Percentage of SULT4A1-1 positive patients remaining in phase 1 of the CATIE trial at various time points.
Figure 6:
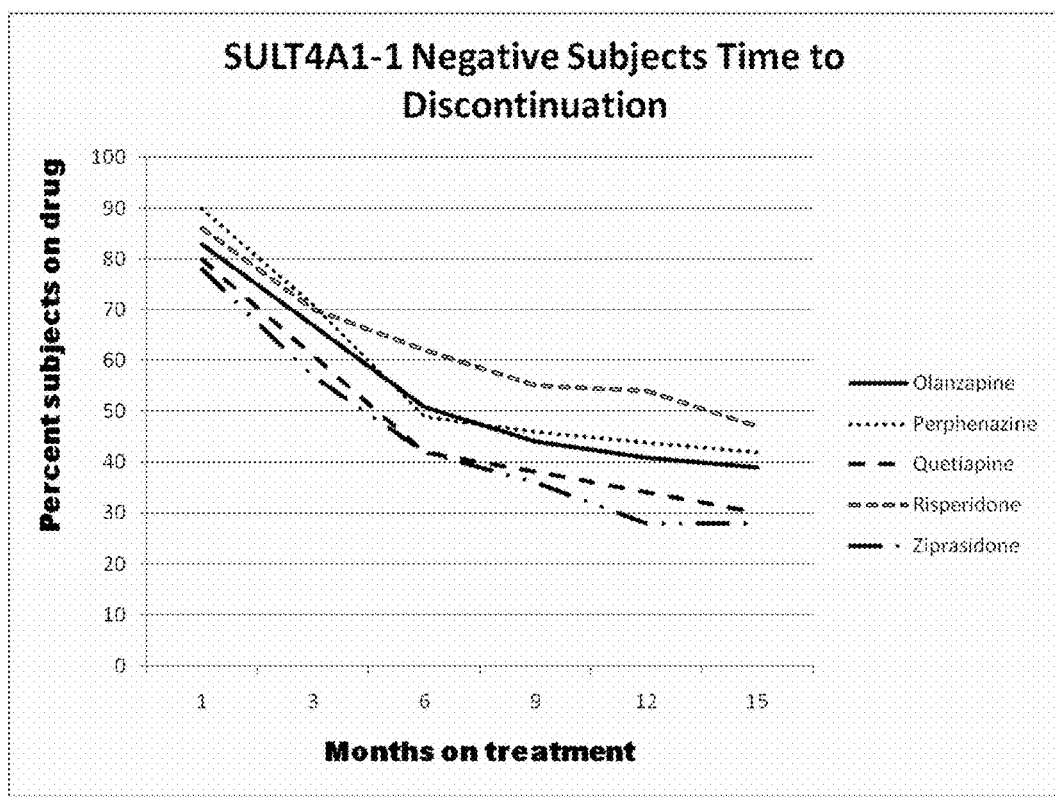
FIG. 6: Percentage of SULT4A1-1 negative patients remaining in phase 1 of the CATIE trial at various time points.

[a]Mean time in months
[b]Standard deviation of the mean
*P < 0.1, P < 0.05, and *P < 0.01 olanzapine-treated SULT4A1-1 positive responded significantly better; P-value calculated using the T-test for comparison of 2 means FIGS. 5 and 6 show the percentage of SULT4A1-1 positive and negative patients, respectively, remaining on the various drugs throughout Phase I of the CATIE study. Note that SULT4A1-1 positive patients tend to stay on olanzapine treatment longer compared to other drugs (FIG. 5). In contrast, this relationship does not hold for SULT4A1-1 negative patients (FIG. 6).

In conclusion, the SULT4A1-1 haplotype identifies a subpopulation, SULT4A1-1 positive patients, having superior response to olanzapine compared to SULT4A1-1 negative patients. Additionally, SULT4A1-1 positive patients respond better to olanzapine than to other antipsychotic drugs. Finally, for SULT4A1-1 negative patients, olanzapine does not demonstrate superiority to other medications. As discussed in Example 5, the superiority of olanzapine for SULT4A1-1 patients exceeds the superiority reported for this drug in a number of key clinical trials. SULT4A1-1 is thus an important biomarker that discriminates between patient subsets who are more or less likely to respond to olanzapine. Testing for this biomarker has the potential to improve treatment decision making in patients who are candidates for antipsychotic drug therapy.

Example 5

Clinical Utility of the Biomarker

The primary rationale for determining the SULT4A1-1 status of a patient is to alter medical practice in some manner. Currently in the psychiatric space, physicians lack useful tools to help them select the most efficacious antipsychotic medication for individual patients. All of the currently approved antipsychotics demonstrated superiority to placebo for treating psychotic symptoms as part of their approval process at the FDA. Examples of comparative effectiveness can be found in any New Drug Approval, e.g. the olanzapine approval package (Zyprexa (olanzapine) Approval Package NDA 20-592. FDA, Center for Drug Evaluation and Research 1996 (Available from: world wide web via accessdata.fda.gov/drugsatfda_docs/nda/96/020592_Original Approval Pkg%20.pdf)). However, a recently published meta-analysis of registration quality clinical trials showed only modest improvements over placebo.

Table 14 shows the results for the atypical antipsychotics used in the CATIE study. The effect size is defined as the difference in the mean response for each drug minus the change in the placebo arm, divided by the standard deviation. In this case, a negative number means a greater improvement in psychopathology, i.e. a greater reduction in PANSS.

Relative to placebo, these drugs had effect sizes ranging from −0.42 to −0.59. For comparison, the same metrics are provided for olanzapine-treated SULT4A1-1 positive patients compared to various other SULT4A1-1-drug combinations from the CATIE study. The effect sizes of the latter ranged from −0.91 to −0.47. To place this in context, the effect size for olanzapine-treated SULT4A1-1 positive vs. SULT4A1-1 negative patients in CATIE was roughly 50% larger (−0.91 vs.-0.59) than the effect size seen when comparing olanzapine to placebo for a population not segment by SULT4A1-1 status.

TABLE 14

Effect Sizes of Atypical Antipsychotics

| Drug | Number of Studies | Effect Size vs. Placebo[c] | Effect Size vs. FGA[d] | Effect Size attributable to SULT4A1−1 status in CATIE |
|---|---|---|---|---|
| Olanzapine | 6 | −0.59 | −0.21 | −0.93[a] |
| Quetiapine | 5 | −0.42 | 0.01 | −0.75[b] |
| Risperidone | 7 | −0.59 | −0.25 | −0.93[b] |
| Ziprasidone | 4 | −0.48 | −0.04 | −0.77[b] |

[a] Olanzapine-treated SULT4A1-1 positive versus olanzapine-treated SULT4A1-1 negative
[b] Olanzapine-treated SULT4A1-1 positive versus "drug"-treated SULT4A1-1 positive
[c] Leucht et al. (2009)
[d] FGA = first generation antipsychotics. Results from Davis et al. (2003).

Currently, clinical practice emphasizes the increased efficacy of atypical antipsychotics over typical antipsychotics. The meta-analysis performed by Davis et al. (2003) examined the efficacy advantage of atypical antipsychotics compared to first generation, or typical, antipsychotics. This analysis revealed a very minor advantage for some of the atypical antipsychotics over typical antipsychotics with effect sizes ranging from −0.25 to 0.01. Only olanzapine and risperidone showed a significant advantage over typical antipsychotics. The effect sizes observed for olanzapine treatment of SULT4A1-1 positive subjects compared to olanzapine treatment of SULT4A1-1 negative patients or other treatment of SULT4A1-1 positive subjects with other drugs is roughly four times that seen when comparing olanzapine or risperidone to first generation antipsychotics.

Therefore, a pharmacogenetic test for SULT4A1-1 haplotype status will offer physicians a tool to identify a subpopulation for which there is a treatment option providing more than twice the efficacy advantage that atypical antipsychotics offer relative to typical antipsychotics.

Another recent meta-analysis compared the effectiveness of the various atypical antipsychotics to each other by using the weighted mean difference in raw PANSS scores. Olanzapine consistently showed modest superiority to quetiapine, risperidone, and Ziprasidone, as shown in Table 15. However, this modest increase in efficacy in unsegmented populations is much smaller than the efficacy improvement observed for the olanzapine-treated SULT4A1-1 positive subjects in the CATIE sample. For example, for SULT4A1-1 positive subjects in CATIE, compared to risperidone, olanzapine demonstrated almost five-times improvement than lower bound of the 95% confidence interval of the meta-analysis comparing the two drugs for unsegmented populations.

In conclusion, segmentation by SULT4A1-1 status identifies a sub-population, SULT4A1-1 positive patients, that demonstrates superior response to olanzapine. Moreover, this superiority exceeds the superiority demonstrated by olanzapine over placebo for unsegmented populations. Conversely, SULT4A1-1 negative patients respond more poorly to olanzapine than do SULT4A1-1 positive subjects. Finally, for the SULT4A1-1 negative patients, olanzapine does not demonstrate superiority over other medications seen in the meta-analysis for patient populations not segmented by SULT4A1-1 status.

TABLE 15

Mean Difference in Total PANSS Score Between Olanzapine and Other Atypical Antipsychotics

| Olanzapine vs. | Meta-analysis[a] | CATIE unsegemented | CATIE SULT4A1-1 + | CATIE SULT4A1-1 − |
|---|---|---|---|---|
| Risperidone | −1.9 (−3.3 to −0.6) | −3.5 | −16 | 0.5 |
| Quetiapine | −3.7 (−5.4 to −1.9) | −6.2 | −12.9 | −3.8 |
| Ziprasidone | −8.3 (−11.0 to −5.6) | −4.9 | −17.9 | −2.1 |

[a]Mean (95% CI) see Leucht et al. (2009).

Example 6

Diagnostic Performance Using Categorical Definitions of Response

Several different measures of diagnostic performance can be used for comparing dichotomous outcomes. Two important metrics include percent positive agreement (PPA), a substitute for sensitivity and percent negative agreement (PNA), a substitute for specificity. Table 16 below presents these measures of diagnostic performance at the 20% decrease in total PANSS threshold in CATIE for olanzapine treatment of SULT4A1-1 positive patients compared to other groups.

TABLE 16

Diagnostic Performance of the SULT4A1-1 Haplotype Test in the CATIE Study Using a 20% decrease in PANSS Threshold

| Comparison[a] | Responder | Non Responder | PPA[b] (95% CI) | PNA[c] (95% CI) | DOR[d] (95% CI) |
|---|---|---|---|---|---|
| Olanzapine | 10 | 5 | 0.50 | 0.87 | 6.60 |
| Olanzapine | 10 | 33 | (0.30 to 0.70) | (0.73 to 0.94) | (1.83 to 23.87) |
| Olanzapine | 10 | 5 | 0.67 | 0.64 | 3.60 |
| Perphenazi | 5 | 9 | (0.42 to 0.85) | (0.39 to 0.84) | (0.78 to 16.66) |
| Olanzapine | 10 | 5 | 0.59 | 0.69 | 3.14 |
| Quetiapine | 7 | 11 | (0.36 to 0.78) | (0.44 to 0.86) | (0.75 to 13.16) |
| Olanzapine | 10 | 5 | 0.77 | 0.74 | 9.33 |
| Rispiradon | 3 | 14 | (0.50 to 0.92) | (0.51 to 0.88) | (1.80 to 48.38) |
| Olanzapine | 10 | 5 | 0.77 | 0.58 | 4.67 |
| Ziprasidon | 3 | 7 | (0.50 to 0.92) | (0.32 to 0.81) | (0.83 to 26.24) |

[a]A plus sign indicates SULT4A1-1 positive and a negative sign indicates SULT4A1-1 negative
[b]Percent Positive Agreement = (true positive)/(true positive + false negative) = SULT4A1-1 positive olanzapine responders/all responders.
[c]Percent Negative Agreement = (true negative)/(true negative + false positive) = SULT4A1-1 negative nonresponders for comparator/all nonresponders
[d]Diagnostic Odds Ratio = (True positive * true negative)/(False positive * false negative)

Example 7

Additional Evidence For Correlation of the SULT4A Haplotype with Baseline Psychopathology and Response to Atypical Antipsychotic in Schizophrenia and Related Disorders Genotype and phenotype data for the CATIE trial were recently made available to qualified researchers through The NIMH Center for Collaborative Genetic Studies on Mental Disorders. The inventors evaluated data for 417 CATIE patients with schizophrenia self reported as having exclusively European ancestry. This same patient population was described in a recent study by Sullivan and coworkers, which confirmed that there is no hidden stratification in the sample (Sullivan et al., 2008).

The CATIE clinical data set included baseline PANSS scores based on clinical assessments prior to initiation of the assigned therapy, but following the washout period for any patients previously on antipsychotic medication. Follow up PANSS data for the CATIE trial were collected at each visit as described in detail by others (Stroup et al., 2003). Briefly, the first visit was after one month of treatment, and subsequent visits were at somewhat irregular intervals of approximately three months for up to a total 18 months or until discontinuation of treatment, whichever came first.

As described above, the inventors evaluated the SULT4A1 gene. The CATIE genotype data included a total of 11 SNPs located between the previously evaluated rs138110, in the promoter region, and the terminal exon of the gene (Brennan and Condra, 2005; Condra et al., 2007; Meltzer et al., 2008). From lowest to highest base pair position on the chromosome the CATIE SNPs were rs138067, rs138079, rs470089, rs2285161, rs2285162, rs2285164, rs2285167, rs470091, rs138099, rs138102, rs138110. As described below, these allowed unambiguous assignment of SULT4A1 haplotype status.

The initial genetic analysis to determine the influence of SULT4A1 haplotypes on quantitative PANSS values was performed using the PLINK 1.03 whole genome analysis toolset developed by Purcell and coworkers (available at pngu.mgh.harvard.edu/purcell/plink/) (Purcell et al., 2007). This software assigns expectation-maximization (EM) algorithm—based haplotypes to each individual. Using these haplotype assignments, PANSS Total scores were analyzed as quantitative traits in PLINK by linear regression.

The inventors used genotype data from the International HapMap project to determine which alleles of rs138097 are associated with each of the six common haplotypes identified by the EM algorithm in PLINK (available via world wide web at hapmap.org/cgi-perl/gbrowse/hapmap). Briefly, ten of the 11 CATIE SNPs (rs138067 being the exception) as well as rs138097 were evaluated in 58 individuals of European ancestry (CEPH Collection) by the HapMap project. Precalculated linkage disequilibrium parameters show that all ten of the other SNPs display D' values of 1.0 with rs138097, each with robust statistical support (LOD scores≧2.7). Furthermore, the inventors evaluated genotypes for the 11 HapMap SNPs using PLINK, and the EM algorithm identified the same six haplotypes that the inventors observed in the CATIE sample, such that a given allele of rs138097 is invariably associated with a specific haplotype (116 agreements out of 116 haplotype assignments).

For all subsequent analyses, the inventors focused on the single haplotype, designated SULT4A1-1. EM algorithm haplotypes were assigned to each patient using HelixTree software (Version 6.4.1; Golden Helix, Bozeman, Mont.), and each individual was scored as being positive or negative for the presence of the haplotype. The inventors assigned SULT4A1-1 haplotype status to those individuals for which EM algorithm assignment could be made with error probabilities of <1%. This included a total of 395 patients from the CATIE study. With the exception of four of the 395 patients in the CATIE study, SULT4A1-1 haplotype status could be assigned with error probabilities of <1×10-5.

To determine the effect of SULT4A1-1 haplotype status on drug response, differences in percent change of PANSS scores from baseline in Phase I of the CATIE trial were analyzed using a linear model with haplotype and drug therapy status as predictors. Since follow-up on subjects was not done at uniform time intervals, analysis was done using the last observation for each patient in treatment Phase I of the trial as the measure of response (last observation carried forward, LOCF). Main effect and interaction terms between the SULT4A1-1 haplotype and drug therapy were included in the linear model. A pre-determined set of contrasts for differences in percent change PANSS by haplotype within each drug therapy (three comparisons) and by drug therapy within each haplotype (six comparisons) were evaluated, with adjustment for multiple-comparisons using the step-up false-discovery rate (FDR) controlling procedure (Benjamini and Hochberg, 1995). A sub-analysis omitting those patients who were randomized to the same antipsychotic drug therapy was also conducted.

The 11 SULT4A1 SNPs genotyped in the CATIE study make up a single haplotype block as determined by Haploview (FIG. 1; Barrett et al., 2005). E-M maximum likelihood phasing of the 11 SNPs from the CATIE study indicated that these markers define only six common haplotypes in Caucasians (Table 3 in Example 2). The haplotype designated SULT4A1-1 occurs at a frequency of 11.6%.

The inventors wanted to test whether the SULT4A1-1 haplotype might relate to pharmacological response for the three atypical antipsychotic drugs that were available for use throughout the CATIE study (olanzapine, quetiapine, and risperidone). As shown in Table 17, patients segregated by SULT4A1-1 haplotype status show differences in percent reduction of PANSS according to the drug therapy received. In particular, SULT4A1-1 positive patients responded better to olanzapine than do SULT4A1-1 negative patients, and SULT4A1-1 positive patients also responded better to olanzapine compared to the other two drugs. For the complete sample, the overall ANOVA F-test for differences in response rate by SULT4A1-1 haplotype/drug therapy was significant (Table 17, top; p=0.035). Pairwise comparisons between SULT4A1-1 positive vs negative patients on olanzapine, SULT4A1-1 positive patients taking olanzapine vs risperidone, and SULT4A1-1 positive patients taking olanzapine vs quetiapine all had significant unadjusted p-values, but did not remain statistically significant after adjustment for the nine comparisons (Table 18, top).

TABLE 17

Relationship of SULT4A1-1 Status to Atypical Antipsychotic Response in CATIE [a]

| Haplotype status | Olanzapine | Risperidone | Quetiapine |
|---|---|---|---|
| Complete Sample | | | |
| SULT4A1-1 + | −20.5 (18.6) N = 17 | −3.52 (18.6) N = 18 | −4.52 (17.6) N = 20 |
| SULT4A1-1 − | −7.44 (22.1) N = 62 | −4.28 (25.1) N = 67 | 0.84 (26.5) N = 63 |
| Patients Randomized to a Different Medication [b] | | | |
| SULT4A1-1 + | −24.55 (17.2) N = 13 | −1.86 (19.8) N = 15 | −6.44 (19.0) N = 16 |
| SULT4A1-1 − | −5.8 (21.7) N = 36 | −4.3 (25.0) N = 55 | 0.4 (26.7) N = 56 |

[a] Percent change from baseline PANSS scores in Phase I of the CATIE study, based on the last observation carried forward (LOCF), means (standard deviation).
[b] Data in the lower half of the table are for the subset of patients who were assigned to a trial arm such that they either switched to a new medication after the washout period or were not previously stabilized on an antipsychotic drug.

TABLE 18

Pair-wise Comparisons for Change in Total PANSS in CATIE Phase I

| Comparison[a] | Difference[b] | 95% CI Lower | 95% CI Upper | P | Adjusted P |
|---|---|---|---|---|---|
| Complete Sample | | | | | |
| Olanzapine, SULT4A1-1+ vs SULT4A1-1− | −13.1 | −25.6 | −0.5 | 0.04 | 0.13 |
| Risperidone, SULT4A1-1− vs SULT4A1-1+ | −0.8 | −13.2 | 11.7 | 0.90 | 0.90 |
| Quetiapine, SULT4A1-1+ vs SULT4A1-1− | −5.4 | −17.4 | 6.7 | 0.37 | 0.57 |
| SULT4A1-1+, Olanzapine vs Risperidone | −17.0 | −32.8 | −1.2 | 0.03 | 0.13 |
| SULT4A1-1+, Quetiapine vs Risperidone | −1.0 | −16.2 | 14.2 | 0.90 | 0.90 |
| SULT4A1-1+, Olanzapine vs Quetiapine | −16.0 | −31.4 | −0.5 | 0.04 | 0.13 |
| SULT4A1-1−, Olanzapine vs Risperidone | −3.2 | −11.4 | 5.1 | 0.44 | 0.57 |
| SULT4A1-1−, Risperidone vs Quetiapine | −5.1 | −13.3 | 3.1 | 0.22 | 0.48 |
| SULT4A1-1−, Olanzapine vs Quetiapine | −7.7 | −25.3 | 9.9 | 0.38 | 0.57 |
| Patients Randomized to a Different Medication[c] | | | | | |
| Olanzapine, SULT4A1-1+ vs SULT4A1-1− | −18.8 | −25.6 | −0.5 | 0.015 | 0.07 |
| Risperidone, SULT4A1-1− vs SULT4A1-1+ | −2.5 | −16.3 | 11.4 | 0.72 | 0.77 |
| Quetiapine, SULT4A1-1+ vs SULT4A1-1− | −6.8 | −20.3 | 6.6 | 0.31 | 0.47 |
| SULT4A1-1+, Olanzapine vs Risperidone | −22.7 | −40.6 | −4.7 | 0.012 | 0.07 |
| SULT4A1-1+, Quetiapine vs Risperidone | −4.6 | −21.6 | 12.4 | 0.59 | 0.77 |
| SULT4A1-1+, Olanzapine vs Quetiapine | −18.1 | −35.8 | −0.4 | 0.04 | 0.13 |
| SULT4A1-1−, Olanzapine vs Risperidone | −1.5 | −11.7 | 8.7 | 0.77 | 0.77 |
| SULT4A1-1−, Risperidone vs Quetiapine | −4.7 | −13.7 | 4.3 | 0.30 | 0.47 |
| SULT4A1-1−, Olanzapine vs Quetiapine | −11.9 | −32.3 | 8.5 | 0.24 | 0.46 |

[a] Comparisons are listed such that the group showing superior performance is given first.
[b] Difference in percent change in PANSS score for the first group minus that for the second group. The negative values (larger decrease in PANSS score) correspond to a greater response for the first group.
[c] Data in the lower half of the table are for the subset of patients who were assigned to a trial arm such that they either switched to a new medication after the washout period or were not previously stabilized on an antipsychotic drug.

The inventors examined patient sex, age and age of onset as possible confounders for drug response. Adjusting for patient age, age of onset, and gender in the linear model did not markedly alter the estimated differences in percent reduction of PANSS by drug therapy and SULT4A1-1 haplotype (Table 19, top). In particular, the results for the differences with significant unadjusted p-values in Table 18 were not altered.

The inventors evaluated the feasibility of replicating these findings using the CATIE Phase II data, in which non-responders were subsequently treated with a different drug. Phase II cannot be considered an exact replication of Phase I because the patient population in Phase II is expected to be enriched for individuals who are resistant to treatment by any antipsychotic drug. Indeed, improvement in PANSS scores

TABLE 19

Pair-wise Comparisons for Change in Total PANSS in CATIE Phase I Corrected for Age, Age of Onset and Sex

| Comparison [a] | Differ-ence [b] | 95% CI Lower | 95% CI Upper | P value | Adj. P value |
|---|---|---|---|---|---|
| Olanzapine, SULT4A1-1 + vs SULT4A1-1 − | −13.96 | −25.62 | −0.50 | 0.03 | 0.10 |
| Risperidone, SULT4A1-1 − vs SULT4A1-1 + | −2.48 | −15.52 | 10.55 | 0.70 | 0.79 |
| Quetiapine, SULT4A1-1 + vs SULT4A1-1 − | −2.65 | −15.20 | 9.91 | 0.67 | 0.79 |
| SULT4A1-1 +, Olanzapine vs Risperidone | −18.67 | −35.31 | −2.03 | 0.03 | 0.10 |
| SULT4A1-1 +, Quetiapine vs Risperidone | −0.54 | −16.53 | 15.45 | 0.95 | 0.95 |
| SULT4A1-1 +, Olanzapine vs Quetiapine | −18.14 | −34.21 | −2.06 | 0.03 | 0.10 |
| SULT4A1-1 −, Olanzapine vs Risperidone | −2.23 | −10.52 | 6.06 | 0.59 | 0.79 |
| SULT4A1-1 −, Risperidone vs Quetiapine | −4.60 | −12.97 | 3.78 | 0.27 | 0.49 |
| SULT4A1-1 −, Olanzapine vs Quetiapine | −11.31 | −29.43 | 6.82 | 0.21 | 0.48 |

Patients Randomized to a Different Medication [c]

| Comparison | Differ-ence | 95% CI Lower | 95% CI Upper | P value | Adj. P value |
|---|---|---|---|---|---|
| Olanzapine, SULT4A1-1 + vs SULT4A1-1 − | −19.07 | −25.62 | −0.50 | 0.02 | 0.06 |
| Risperidone, SULT4A1-1 − vs SULT4A1-1 + | −5.14 | −19.83 | 9.55 | 0.49 | 0.73 |
| Quetiapine, SULT4A1-1 + vs SULT4A1-1 − | −2.91 | −16.84 | 11.03 | 0.68 | 0.80 |
| SULT4A1-1 +, Olanzapine vs Risperidone | −25.03 | −44.22 | −5.83 | 0.01 | 0.06 |
| SULT4A1-1 +, Quetiapine vs Risperidone | −3.33 | −21.26 | 14.59 | 0.71 | 0.80 |
| SULT4A1-1 +, Olanzapine vs Quetiapine | −21.69 | −40.20 | −3.19 | 0.02 | 0.06 |
| SULT4A1-1 −, Olanzapine vs Risperidone | −0.82 | −11.02 | 9.39 | 0.87 | 0.87 |
| SULT4A1-1 −, Risperidone vs Quetiapine | −4.71 | −13.99 | 4.57 | 0.31 | 0.56 |
| SULT4A1-1 −, Olanzapine vs Quetiapine | −16.17 | −37.32 | 4.98 | 0.13 | 0.29 |

[a] Comparisons are listed such that the group showing superior performance is given first.
[b] Difference in percent change in PANSS score for the first group minus that for the second group. The negative values (larger decrease in PANSS score) correspond to a greater response for the first group.
[c] Data in the lower half of the table are for the subset of patients who were assigned to a trial arm such that they either switched to a new medication after the washout period or were not previously stabilized on an antipsychotic drug.

To remove total length of time on drug treatment as potential confounding variable, the inventors additionally carried out analysis of only those patients who switched to a new medication or had not previously been on an antipsychotic medication prior to enrollment in the CATIE study. Those who were randomized to the same medication may or may not have reached a steady state in their response to that particular treatment, in which case, the clinical response during the trial might be complicated by effects relating to the total length of time on the drug and not a drug effect per se. Also, by looking only at the subgroup randomized to a different medication, the inventors are able to assess drug effects during the process of switching to a medication that patients are not currently taking.

When considering this subset of patients, the differences in percent reduction of PANSS by drug therapy and SULT4A1-1 haplotype are more pronounced (Table 17, bottom). The overall ANOVA F-test was again significant (p=0.037). Comparisons between SULT4A1-1 positive vs negative patients on olanzapine, SULT4A1-1 positive patients taking olanzapine vs risperidone, and SULT4A1-1 positive patients taking olanzapine vs. quetiapine again all had significant unadjusted p-values, with the former two having marginal significance (p=0.07) after adjustment for multiple comparisons (Table 18, bottom). Adjustment for patient age, age of onset, and gender again did not impact the results (Table 19, bottom).

was less pronounced for all groups in Phase II (Table 20). Data were available for too few patients in Phase II for statistical analyses to be valid for the SULT4A1-1 positive group. However, for Phase II, SULT4A1-1 positive patients did respond somewhat better than the SULT4A1-1 negative patients to olanzapine. Also, this group displayed more improvement on olanzapine compared to either risperidone or quetiapine.

TABLE 20

CATIE Phase I non-responders last observation carry forward for Phase II (decrease PANSS ≧ 20%)

| Drug | SULT4A1-1 Status | Responders | Nonresponders | % Responders |
|---|---|---|---|---|
| Olanzapine | Positive | 3 | 4 | 42.9 |
| Olanzapine | Negative | 3 | 14 | 17.6 |
| Risperidone | Positive | 0 | 1 | 0 |
| Risperidone | Negative | 4 | 8 | 33.3 |
| Quetiapine | Positive | 0 | 1 | 0 |
| Quetiapine | Negative | 1 | 10 | 9.0 |

Example 8

Risk Management Involving SULT4A1-1 Test

The SULT4A1-1 test, as well as any test including a SULT4A1-1 haplotype determination, will be used in the risk-benefit analysis for prescribing atypical antipsychotics—olanzapine in particular. The highly variable efficacy of olanzapine and moderate to large side effect burden create an opportunity to greatly enhance patient care and usefulness of olanzapine when combined with the SULT4A1-1 haplotype test.

Figure 7:
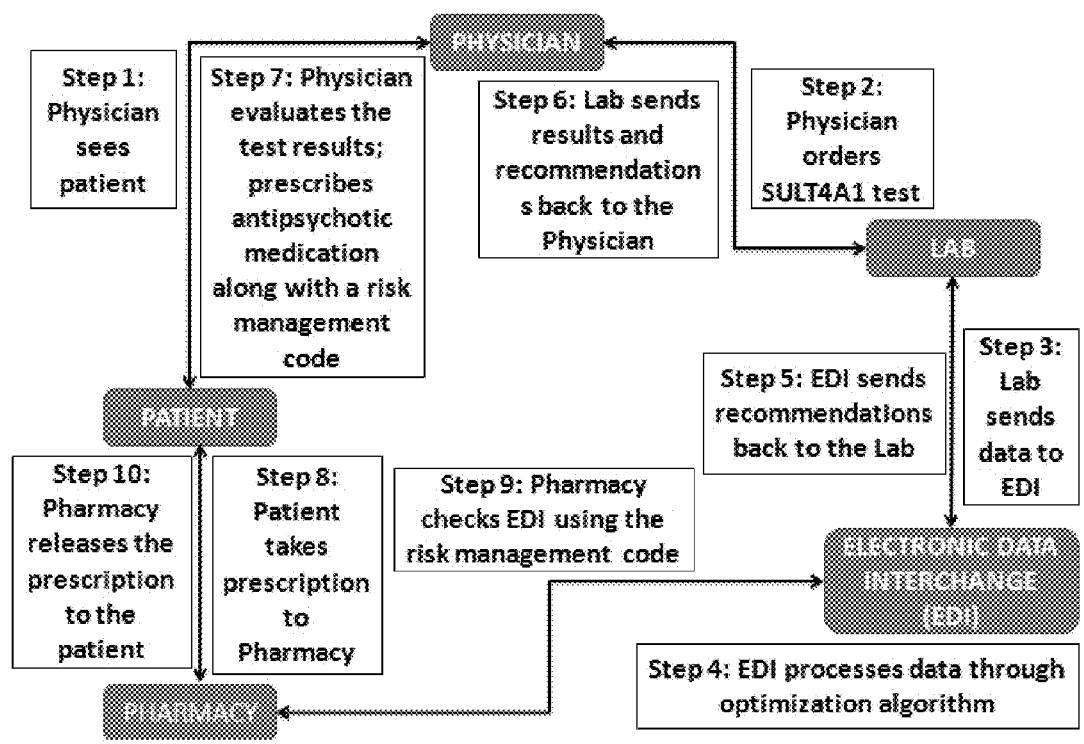
FIG. 7: An exemplary embodiment of risk management involving SULT4A1-1 determination.

The risk management program (an embodiment illustrated in FIG. 7) has the potential of becoming an FDA-mandated safety program for prescribing olanzapine vs. risperidone. By incorporating the SULT4A1-1 haplotype determination into an electronic data exchange that interfaces with physicians, pharmacies labs and patients, this invention may be applied to guide all of the four groups involved in selection of and dispensing of olanzapine utilizing information that will optimize potential therapeutic benefits (such as optimal efficacy and improvement of symptoms) and minimize potential risks (such as lack of drug effect and risks associated with lack of drug effect like hospitalization and worsening of symptoms).

Example 9

Single SNP Determination for SULT4A1-1 Haplotype

Using the International HapMap Project resources (www.hapmap.org), the inventors downloaded pre-computed haplotypes for the SULT4A1 gene. Using the precomputed haplotypes, the inventors identified SNP alleles associated with the SULT4A1-1 haplotype using the algorithm specified previously. The inventors searched for single SNPs that uniquely identified that haplotype and were able to identified rs763120 (the SNP is at position 31 at SEQ ID NO:15), C allele, as meeting that criterion. Subsequently the inventors used a sample of several hundred DNAs to confirm that the C allele of rs763120 indeed marks the SULT4A1-1 haplotype. Therefore, as one example, rs763120 can be used as a single SNP test to tag the SULT4A1-1 haplotype.

Example 10

Segmentation by SULT4A1-1 Status Predicts Differential Response to Risperidone The CATIE clinical data set included Clinical Global Impression (CGI) Scale, an observer-provided assessment of the psychiatric health of the patient (Stroup et al., 2003; Guy 1976). Patients are rated with the CGI Scale from 1 to 7, with higher scores indicating greater severity of illness. The CATIE study provided a response variable that measured the time (in months) of successful treatment as measured by the CGI scale ("TMSUCC1" in the CATIE data).

Using SULT4A1-1 status based on evaluation of the CATIE genotype data (see Example 3), the inventors tested if SULT4A1-1 status can be used to predict the length of time for successful treatment with risperidone as measured by the CGI scale. Using this metric, as can be seen in Table 21, SULT4A1-1 negative patients on risperidone have a higher average number of months of successful treatment (6.88 months) than do SULT4A1-1 positive patients on risperidone (1.76 months) with a p-value of 0.001. Furthermore, SULT4A1-1 positive patients show a shorter time of successful treatment when treated with risperidone compared to treatment with any of the other antipsychotic drugs.

TABLE 21

SULT4A1-1 Status Relates to Length of Successful Treatment with risperidone (CGI Months)

| Drug | Unsegmented | | | SULT4A1-1 positive | | | SULT4A1-1 negative | | | |
|---|---|---|---|---|---|---|---|---|---|---|
| | $N^a$ | Mean | $SD^b$ | $N^a$ | Mean | $SD^b$ | $N^a$ | Mean | $SD^b$ | P-val |
| Olanzapine | 93 | 6.10 | 6.44 | 21 | $8.33^d$ | 7.00 | 72 | 5.44 | 6.17 | 0.070 |
| Perphenazine | 79 | 6.72 | 7.26 | 14 | 5.29 | 6.89 | 65 | 7.03 | 7.35 | 0.419 |
| Quetiapine | 97 | 4.65 | 6.14 | 24 | $5.96^c$ | 6.75 | 73 | 4.22 | 5.91 | 0.230 |
| Risperidone | 98 | 5.79 | 6.61 | 21 | 1.76 | 4.01 | 77 | 6.88 | 6.77 | 0.001 |
| Ziprasidone | 50 | 5.36 | 6.17 | 11 | $8.36^d$ | 7.49 | 39 | 4.51 | 5.56 | 0.067 |

$^a$N corresponds to the number of samples.
$^b$SD corresponds to standard deviation.
$^c$Statistically significant difference in comparison with SULT4A1-1 positive risperidone with p-value < 0.05
$^d$Statistically significant difference in comparison with SULT4A1-1 positive risperidone with p-value < 0.005

Example 11

SULT4A1-1 Positive Patients have an Elevated Risk of Discontinuation when Treated with Risperidone Discontinuation of antipsychotic drug use is a major risk factor for antipsychotic drugs and can adversely impact the safety profile of these medications. Using the CATIE data, the inventors have shown that SULTA1-1 haplotype status relates to the risk of discontinuing use of risperidone. For the analyses shown in Tables 22-24, SULT4A1-1 haplotype status was assigned as describe in Example 3, and standard statistical survival analysis using Cox's proportional hazards model was used to determine the relative risk (hazard) of discontinuing drug use. The Hazard Ratio (HR) measures the risk of an event (in this case, switching or discontinuation from the drug) relative to patient exposure or status (in this case, SULT4A1-1 positive status). Hence, for example, a HR of 2 means that SULT4A1-1 positive patients are twice as likely to discontinue when compared to SULT4A1-1 negative patients, while a HR of 0.5 means that SULT4A1-1 positive patients have 50% lower risk of discontinuation compared to SULT4A1-1 negative patients.

When treated with risperidone, SULT4A1-1 positive patients have an elevated risk of discontinuation as measured by all-cause discontinuation. As can be seen in Table 22, SULT4A1-1 positive patients treated with risperidone have an elevated risk of discontinuing drug use for all-causes (HR=1.74) as compared to the SULT4A1-1 negative patients treated with risperidone.

TABLE 22

Hazard of All-Cause Discontinuation in the CATIE Study

| Comparison | HR | 95% CI[c] | P-value |
|---|---|---|---|
| Unsegmented risperidone/ Unsegmented all other drugs | 0.91[a] | (0.68, 1.23) | 0.54 |
| SULT4A1-1 negative risperidone/ SULT4A1-1 negative all other drugs | 0.79[a] | (0.56, 1.12) | 0.18 |
| SULT4A1-1 positive risperidone/ SULT4A1-1 positive all other drugs | 1.48[a] | (0.82, 2.6) | 0.189 |
| SULT4A1-1 positive risperidone/ SULT4A1-1 negative risperidone | 1.74[b] | (0.98, 3.11) | 0.06 |

[a]The Hazard Ratio (HR) of patient population on risperidone/those on other antipsychotics.
[b]The Hazard Ratio (HR) of SULT4A1-1 positive patient population on risperidone/SULT4A1-1 negative patient population on risperidone.
[c]The data represents 95% confidence interval for the measured Hazard Ratio (HR).

SULT4A1-1 positive patients treated with risperidone have an elevated risk of discontinuation due to lack of efficacy. As can be seen in Table 23, SULT4A1-1 positive patients treated with risperidone have an elevated risk of discontinuing drug use due to lack of efficacy (HR=1.94) as compared to the SULT4A1-1 negative patients treated with risperidone. Similarly, SULT4A1-1 positive patients treated with risperidone have an elevated risk of discontinuation due to lack of efficacy (HR=2.36) as compared to SULT4A1-1 positive patients treated with other antipsychotics

TABLE 23

Hazard of Discontinuation Due to Lack of Efficacy in the CATIE Study

| Comparison | HR | 95% CI[c] | P-value |
|---|---|---|---|
| Unsegmented risperidone/ Unsegmented all other drugs | 1.09[a] | (0.72, 1.65) | 0.673 |
| SULT4A1-1 negative risperidone/ SULT4A1-1 negative all other drugs | 0.88[a] | (0.55, 1.43) | 0.608 |
| SULT4A1-1 positive risperidone/ SULT4A1-1 positive all other drugs | 2.36[a] | (1.02, 5.57) | 0.044 |
| SULT4A1-1 positive risperidone/ SULT4A1-1 negative risperidone | 1.94[b] | (0.89, 4.25) | 0.095 |

[a]The Hazard Ratio (HR) of patient population on risperidone/those on other antipsychotics.
[b]The Hazard Ratio (HR) of SULT4A1-1 positive patient population on risperidone/SULT4A1-1 negative patient population on risperidone.
[c]The data represents 95% confidence interval for the measured Hazard Ratio (HR).

SULT4A1-1 positive patients treated with risperidone have elevated risk of discontinuation due to treatment emergent side effects. As shown in Table 24, SULT4A1-1 positive patients treated with risperidone have an elevated risk of discontinuation due to treatment emergent side effects (HR=2.2) as compared to SULT4A1-1 negative patients treated with risperidone. Further, SULT4A1-1 negative patients treated with risperidone have lower risk of discontinuation due to treatment emergent side effects (HR=0.47) as compared to SULT4A1-1 negative patients treated with other antipsychotics.

TABLE 24

Hazard of Discontinuation Due to Treatment Emergent Side Effects in the CATIE Study

| Comparison | HR | 95% CI[c] | P-value |
|---|---|---|---|
| Unsegmented risperidone/ Unsegmented all other drugs | 0.52[a] | (0.28, 0.97) | 0.0387 |
| SULT4A1-1 negative risperidone/ SULT4A1-1 negative all other drugs | 0.47[a] | (0.22, 0.98) | 0.044 |
| SULT4A1-1 positive risperidone/ SULT4A1-1 positive all other drugs | 0.73[a] | (0.25, 2.16) | 0.573 |
| SULT4A1-1 positive risperidone/ SULT4A1-1 negative risperidone | 2.2[b] | (0.65, 7.21) | 0.21 |

[a]The Hazard Ratio (HR) of patient population on risperidone/those on other antipsychotics.
[b]The Hazard Ratio (HR) of SULT4A1-1 positive patient population on risperidone/SULT4A1-1 negative patient population on risperidone.
[c]The data represents 95% confidence interval for the measured Hazard Ratio (HR).

Example 12

SULT4A1-1 Negative Patients have an Elevated Risk of Discontinuation Due to Treatment-Emergent Adverse Events (TAES) When Treated with Olanzapine The published results from the CATIE Study agree with previous findings that olanzapine has both a higher efficacy and a higher burden of weight gain and metabolic side-effect than the other antipsychotics (Lieberman et al. 2005). Specifically, the CATIE consortium found that olanzapine treated patients stayed on the drug longer, had few discontinuations for lack of efficacy, and had a higher incidence of clinically significant weight gain compared to patients treated with other drugs. Interestingly, despite the higher incidence of weight gain, olanzapine was not inferior to the other drugs, with exception of risperidone, in time to discontinuation for intolerability, suggesting that physicians found the weight gain manageable in light of the efficacy of the drug.

The CATIE data yielded safety information in the form of treatment-emergent adverse events (TAEs) that can be used in conjunction with SULT4A1-1 status to impact the risk/benefit profile of using olanzapine. Specifically, the inventors have shown that SULT4A1-1 negative status predicts an elevated risk of discontinuing use due to TAE's for patients treated with olanzapine. All of the drugs studied in CATIE have significant side-effect burdens. Thus, an important outcome measure was time to discontinuation for TAE. While the various TAEs are traditional safety measures that are reflected in the existing drug labels, segmentation by SULT4A1-1 haplotype status produces special subpopulations for which the rates and/or severity of the TAE are altered and for which new label language may be appropriate (e.g., as seen for the drug metabolism enzymes). Accordingly, segmentation by SULT4A1-1 status can lead to an altered risk/benefit profile.

To demonstrate the impact of SULT4A1-1 haplotype status on time to discontinuation for TAEs, SULT4A1-1 haplotype status was assigned as describe in Example 3, and standard statistical survival analysis using Cox's proportional hazards model was used to determine the relative risk (hazard) of discontinuing drug use was performed as described in Example 11. As describe in Example 11, Hazard Ratio (HR) measures the risk of an event (in this case, switching or discontinuation from the drug) relative to patient exposure or status (in this case, SULT4A1-1 status).

Table 25 shows how segmentation by SULT4A1-1 status impacts the risk that olanzapine treated patients experience a TAE that forced a discontinuation of therapy. For the unsegmented patient population olanzapine has a higher risk of TAEs compared to the other drugs in CATIE (HR=1.6). However, segmentation by SULT4A1-1 status reveals that the enhanced risk is attributable to the SULT4A1-1 negative patients (HR=2.0) and not to SULT4A1-1 positive patients (HR<1.0). Therefore, by this measure, olanzapine is less safe than other drugs for the SULT4A1-1 negative patients, but not for SULT4A1-1 positive patients.

TABLE 25

Hazard of Discontinuation Due to TAEs for Olanzapine in the CATIE Study

| Comparison | HR | 95% CI[C] | P-value |
|---|---|---|---|
| Unsegmented olanzapine/ Unsegmented all other drugs | 1.6[a] | (0.94, 2.7) | 0.08 |
| SULT4A1-1 negative olanzapine/ SULT4A1-1 negative all other drugs | 2.0[a] | (1.1, 3.6) | 0.03 |
| SULT4A1-1 positive olanzapine/ SULT4A1-1 positive all other drugs | 0.85[a] | (0.28, 2.6) | 0.77 |
| SULT4A1-1 positive olanzapine/ SULT4A1-1 negative olanzapine | 0.67[b] | (0.2, 2.0) | 0.48 |

[a]The Hazard Ratio (HR) of patient population on olanzapine/those on other antipsychotics including risperidone, quetiapine, ziprasidone, and perphenazine
[b]The Hazard Ratio (HR) of SULT4A1-1 (+) positive patient population on olanzapine/ SULT4A1-1 (−) positive patient population on olanzapine.
[C]The data represent 95% confidence interval for the measured Hazard Ratio (HR).

Example 13

SULT4A1-1 Negative Patients have an Elevated Risk of Hospitalization for Psychosis when Treated with Quetiapine A. Correlation of Haplotype Status with Hospitalization Due to Exacerbation of Psychosis Schizophrenia is a life-long, chronic illness. Often patients cycle between periods of well managed disease and periods of relapse or exacerbation of psychosis. One of the main goals of antipsychotic therapy is to prevent relapses of psychosis. Indeed, all of the atypical antipsychotics used in the CATIE trial have specific label claims for the maintenance of response. When the disease becomes uncontrolled, these relapses often lead to hospitalization. In CATIE, the average duration of a hospital stay was 15.2 days incurring inpatients costs of ~$12,600 per stay, representing a significant burden on both the patient and the healthcare system. Additionally, during the relapse period, schizophrenics are at increased risk for harm to self and others. While relapse and hospitalization are known risks associated with the treatment failure for schizophrenia, identification of special populations for which the rate or risk of these events is altered constitutes new safety information.

To assess if SULT4A1-1 status impacts the risk of hospitalization in Caucasians, the inventors assigned SULT4A1-1 status to each CATIE subject and evaluated hospitalization events due to exacerbation of psychosis. For this analysis, the inventors assigned a dichotomous value (positive or negative) for hospitalization status to subjects in each phase of the trial based on only the first hospitalization event for a given patient in that phase. Patients participating in Phases 1, 2, and/or 3 were included in the totals for the appropriate drug. Table 26 shows the results of that analysis.

TABLE 26

SULT4A1-1 Status and Rate of Hospitalization (HOSP)

| Drug | Unsegmented | | SULT4A1-1 negative | | SULT4A1-1 Positive | | P-value[1] |
|---|---|---|---|---|---|---|---|
| | N | HOSP | N | HOSP | N | HOSP | |
| Olanzapine | 162 | 23 (14.2%) | 124 | 22 (17.7%) | 38 | 1 (2.6%) | 0.016 |
| Perphenazine | 81 | 10 (12.3%) | 67 | 9 (13.4%) | 14 | 1 (7.1%) | 1.0 |
| Quetiapine | 157 | 25 (15.9%) | 123 | 24 (19.5%) | 34 | 1 (2.9%) | 0.017 |
| Risperidone | 159 | 20 (12.6%) | 123 | 16 (13%) | 36 | 4 (11.1%) | 1.0 |
| Ziprasidone | 110 | 13 (11.8%) | 82 | 11 (13.4%) | 28 | 2 (7.1%) | 0.51 |
| Total | 669 | 91 (13.6%) | 518 | 82 (15.8%) | 150 | 9 (6%) | 0.002 |

[1]Fisher's exact test comparing SULT4A1-1 negative to SULT4A1-1 positive subjects for each drug As can be seen, for all drugs, SULT4A1-1 negative patients are more likely than SULT4A1-1 positive patients to be hospitalized for psychosis. This finding is statistically significant for the patient population as a whole as well as for olanzapine and quetiapine individually. SULT4A1-1 negative subjects treated with olanzapine had significantly higher likelihood of hospitalization (17.7%) than did SULT4A1-1 positive subjects treated with olanzapine (2.6%). Similarly, SULT4A1-1 negative subjects treated with quetiapine had significantly higher likelihood of hospitalization (19.5%) than did SULT4A1-1 positive subjects treated with quetiapine (2.9%).

Given the frequency and severity of this adverse event, subpopulations with elevated rates of hospitalization constitute an unexpected safety signal and that could provide valuable information for treating physicians. Indeed, as Table 26 shows, for the unsegmented population overall, hospitalization due to exacerbation of psychosis occurred at a high rate for a serious adverse event (13.6%).

B. Kaplan-Meier Survival Analysis

Figure 8:
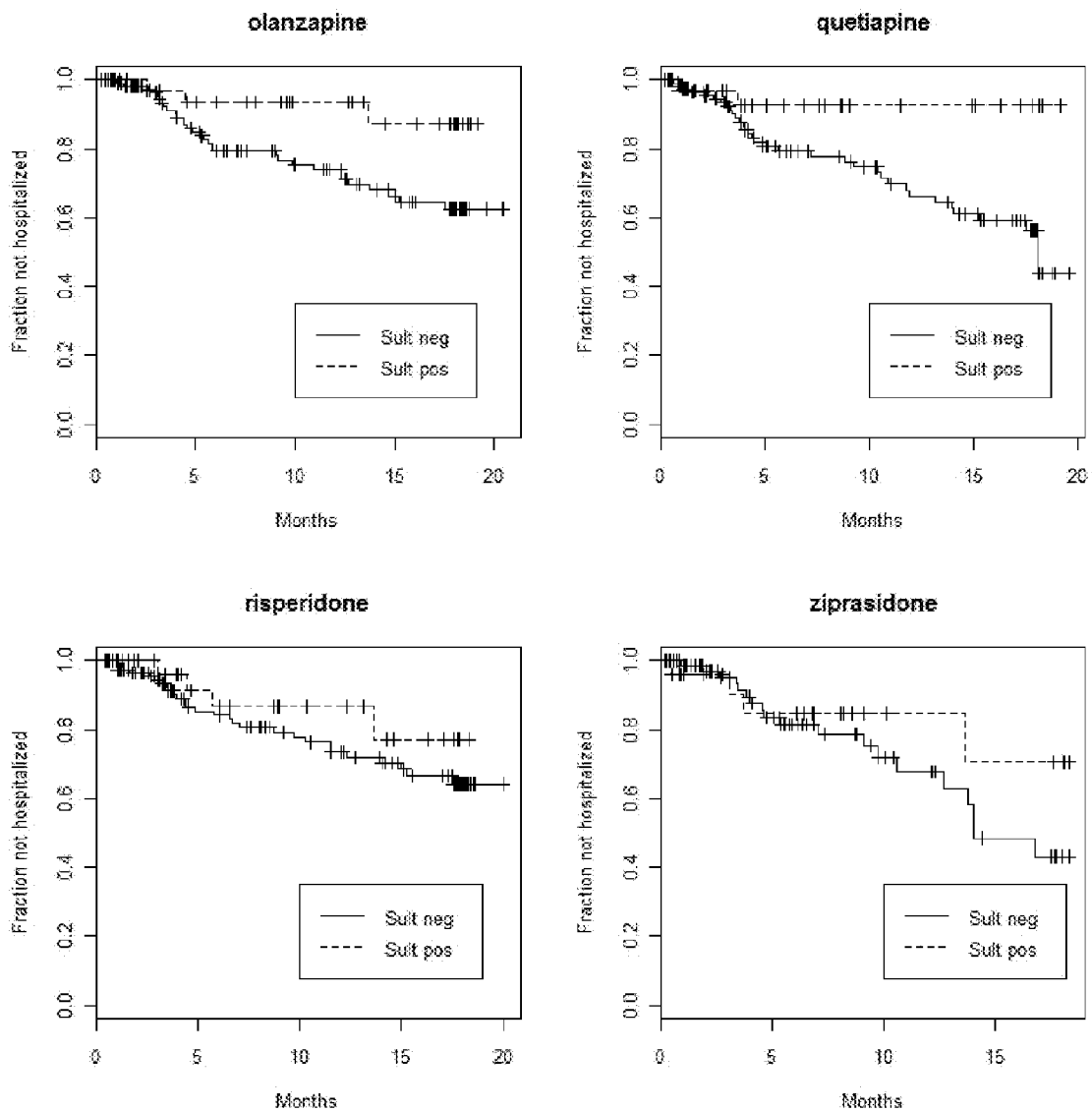
FIG. 8: Kaplan-Meier survival curves for the SULT4A1-1 negative and SULT4A1-1 positive patient populations. Each plot corresponds to an individual atypical antipsychotic in the CATIE trial. The curves model the fraction of the trial population that will not have a hospitalization event as a function of time. Survival fractions are adjusted for the number of subjects remaining in the trial at each time point. Vertical slashes correspond to patients discontinuing the drug, either due to drug switching or stopping participation in the trial.

A Kaplan-Meier survival analysis was performed to determine whether there was a difference between the survival (hospitalization) rates for the SULT4A1-1 negative and SULT4A1-1 positive patient populations treated with each of the atypical antipsychotics. Survival plots model the fraction of the population that survived (i.e., no hospitalization event) as a function of time. There was a significant difference between the survival rates for olanzapine (P=0.029) and quetiapine (P=0.016) patients, with SULT4A1-1 negative patients showing a decreasing survival rate with time as compared to the SULT4A1-1 positive patients. This suggests that SULT4A1-1 negative patients on olanzapine or quetiapine have a higher likelihood of hospitalization with time as compared to the SULT4A1-1 positive patients. While similar trends were observed for patients treated with risperidone (P=0.299) or ziprasidone (P=0.326), the difference between the SULT4A1-1 negative and SULT4A1-1 positive populations was not statistically significant. These results are shown graphically in FIG. 8.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,143,854
U.S. Pat. No. 5,288,514
U.S. Pat. No. 5,288,644
U.S. Pat. No. 5,384,261
U.S. Pat. No. 5,424,186
U.S. Pat. No. 5,491,224
U.S. Pat. No. 5,510,270
U.S. Pat. No. 5,527,681
U.S. Pat. No. 5,776,688
U.S. Pat. No. 5,837,832
U.S. Pat. No. 5,858,659
U.S. Patent Publn. 2003/0108938
U.S. Patent Publn. 2004/0014095
Albertson et al., *Breast Cancer Res. Treat.*, 78:289-298, 2003.
Alderborn et al., *Genome Research*, 10(8):1249-1258, 2000.
American Psychiatric Association. Diagnostic and Statistical Manual of Mental Disorders, 4$^{th}$ Ed., Washington, D.C.: American Psychiatric Association, 1994.
Ausubel et al., In: *Current Protocols in Molecular Biology*, John Wiley & Sons, NY, 631-636, 2003.
Baker et al., *Biol. Psychiatry*, 58(1):23-31, 2005.
Barrett et al., *Bioinformatics*, 21:263-265, 2005.
Benjamini and Hochberg, *J. R. Statist. Soc. B.*, 57:289-300, 1995.
Brennan and Condra, *Am. J. Med. Genet. B Neuropsychiatr. Genet.*, 139(1):69-72, 2005.
Cadenhead, *Psychiatric Clinics of North America*, 25(4):837-53, 2002.
Callicott et al., *Proc. Natl. Acad. Sci. USA*, 102(24):8627-32. 2005.
Cannon et al., *Arch. Gen. Psychiatry*, 62(11):1205-13, 2005.
Chen et al., *Genome Research*, 9(5):492-498, 1999.
Church and Gilbert, *Proc. Natl. Acad. Sci. USA*, 81:1991-1995, 1988.
Condra et al., *Psychiatric Genetics*, 17:292-298, 2007.
Cotton et al., *Proc. Natl. Acad. Sci. USA*, 85:4397-4401, 1985.
Davis et al, *Arch. Gen. Pysch.*, 60:553-564, 2003
Diagnostic and Statistical Manual of Mental Disorders, Fourth Edition, Text Revision, American Psychiatric Association, 2000.
Eckert et al., *PCR Methods and Applications*, 1(1):17-24, 1991.
Eichelbaum et al., *Clin. Exp. Pharmacol. Physiol.*, 23:983-985. 1996.
Everitt and Rabe-Hesketh, In: *Analyzing Medical Data Using S-PLUS*, Springer, 2001.
Flavell et al., *Cell*, 15:25, 1978.
Geever et al., *Proc. Natl. Acad. Sci. USA*, 78:5081, 1981.
GeneChip® Human Mapping 500K Array Set. Affymetrix, Inc. URL: available via world wide web at.affymetrix.com/products services/arrays/specific/500k.affx, 2009.
Gornick et al., *J. Autism Dev. Disord.*, 1-8, 2005.
Gothelf et al., *Nat. Neurosci.*, 8(11):1500-2, 2005.
Gottesman and Gould, *Amer. J. Psychiatry*, 160(4):636-45, 2003.
Guatelli et al., *Proc. Nat. Acad. Sci. USA*, 87:1874, 1990.
Guy, *ECDEU Assessment Manual for Psychopharmacology*, Rockville, Md., U.S. Dept. Health, Education, and Welfare, 1976.
Hallmayer et al., *Am. J. Hum. Genet.*, 77(3):468-76, 2005.
Heinrichs, *Neurosci. Biobehavioral Rev.*, 28(4):379-94, 2004.
Kay et al., *Br. J. Psychiatry Suppl.*, 59-67, 1989.
Kay et al., *Schizophr. Bull.*, 13:261-276, 1987.
Kay, *Positive and Negative Syndromes in Schizophrenia*, Routledge, 1991.
Kendler et al., *Am. J. Psychiatry*, 152(5):749-54, 1995.
Klein et al., *Proc. Natl. Acad. Sci. USA*, 96:4494-4499, 1999.
Kwoh et al., *Proc. Natl. Acad. Sci. USA*, 86:1173, 1989.
Iali-Hassani et al., *PLoS Biol.*, 5(5):e97, 2007.
Landegren et al., *Science*, 241:1077, 1988.
Leucht et al., *Mol. Psychiatry*, 14(4):429-47, 2009.
Leucht et al., *Schizophr. Res.*, 79:231-238, 2005.
Lieberman et al., *N. Engl. J. Med.*, 353(12):1209-23, 2005.
Linder et al., *Clin. Chem.*, 43:254-266, 1997.
Liyou et al., *J. Histochem. Cytochem.*, 51(12):1655-64, 2003.
Mattila et al., *Nucleic Acids Res.*, 19:4967, 1991.
McPherson et al., *PCR Basics: From Background to Bench*, Springer Verlag, 2000.
Meltzer and Bobo, In: *Antipsychotic and Anticholinergic Drugs*, Gelder et al. (Eds.), New Oxford Textbook of Psychiatry, 2$^{nd}$ Ed., Oxford University Press, UK. 2009.
Meltzer et al., *Schizophr. Res.*, 106(2-3):258-64, 2008.
Meltzer, *Int. J. Neuropsychopharmacol.*, 8(2):153-6, 2005.
Minchin et al., *Int. J. Biochem. Cell Biol.*, 40(12):2686-91, 2008.
Myers et al., *Science*, 230:1242, 1985.
Nasrallah, *Acta Psychiatr. Scand.*, 115(4):260-7, 2007.
Nath and Johnson, *Biotechnic. Histochem.*, 73(1):6-22, 1998.
Nielsen et al., *Amer. Chem. Soc.*, 5:1, 1994.
Orita et al., *Proc. Natl. Acad. Sci. USA*, 86:2766-2770, 1989.
*PCR Primer: A Laboratory Manual*, Dieffenbach and Dveksler (Eds.)
PCT Appln. PCT US/93/04145
PCT Appln. WO 92/10092
PCT Appln. WO 95/11995
Perlis et al., *J. Clin. Psychopharmacol.*, 25(5):427-34, 2005.
Practice Guideline for the Treatment of Patients With Schizophrenia, American Psychiatric Association, Second Edition, American Psychiatric Association, 2004.
Purcell et al., *Amer. J. Human Genetics*, 81:559-575, 2007.
Raca et al., *Genet. Test.*, 8(4):387-94, 2004.
Redon et al., *Nature*, 444(7118):444-54, 2006.
Saiki et al., *Nature* (London), 324:163-166, 1986.
Sanger et al., *Proc. Natl. Acad. Sci. USA*, 74:5463-5467, 1977.
Sheffield et al., *Proc. Natl. Acad. Sci. USA*, 86:232-236, 1989.
Snijders et al. In: *Bacterial Artificial Chromosomes: Methods and Protocols*, Zhao et al. (eds), Methods in Molecular Biology, Humana Press, 2002.
Snijders et al., *Nat. Genetics*, 29:263-264, 2001.
Stahl and Grady, *Psychiatr. Serv.*, 57(1):127-9, 2006.
Stroup et al., *Schizophr. Bull.*, 29(1):15-31, 2003.
Sullivan et al., *Mol. Psychiatry*, 13(6):570-584, 2008.
*Treatment of Patients With Bipolar Disorder*, American Psychiatric Association, 2$^{nd}$ Ed., American Psychiatric Association, 2006.
Underhill et al., *Genome Research*, 7(10):996-1005, 1997
Wheeless et al., *Cytometry*, 17:319-326, 1994.
Wu and Wallace, *Genomics*, 4:560, 1989.
Zobel and Maier, *Nervenarzt.*, 75(3):205-14, 2004.

What is claimed is:

1. A method for treating a human subject having or suspected of having a psychotic disorder comprising:
    a) selecting a subject that has been determined to have a SULTA1-1 haplotype, wherein the SULTA1-1 haplotype is defined as a haplotype comprising a C allele at rs763120, a combination of an A allele at rs2285162 and a G allele at rs2285167, or the combination of a T allele at rs2285166 and G allele at rs2285167, and treating the subject that has the SULT4A1-1 haplotype with quetiapine or olanzapine; or
    b) selecting a subject that has been determined not to have the SULT4A1-1 haplotype and treating the subject that does not have the SULT4A1-1 haplotype with an anti-psychotic treatment other than quetiapine or olanzapine.

2. The method of claim 1, wherein the subject comprises the SUTL4A1-1 haplotype and the subject is treated with quetiapine.

3. The method of claim 1, wherein the subject comprises the SUTL4A1-1 haplotype and the subject is treated with olanzapine.

4. The method of claim 1, wherein the subject does not comprise the SULT4A1-1 haplotype and the subject is treated with an anti-psychotic treatment other than quetiapine or olanzapine.

5. The method of claim 4, wherein the anti-psychotic treatment other than quetiapine or olanzapine is risperidone.

6. The method of claim 4, wherein the anti-psychotic treatment other than quetiapine or olanzapine is perphenazine.

7. The method of claim 4, wherein the anti-psychotic treatment other than quetiapine or olanzapine is ziprasidone.

8. The method of claim 1, wherein the psychotic disorder is schizophrenia.

* * * * *

UNITED STATES PATENT AND TRADEMARK OFFICE
CERTIFICATE OF CORRECTION

PATENT NO. : 7,972,793 B2  
APPLICATION NO. : 12/939049  
DATED : July 5, 2011  
INVENTOR(S) : Timothy L. Ramsey et al.

Page 1 of 1

It is certified that error appears in the above-identified patent and that said Letters Patent is hereby corrected as shown below:

In column 4, line 2, delete "SUTL4A1-1" and insert --SULT4A1-1-- therefor.

In column 4, line 13, delete "SUTL4A1-1" and insert --SULT4A1-1-- therefor.

In column 4, line 35, delete "SUTL4A1-1" and insert --SULT4A1-1-- therefor.

In column 4, line 46, delete "SUTL4A1-1" and insert --SULT4A1-1-- therefor.

In column 4, line 58, delete "SUTL4A1-1" and insert --SULT4A1-1-- therefor.

In claim 2, column 75, line 39, delete "SUTL4A1-1" and insert --SULT4A1-1-- therefor.

In claim 3, column 76, line 25, delete "SUTL4A1-1" and insert --SULT4A1-1-- therefor.

Signed and Sealed this  
Twenty-seventh Day of September, 2011

David J. Kappos  
*Director of the United States Patent and Trademark Office*